US 8,252,754 B2

(12) United States Patent
Ambron et al.

(10) Patent No.: US 8,252,754 B2
(45) Date of Patent: Aug. 28, 2012

(54) NEURONAL PAIN PATHWAY

(75) Inventors: Richard Ambron, Lake Success, NY (US); Ying-Ju Sung, Prospect Park, NJ (US); Donald W. Landry, New York, NY (US); Shi-Xian Deng, White Plains, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 11/385,455

(22) Filed: Mar. 21, 2006

(65) Prior Publication Data

US 2006/0216339 A1    Sep. 28, 2006

Related U.S. Application Data

(60) Provisional application No. 60/713,435, filed on Sep. 1, 2005, provisional application No. 60/664,071, filed on Mar. 21, 2005.

(51) Int. Cl.
*C12N 15/11* (2006.01)
*C07H 21/02* (2006.01)
*C07H 21/04* (2006.01)

(52) U.S. Cl. .................. 514/44 A; 536/24.1; 536/24.5

(58) Field of Classification Search .............. 514/44
See application file for complete search history.

(56) References Cited

U.S. PATENT DOCUMENTS

| 4,708,716 A | 11/1987 | Sibalis et al. |
| 5,405,614 A | 4/1995 | D'Angelo et al. |
| 6,476,007 B2 | 11/2002 | Tao et al. |

FOREIGN PATENT DOCUMENTS

| JP | 2000-504697 | 4/2000 |
| WO | WO 9303730 | 3/1993 |
| WO | WO 2004017941 | 3/2004 |

OTHER PUBLICATIONS

Lu et al., (2005). Deliverying siRNA in vivo for functional genomics and novel therapeutics. From RNA Interference Technology (Cambridge, Appasani, ed., pp. 303-317).*
Samarsky et al. (2005). RNAi in drug development: Practical considerations. From RNA Interference Technology (Cambridge, Appasani, ed., pp. 384-395).*
Downward, J. Science, medicine, and the future. RNA interference. BMJ, 2004 vol. 328:1245-1248.*
Nielsen, PE. Systemic delivery. The last hurdle? Gene Therapy, 2005 vol. 12:956-957.*
Agrawal et al. Antisense therapeutics: is it as simple as complementary base recognition? Molecular Medicine Today, 2000 vol. 6:72-81.*

(Continued)

*Primary Examiner* — Terra Cotta Gibbs
(74) *Attorney, Agent, or Firm* — Baker Botts LLP

(57) ABSTRACT

The present invention relates to the discovery of a novel molecular pathway involved in long-term hyperexcitability of sensory neurons, which, in higher animals, is associated with persistent pain. It is based on the discovery that, following injury to an axon of a neuron, an increase in nitric oxide synthase activity results in increased nitric oxide production, which, in turn, activates guanylyl cyclase, thereby increasing levels of cGMP. Increased cGMP results in activation of protein kinase G ("PKG"), which then is retrogradely transported along the axon to the neuron cell body, where it phosphorylates MAPKerk.

9 Claims, 18 Drawing Sheets

OTHER PUBLICATIONS

Figures 1, 1A:
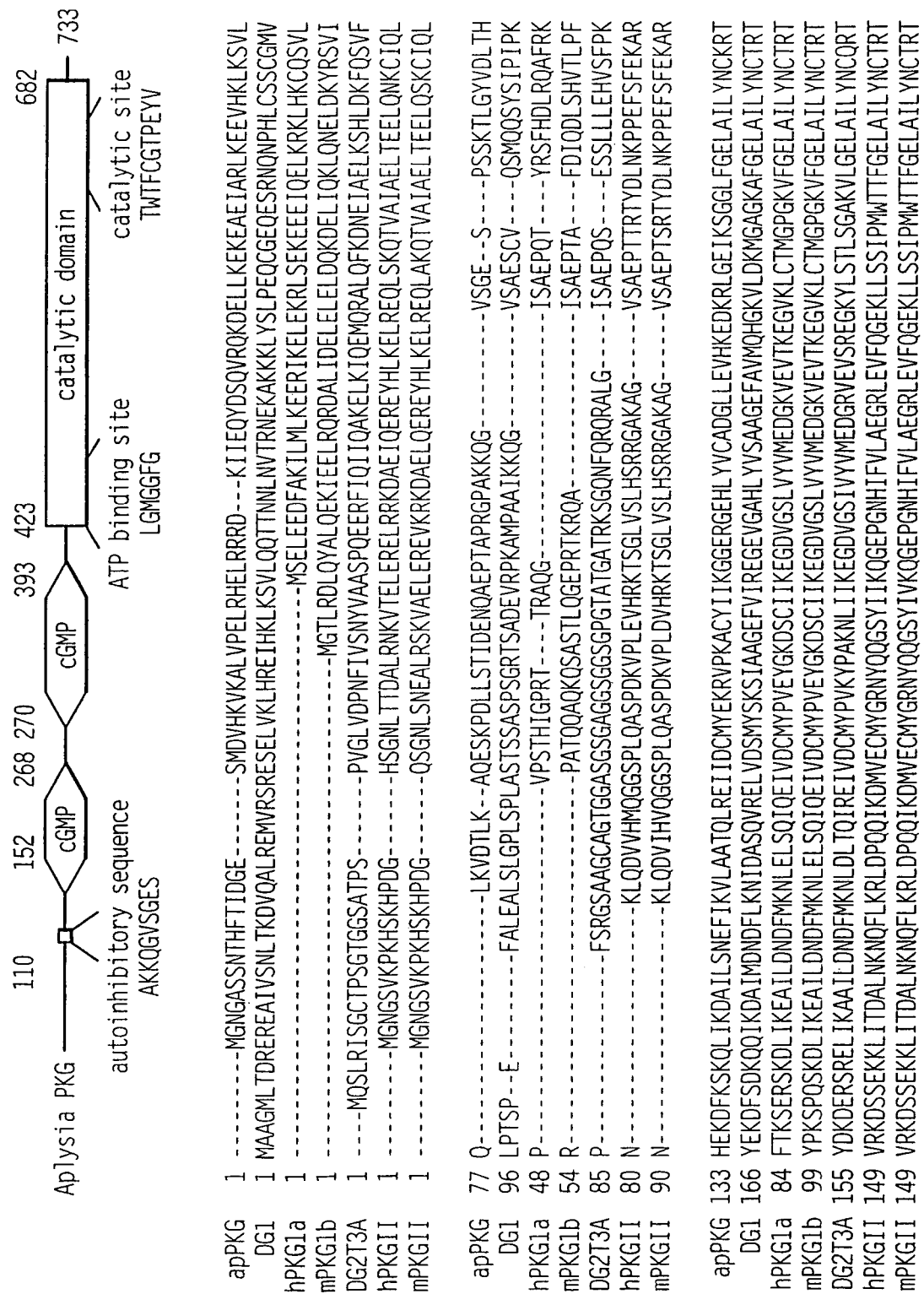

Sung et al. A neuronal isoform of protein kinase G couples mitogen-activated proteinkianse nuclear import to axotomy-induced long-term hyperexcitability in aplysia ssensory neurons. The Journal of Neuroscience, 20004 vol. 24:7583-7595.*

Tischkau et al. (Journal of Neuroscience, 2003 vol. 23:7543-7550).*

Hammond et al. (Nature Genetics 2001, vol. 2:110-119).*

Elbashir et al. (Methods, 2002 vol. 26:199-213).*

Biology Workbench, a point and click interface for searching protein and nucleic acid sequence databases and for analyzing sequence data. Hosted at workbench.sdsc.edu/, (2005).

Sung et al., (2006) Activation and retrograde transport of protein kinase G in rat nociceptive neurons and after nerve injury and inflammation. Neuroscience (Article in Press).

Bennett et al., (2005) The S-LANSS score for identifying pain of predominantly neuropathic origin: validation for use in clinical and postal research. J Pain. 2005 6(3):149-58.

Crown ED, Ye Z, Johnson KM, XU GY, AcAdoo DJ, Westlund KN, Hulsebosch CE (2005) Upregulation of the phosphorylated form of CREB in spinothalamic tract cells following spinal cord injury: relation to central neuropathic pain. Neurosci Lett 384:139-144.

Jarchau et al., (2005) GenBank Accession No. CAA85284 for cGMP dependent protein kinase II [*Rattus norvegicus*].

Ostravik et al., (2005) GenBank Accession No. CAA64318 for Type II cGMP-dependent protein kinase [*Homo sapiens*].

Zhang H, Xie W, Xie Y (2005) Spinal cord injury triggers sensitization of wide dynamic range dorsal horn neurons in segments rostral to injury. Aug. 2, 2005 Brain Res, 1055:103-110.

Bryan J (2004) Transdermal drug delivery may be a common technique in the future. Pharmaceutical J. 273:292-293.

Koesling D, Russwurm M, Mergia E, Mullershausen F, Friebe A. (2004) Nitric oxide-sensitive guanylyl cyclase: structure and regulation. Neurochem Intl. 45:813-819.

Mo E, Amin H, Bianco IH, Garthwaite J. (2004) Kinetics of a cellular nitric oxide/cGMP/phosphodiesterase-5 pathway. J Biol Chem. 279(25):26149-58.

Sung et al., (2004) GenBank Accession No. AY362340 for Aplysia califomica PKG mRNA, complete cds.

Sung YJ, Ambron RT (2004) Pathways that elicit long-term changes in gene expression in nociceptive neurons following nerve injury: contributions to neuropathic pain. Neurol Res 26:195-203.

Sung, YJ, Walters, ET and Ambron, RT (2004) A neuronal isoform of protein kinase G couples mitogen-activated protein kinase nuclear import to axotomy-induced long-term hyperexcitability in Aplysia sensory neurons. J. Neurosci. 24(34):7583-7595.

Walters ET, Bodnarova M, Billy AJ, Dulin MF, Diaz-Rios M, Miller MW, Moroz LL (2004) Somatotopic organization and functional properties of mechanosensory neurons expressing sensorin-A mRNA in Aplysia califomica. J Comp Neurol 471:219-240.

Antonov I, Antonova I, Kandel ER, Hawkins RD (2003) Activity-dependent presynaptic and hebbian LTP are both required and interact during classical conditioning in Aplysia. Neuron 37:135-147.

Griffiths C, Wykes V, Bellamy TC, Garthwaite J.(2003) A new and simple method for delivering clamped nitric oxide concentrations in the physiological range: application to activation of guanylyl cyclase-coupled nitric oxide receptors. Mol Pharmacol. 64(6):1349-56.

Hanz S, Perlson E, Willis D, Zheng JQ, Massarwa R, Huerta JJ, Koltzenburg M, Kohler M, van-Minnen J, Twiss JL, FainzilberM (2003) Axoplasmic importins enable retrograde injury signaling in lesioned nerve. Neuron 40:1095-1104.

Lin H, Bao J, Sung YJ, Walters ET, Ambron RT (2003) Rapid electrical and delayed molecular signals regulate the serum response element after nerve injury: convergence of injury and learning signals. J Neurobiol 57:204-220.

Palecek J, Paleckova V, Willis WD (2003) Fos expression in spinothalamic and postsynaptic dorsal column neurons following noxious visceral and cutaneous stimuli. Pain 104:249-257.

Park SY, Choi JY, Kim RU, Lee YS, Cho HJ, Kim DS (2003) Downregulation of voltage-gated potassium channel α gene expression by axotomy and neurotrophins in rat dorsal root ganglia. Mol Cells 16:256-259.

Sarjeant Jm, Lawrie A, Kinnear C, Yablonsky S, Leung W, Massaeli H, Prichett W, Veinrot JP, Rossart E, Rabinovitch M (2003) Apolipoprotein D inhibits platelet derived growth factor BB-induced vascular proliferated [sic] by preventing translocation of phosphorylated signal regulated kinase 1/2 to the nucleus. Arterioscler. Throm. Vasc. Biol. 23:2172-2177.

Schlossmann J, Feil R, Hofmann F (2003) Signaling through NO and cGMP-dependent protein kinases. Ann Med 35:21-27.

Sung YJ, Dolzhanskaya N, Nolin SL, Brown T, Currie JR, Denman RB (2003) The fragile X mental retardation protein FMRP binds elongation factor 1A mRNA and negatively regulates its translation in vivo. J Biol Chem 278:15669-15678.

Mai et al. (2002) Efficiency of protein transduction is cell type-dependent and is enhanced by dextran sulfate. J Biol Chem 277:30208-30218.

Monfort P, Munoz MD, Kosenko E, Felipo V (2002) Long-term potentiation in hippocampus involves sequential activation of soluble guanylate cyclase, cGMP-dependent protein kinase, and cGMP-degrading phosphodiesterase. J Neurosci 22:10116-10122.

Smith AR, Visioli F, Hagen TM (2002) Vitamin C matters: increased oxidative stress in cultured human aortic endothelial cells without supplemental ascorbic acid. FASEB J 16:1102-1104.

Ungless MA, Gasull X, Walters ET (2002) Long-term alteration of S-type potassium current and passive membrane properties in Aplysia sensory neurons following axotomy. J Neurophysiol 87:2408-2420.

Wang H, Sun H, Della Penna K, Benz RJ, Xu J, Gerhold DL, Holder DJ, Koblan KS (2002) Chronic neuropathic pain is accompanied by global changes in gene expression and shares pathobiology with neurodegenerative diseases. Neuroscience 114:529-546.

Yang Z, Madinova A, Kozai T, Joch H, Aebi U, Luscher TF (2002) Felodipine inhibits nuclear translocation of p42/44 mitogen-activated protein kinase and human smooth muscle growth. Cardiovasc Res 53:227-231.

Zaragoza C, Soria E, Lopez E, Browning D, Balbin M, Lopez-Otin C, Lamas S (2002) Activation of the mitogen activated protein kinase extracellular signal-regulated kinase 1 and 2 by the nitric oxide-cGMP-cGMPdependent protein kinase axis regulates the expression of matrix metalloproteinase 13 in vascular endothelial cells. Mol Pharmacol 62:927-935.

Zhou B, Zhang ZY (2002) The activity of the extracellular signal-regulated kinase 2 is regulated by the differential phosphorylation in the activation loop. J. Biol Chem 277:13889-13899.

Abdulla FA, Smith PA (2001) Axotomy- and autotomy-induced changes in the excitability of rat dorsal root ganglion neurons. J Neurophysiol 85:630-643.

Cha H, Shapiro P (2001) Tyrosine-phosphorylated extracellular signalregulated kinase associates with the Golgi complex during G2/M phase of the cell cycle: evidence for regulation of Golgi structure. J Cell Biol 153:1355-1367.

Farr M, Zhu DF, Povelones M, Valcich D, Ambron RT (2001) Direct interactions between immunocytes and neurons after axotomy in Aplysia. J Neurobiol 46:89-96.

Ji RR, Woolf CJ (2001) Neuronal plasticity and signal transduction in nociceptive neurons: implications for the initiation and maintenance of pathological pain. Neurobiol Dis 8:1-10.

Sadreyev et al., (2001) GenBank Accession No. AAK83069 for nitric oxide synthase [*Aplysia californica*].

Sung YJ, Povelones M, Ambron RT (2001) RISK-1: a novel MAPK homologue in axoplasm that is activated and retrogradely transported after nerve injury. J Neurobiol 47:67-79.

Zimmermann M (2001) Pathobiology of neuropathic pain. Eur J Phannacol 429:23-37.

Dostmann et al., (2000) Highly specific, membrane-permeant peptide blockers of cGMP-dependent protein kinase I alpha inhibit NO-induced cerebral dilation. Proc Natl Acad Sci USA. 97(26):14772-7.

Sung YJ, Conti J, Currie JR, Brown WT, Denman RB (2000) RNAs that interact with the fragile X syndrome RNA binding protein FMRP. Biochem Biophys Res Commun 275:973-980.

Sutton MA, Carew TJ (2000) Parallel molecular pathways mediate expression of distinct forms of intermediate-term facilitation at tail sensory motor synapses in Aplysia. Neuron 26:219-231.

Wender et al. (2000) The design, synthesis, and evaluation of molecules that enable or enhance cellular uptake: peptoid molecular transporters. Proc Natl Acad Sci USA 97: 13003-13008.

Yao et al. (2000) Detection of partially phosphorylated forms of ERK by monoclonal antibodies reveals spatial regulation of ERK activity by phosphatases. FEBS Lett 468:37-42.

Chain et al. (1999) Mechanisms for generating the autonomous cAMP-dependent protein kinase required for long-term facilitation in *Aplysia*. Neuron 22:147-156.

Clatworthy AL, Grose E (1999) Immune-mediated alterations in nociceptive sensory function in *Aplysia californica*. J Exp Biol 202:623-630.

Collins et al., (1999) GenBank Accession No. AF084547 (AAC16044) for cGMP-dependent protein kinase type Ib [*Mus musculus*].

Farr M, Mathews J, Zhu DF, Ambron RT (1999) Inflammation causes a long-term hyperexcitability in the nociceptive sensory neurons of *Aplysia*. Learn Mem 6:331-340.

Hall KU, Collins SP, Gamm DM, Massa E, DePaoli-Roach AA, Uhler MD (1999) Phosphorylation-dependent inhibition of protein phosphatase-1 by G-substrate. A Purkinje cell substrate of the cyclic GMP-dependent protein kinase. J Biol Chem 274:3485-3495.

Lewin MR, Walters ET (1999) Cyclic GMP pathway is critical for inducing long-term sensitization of nociceptive sensory neurons. Nat Neurosci 2:18-23.

Liao X, Gunstream JD, Lewin MR, Ambron RT, Walters ET (1999) Activation of protein kinase A contributes to the expression but not the induction of long-term hyperexcitability caused by axotomy of *Aplysia* sensory neurons. J Neurosci 19:1247-1256.

Millan MJ (1999) The induction of pain: an integrative review. Prog Neurobiol 57:1-164.

Setyawan et al. (1999) Inhibition of protein kinases by balanol: specificity within the serine/threonine protein kinase subfamily. Mol Pharmacol. 56(2):370-6.

Tamura et al., (1999) GenBank Accession No. BAA08297 for cGMP-dependent protein kinase type I alpha [*Homo sapiens*].

Urban MO and Gebhart GF (1999) Supraspinal contributions to hyperalgesia. Proc Natl Acad Sci USA 96:7687-7692.

Bedi SS, Salim A, Chen S, Glanzman DL (1998) Long-term effects of axotomy on excitability and growth of isolated *Aplysia* sensory neurons in cell culture: potential role of cAMP. J Neurophysiol 79:1371-1383.

Chen Y, Devor M (1998) Ectopic mechanosensitivity in injured sensory axons arises from the site of spontaneous electrogenesis. Eur J Pain 2:165-178.

Dash PK, Tian LM, Moore AN (1998) Sequestration of cAMP response element-binding proteins by transcription factor decoys causes collateral elaboration of regenerating *Aplysia* motor neuron axons. Proc Natl Acad Sci USA 95:8339-8344.

Kim et al. (1998) Cell type-specific changes of the membrane properties of peripherally-axotomized dorsal root ganglion neurons in a rat model of neuropathic pain. Neuroscience 86:301-309.

Michael D, Martin KC, Seger R, Ning MM, Baston R, Kandel ER (1998) Repeated pulses of serotonin required for long-term facilitation activate mitogen-activated protein kinase in sensory neurons of Aplysia. Proc Natl Acad Sci USA 95:1864-1869.

Muller U, Carew TJ (1998) Serotonin induces temporally and mechanistically distinct phases of persistent PKA activity in *Aplysia* sensory neurons. Neuron 21:1423-1434.

Smolenski et al. (1998) Analysis and regulation of vasodilatorstimulated phosphoprotein serine 239 phosphorylation in vitro and in intact cells using a phosphospecific monoclonal antibody. J Biol Chem 273:20029-20035.

Urban MO and Gebhart GF (1998) The glutamate synapse: a target in the pharmacological management of hyperalgesic pain states. Prog Brain Res 116:407-420.

Gudi et al. (1997) Regulation of gene expression by cyclic GMP-dependent protein kinase requires nuclear translocation of the kinase: identification of a nuclear localization signal. Mol Cell Biol 17:5244-5254.

Martin et al. (1997) MAP kinase translocates into the nucleus of the presynaptic cell and is required for long-term facilitation in *Aplysia*. Neuron. 18(6):899-912.

Schmied R, Ambron RT (1997) Anuclear localization signal targets proteins to the retrograde transport system, thereby evading uptake into organelles in *Aplysia* axons. J Neurobiol 33:151-160.

Zhang JM, Donnelly DF, Song XJ, Lamotte RH (1997) Axotomy increases the excitability of dorsal root ganglion cells with unmyelinated axons. J Neurophysiol 78:2790-2794.

Ambron RT, Walters ET (1996) Priming events and retrograde injury signals. A new perspective on the cellular and molecular biology of nerve regeneration. Mol Neurobiol 13:61-79.

Ambron RT, Zhang XP, Gunstream JD, Povelones M, Walters ET (1996) Intrinsic injury signals enhance growth, survival, and excitability of *Aplysia* neurons. J Neurosci 16:7469-7477.

Byrne JH, Kandel ER (1996) Presynaptic facilitation revisited: state and time dependence. J Neurosci 16:425-435.

Foster et al., (1996) GenBank Accession No. AAB03405 for cGMP-dependent protein kinase [*Drosophila melanogaster*].

Moroz et al (1996) Nitric oxide synthase activity in the molluscan CNS. J Neurochem 66:873-876.

Study RE, Kral MG (1996) Spontaneous action potential activity in isolated dorsal root ganglion neurons from rats with a painful neuropathy. Pain 65:235-242.

Sung YJ, Hwang MC Hwang YW (1996) The dominant negative effects of H-Ras harboring a Gly to Ala mutation at position 60. J Biol Chem 271:30537-30543.

Ambron et al. (1995) Axoplasm enriched in a protein mobilized by nerve injury induces memorylike alterations in *Aplysia neurons*. J Neurosci 15:3440-3446.

Bartsch et al. (1995) *Aplysia* CREB2 represses long-term facilitation: relief of repression converts transient facilitation into long-term functional and structural change. Cell 83:979-992.

Clatworthy AL, Illich PA, Castro GA, Walters ET (1995) Role of peri-axonal inflammation in the development of thermal hyperalgesia and guarding behavior in a rat model of neuropathic pain. Neurosci Lett 184:5-8.

Gunstream JD, Castro GA, Walters ET (1995) Retrograde transport of plasticity signals in *Aplysia* sensory neurons following axonal injury. J Neurosci 15:439-448.

Johanson SO, Crouch MF, Hendry IA (1995) Retrograde axonal transport of signal transduction proteins in rat sciatic nerve. Brain Res 690:55-63.

Pohler et al. (1995) Expression, purification, and characterization of the cGMP-dependent protein kinases I_and II using the baculovirus system. FEBS Lett 374:419-425.

Whitmarsh AJ, Shore P, Sharrocks AD, Davis RJ (1995) Integration of MAP kinase signal transduction pathways at the serum response element. Science 269:403-407.

Xu S, Robbins D, Frost J, Dang A, Lange-Carter C, Cobb MH (1995) MEKK1 phosphorylates MEK1 and MEK2 but does not cause activation of mitogenactivated protein kinase. Proc Natl Acad Sci USA 92:6808-6812.

Alberini CM, Ghirardi M, Metz R, Kandel ER (1994) C/EBP is an immediate-early gene required for the consolidation of long-term facilitation in *Aplysia*. Cell 76:1099-1114.

DesGroseillers L, Auclair D, Wickham L, Maalouf M (1994) A novel actin cDNA is expressed in the neurons of *Aplysia californica*. Biochim Biophys Acta 1217:322-324.

DesGroseillers et al. (1994) GenBank Accession No. U01352 for *Aplysia californica* actin mRNA, complete cds.

Francis SH, Corbin JD (1994) Structure and function of cyclic nucleotidedependent protein kinases. Annu Rev Physiol 56:237-272.

Karin M (1994) Signal transduction from the cell surface to the nucleus through the phosphorylation of transcription factors. Curr Opin Cell Biol 6:415-424.

Walters ET (1994) Injury-related behavior and neuronal plasticity: an evolutionary perspective on sensitization, hyperalgesia, and analgesia. Int Rev Neurobiol 36:325-427.

Waxman SG, Kocsis JD, Black JA (1994) Type III sodium channel mRNA is expressed in embryonic but not adult spinal sensory neurons, and is reexpressed following axotomy. J Neurophysiol 72:466-470.

Fiallos-Estrada et al. (1993) Long-lasting increase of nitric oxide synthetase immunoreactivity, NADPH-diaphorase reaction and c-JUN co-expression in rat dorsal root ganglion neurons following sciatic nerve transection. Neurosci Lett 150:169-173.

Kalderon et al. (1993) GenBank Accession No. AAA28459 for cGMP-dependent protein kinase.

Lee JH, Orice RH, Williams FG, Mayer B, Beitz AJ (1993) Nitric oxide synthase is found in some spinothalamic neurons and in neuronal processes that appose spinal neurons that express Fos induced by noxious stimulation. Brain Res 608:324-333.

Marais R, Wynne J, Treisman R (1993) The SRF accessory protein Elk-1 contains a growth factor-regulated transcriptional activation domain. Cell 73:381-393.

Schmied et al. (1993) Endogenous axoplasmic proteins and proteins containing nuclear localization signal sequences use the retrograde axonal transport/nuclear import pathway in Aplysia neurons. J Neurosci 13:4064-4071.

Uhler et al. (1993) GenBank Accession No. AAA02572 for cyclic GMP-dependent protein kinase II.

Zhang X, Verge V, Wiesenfeld-Hallin Z, Ju G, Bredt D, Synder SH, Hokfelt T (1993) Nitric oxide synthase-like immunoreactivity in lumbar dorsal root ganglia and spinal cord of rat and monkey and effect of peripheral axotomy. J Comp Neurol 335:563-575.

Ambron RT, Schmied R, Huang CC, SmedmanM (1992) A signal sequence mediates the retrograde transport of proteins from the axon periphery to the cell body and then into the nucleus. J Neurosci 12:2813-2818.

Ghirardi M, Braha O, Hochner B, Montarolo PG, Kandel ER, Dale N (1992) Roles of PKA and PKC in facilitation of evoked and spontaneous transmitter release at depressed and nondepressed synapses in *Aplysia* sensory neurons. Neuron 9:479-489.

Goldsmith BA, AbramsTW (1992) cAMP modulates multiple K+ currents, increasing spike duration and excitability in *Aplysia* sensory neurons. Proc Natl Acad Sci USA 89:11481-11485.

Gracely RH, Lynch SA, Bennett GJ (1992) Painful neuropathy: altered central processing maintained dynamically by peripheral input. Pain 51:175-194.

Verge VM, Xu Z, Xu XJ, Wiesenfeld-Hallin Z, Hokfelt T (1992) Marked increase in nitric oxide synthase mRNA in rat dorsal root ganglia after peripheral axotomy: in situ hybridization and functional studies. Proc Natl Acad Sci USA 89:11617-11621.

Brunet et al. (1991) Identification of a peptide specific for *Aplysia* sensory neurons by PCR-based differential screening. Science 252:856-859.

Bfunet et al. (1991) GenBank Accession No. X56770 for *A.californica* pscl mRNA for sensorin A.

LaMotte RH, Shain CN, Simone DA, Tsai EFP (1991) Neurogenic hyperalgesia: psychophysical studies of underlying mechanisms. J Neurophysiol 66:190-211.

Scott JD (1991) Cyclic nucleotide-dependent protein kinases. Pharmacol Ther 50:123-145.

Walters ET, Alizadeh H, Castro GA (1991) Similar neuronal alterations induced by axonal injury and learning in Aplysia. Science 253:797-799.

Bredt DS, Snyder SH (1990) Isolation of nitric oxide synthetase, a calmodulin-requiring enzyme. Proc Natl Acad Sci USA 87:682-685.

Ausubel F.M. et al., eds. (1989) Current Protocols in Molecular Biology, vol. I, Green Publishing Associates, Inc., and John Wiley & sons, Inc., New York, at p. 2.10.3.

Billy AJ, Walters ET (1989) Long-term expansion and sensitization of mechanosensory receptive fields in *Aplysia* support an activity-dependent model of whole-cell sensory plasticity. J Neurosci 9:1254-1262.

Glanzman DL, Kandel ER, Schacher S (1989) Identified target motor neuron regulates neurite outgrowth and synapse formation of *Aplysia* sensory neurons in vitro. Neuron 3:441-450.

Dale N, Schacher S, Kandel ER (1988) Long-term facilitation in *Aplaysia* involves increase in transmitter release. Science 239:282-285.

Scholz KP, Byrne JH (1988) Intracellular injection of cAMP induces a longterm reduction of neuronal K+ currents. Science 240:1664-1666.

Wall PD, Devor M (1983) Sensory afferent impulses originate from dorsal root ganglia as well as from the periphery in normal and nerve injured rats. Pain 17:321-339.

Walters et al. (1983) Mechanoafferent neurons innervating tail of *Aplysia*. I. Response properties and synaptic connections. J Neurophysiol 50:1522-1542.

Walters et al (1983) Mechanoafferent neurons innervating tail of *Aplysia*. II. Modulation by sensitizing stimulation. J Neurophyiol 50:1543-1559.

Woolf CJ (1983) Evidence for a central component of post-injury pain hypersensitivity. Nature 306:686-688.

Glass DB, Krebs EG (1982) Phosphorylation by guanosine 3':5'-monophosphate-dependent protein kinase of synthetic peptide analogs of a site phosphorylated in histone H2B. J Biol Chem 257:1196-1200.

Dagan D, Levitan IB (1981) Isolated identified *Aplysia* neurons in cell culture. J Neurosci 1:736-740.

The Merck Manual of Diagnosis and Therapy, Section 14, Chapter 165, Figure 165-2, which references Keegan JJ and Garrett FD, Anatomical Record 102:409-437, 1948, used with permission of the Wistar Institute, Philadelphia, PA.

Krieg et al., 2004, "Peptide blockers of PKG inhibit ROS generation by acetylcholine and bradykinin in cardiomyocytes but fail to block protection in the whole heart," *Am. J. Physiol. Heart. Circ. Physiol.*, vol. 288: p. H1976-H1981.

Schmidtko et al., 2003, "Inhibition of cyclic guanosine 5'-monophosphate-dependent protein kinase I (PKG-I) in lumbar spinal cord reduces formalin-induced hyperalgesia and PKG upregulation," *Nitric Oxide*, vol. 8: p. 89-94.

Elbashir, et al., 2001, "Duplexes of 21-nucleotide RNAs mediate RNA interference in cultured mammalian cells." Nature, 411 :494-498.

Fire, et al., 1998, "Potent and specific genetic interference by double-stranded RNA in *Caenorhabditis elegans*." Nature, 391 :806-11.

"Block-iT™ RNAi Designer," by Invitrogen, Carlsbad, CA [retrieved on Jun. 26, 2009] Retrieved from the Internet: <URL: https://rnaidesigner.beta.invitrogen.com/rnaiexpress/>.

Christensen et al., "Cyclic GMP-dependent protein kinase Ialpha inhibits thrombin receptor-mediated calcium mobilization in vascular smooth muscle cells," J. Biol. Chem., 281(13):8409-8416, (2006).

Manjeet et al., "Quercetin inhibits LPS-induced nitric oxide and tumor necrosis factor-alpha production in murine macrophages", *Int. J. Immunopharmacol*, 1999, 21(7): 435-43.

Kotera et al., "cGMP-dependent protein kinase protects cGMP from hydrolysis by phosphodiesterase-5", *Biochem. J.*, 2003, vol. 372, No. Pt. 2: 419-26.

Okada et al., Allosteric activation of CGMP-specific, cGMP-binding phosphosdiesterase (PDES) by cGMP, *Biochemistry*, 2002, 41(30): 9672-9.

* cited by examiner

```
apPKG  228  ASVKAVTHTT-LWVLDRRVFQAIMMKTGLQRREENMAFLKSVPLLKNLPSDKLAKMSDVLEYDFFHENEYIIREGAAGDTFFILNKGEVKVTQKI
DG1    261  ASIRVLSEAARVWVLDRRVFQQIMMCTGLQRIENSVNFLRSVPLLMNLSEELLAKIADVLELEFYAAGTYIIRQGTAGDSFFLISQGNVRVTQKL
hPKG1a 179  ATVKTLVNVK-LWAIDRQCFQTIMMRTGLIKHTEYMEFLKSVPTFQSLPEEILSKLADVLEETHYENGEYIIRQGARGDTFFIISKGTVNVTRED
mPKG1a 194  ATVKTLVNVK-LWAIDRQCFQTIMMRTGLIKHTEYMEFLKSVPTFQSLPEEILSKLADVLEETHYENGEYIIRQGARGDTFFIISKGQVNVTRED
DG2T3A 250  ATITAITECN-LWAIERQCFQTIMMRTGLIRQAEYSDFLKSVPIFKDLAEDTLIKISDVLEETHYQRGDHIVRQGARGDTFFIISKGKVRVTIKQ
hPKGII 244  ASVKAITNVK-TWALDREVFQNIMRRTAQARDEYRNFLRSVSLLKNLPEDKLTKIIDCLEVEYYDKGDYIIREGEEGSTFFILAKGKVKVTQST
mPKGII 244  ASVKAITNVK-TWALDREVFQNIMRRTAQARDEYRNFLRSVSLLKNLPEDKLTKIIDCLEVEYYDKGDYIIREGEEGSTFFILAKGKVKVTQST apPKG  322  AGHA-EPKEVRRLKRGDYFGEKALLSEDRRTANVIALPP-GVECLTVDRESFTQFVGDLNELR-------NKDYGDEARGAERRSG------SD
DG1    356  TPTSPEETELRTLSRGDYFGEKALQGEDALINEDKRTANIIALSP-GVECLTLDRDSFKRLIGDLCELK-------EKDYGDESRKLAMKQA------RE
hPKG1a 273  SPSE-DPVFLRTLGKGDWFGEKALQGEDVRTANVIAAEA--VTCLVIDRDSFKHLIGGLDDVS--------NKAYEDAEAKAKYEA--------------
mPKG1a 288  SPSE-DPVFLRTLGKGDWFGEKALQGEDVRTANVIAAEA--VTCLVIDRDSFKHLIGGLDDVS--------NKAYEDAEAKAKYEA--------------
DG2T3A 344  QDRQ-EEKFIRMLGKGDFFGEKALQGDDLRTANIICESADGVSCLVIDRETFNQLISNLDEIK--------HR-YDDEG-AMERRK--------------
hPKGII 338  EGHD-QPQLIKTLQKGEYFGEKALQGEDVANLNRDDEKRHAKRSMSNWKLSKAL
mPKGII 338  EGHD-QPQLIKTLQKGEYFGEKALQGEDVATLNRDDEKRHAKRSMSSWKLSKAL apPKG  401  STVSPVSERPVAKEFENCSLDDLQLVTTLGMGGFGRVELVQLS-KEKGKTFALKCLKKKHIVETRQQEHIYSEKKIMEADSPFITKLHKTFRDR
DG1    346  SCQDEPKEQ-LQQEFPDLKLTDLEVVSTLGIGGFGRVELVQLKVKAHHQDRVDIFALKCLKKRHIVDTKQEEHFSERHIMLSSRSPFICRLYRTFRDE
hPKG1a 348  ----------EAAFFANLKLSDFNIIDTLGVGGFGRVELVQLK-SEESKTFAMKILKKRHIVDTRQQEHIRSEKQIMQGAHSDFIVRLYRTFKDS
mPKG1a 363  ----------EAAFFANLKLSDFNIIDTLGVGGFGRVELVQLK-SEESKTFAMKILKKRHIVDTRQQEHIRSEKQIMQGAHSDFIVRLYRTFKDS
DG2T3A 419  ----------INEEFRDINLTDLRVIATLGVGGFGRVELVQTN-GDSSRSFALKQMKKSQIVETRQQHIMSEKEIMGEANCQFIVKLFKTFKDK
hPKGII 431  SLEMIQLKEKVARFSSSSPFQNLEIIATLGVGGFGRVELVKVK--NENVAFAMKCIRKKHIVDTKQQEHVYSEKRILEELCSPFIVKLYRTFKDN
mPKGII 431  SLEMIQLKEKVARFSSTSPFQNLEIIATLGVGGFGRVELVKVK--NENIAFAMKCIRKKHIVDTKQQEHVYSEKRILEELCSPFIVKLYRTFKDN
```

FIG. 1A-2

```
apPKG   495  KYVYVMLMEVCLGGELWTILRDRGNFDDLTARFCVACVLEAFSYLHAKGIIYRDLKPENLLLDARGYVKLVDFGFAKKIGVGKKTWTFCGTPEYVA
DG1     530  KYVYVMLLEACMGGEIWTMLRDRGSFEDNAAQFIIGCVLQAFEYLHARGIIYRDLKPENMLDERGYVKIVDFGFAKQIGTSSKTWTFCGTPEYVA
hPKG1a   432  KYLYMLMEACLGGELWTILRDRGSFEDSTRFYTACVVEAFAYLHSKGIIYRDLKPENLILDHRGYAKLVDFGFAKKIGFGKKTWTFCGTPEYVA
mPKG1b   447  KYLYMLMEACLGGELWTILRDRGSFEDSTRFYTACVVEAFAYLHSKGIIYRDLKPENLILDHRGYAKLVDFGFAKKIGFGKKTWTFCGTPEYVA
DG2T3A   503  KYLYMLMESCLGGELWTILRDKGNFDDSTRFYTACVVEAFDYLHSRNIIYRDLKPENLLNERGYGKLVDFGFAKKLQTGRKTWTFCGTPEYVA
hPKGII   524  KYVYVMLLEACLGGELWSILRDRGSFDEPTSKFCVACVTEAFDYLHRLGIIYRDLKPENLILDAEGYLKLVDFGFAKKIGSGQKTWTFCGTPEYVA
mPKGII   524  KYVYVMLLEACLGGELWSILRDRGSFDEPTSKFCVACVTEAFDYLHRLGIIYRDLKPENLILDADGYLKLVDFGFAKKIGSGQKTWTFCGTPEYVA apPKG   590  PEIILNKGHDHSADYWSLGILMYELLNGTPPFSGSDPMRTYNIILKGIDHIEFPKKISRSAHVLIKKLCRDNPMERLGYGKNGISDIRKNKWFQG
DG1     625  PEIILNKGHDHSADYWSLGILMYELLNGTPPFSGSDPMRTYNIILKGIDHIEFPKKISRSAPDPMQTYNLILKGIDMIAFPKHISRWAVQLIKRLCRDVPSERLGYOTGGIQDIKKHKWFLG
hPKG1a   527  PEIILNKGHDHSADYWSLGILMYELLTGSPPFSGPDPMKTYNIILRGIDMIEFPKKIAKNAANLIKKLCRDNPSERLGNLKNGVKDIQKHKWFEG
mPKG1b   542  PEIILNKGHDHSADYWSLGILMYELLTGSPPFSGPDPMKTYNIILRGIDMIEFPKKIAKNAANLIKKLCRDNPSERLGNLKNGVKDIQKHKWFEG
DG2T3A   598  PEVILNRGHDISADYWSLGVLMFELLTGTPPFTGSDPMRTYNIILKGIDAIEFPRNITRNASNLIKKLCRDNPAERLGYQRGGISEIQKKWFDG
hPKGII   619  PEVILNKGHDFSVDFWSLGILVYELLTGNPPFSGVDQMMTYNLILKGIEKMDFPRKITRRPEDLIRRLCRQNPTERLGNLKNGINDIKKHRWLNG
mPKGII   619  PEVILNKGHDFSVDFWSLGILVYELLTGNPPFSGIDQMMTYNLILKGIEKMDFPRKITRRPEDLIRRLCRQNPTERLGNLKNGINDIKKHRWLNG apPKG   685  FDWDGLMDLTLTPPIVPKVKNPTDTSNFDSYPRDMD-IAADELSGWDIDF
DG1     720  FDWDGLASQLLIPPFVRPIAHPTDVRYFDRFPCDLN-EPPDELSGWDADF
hPKG1a   622  FNWEGLRKGTLTPPIIPSVASPTDTSNFDSFPEDNDEPPPDDNSGWDIDF
mPKG1b   637  FNWEGLRKGTLTPPIIPSVASPTDTSNFDSFPEDSDEPPPDDNSGWDIDF
DG2T3A   693  FYWWGLQNCTLEPPIKPAVKSVVDTTNFDDYPPDEGPPPDDVTGWDKDF
hPKGII   714  FNWEGLKARSLPSPLQRELKGPIDHSYFDKYPPEKG-MPPDELSGWDKDF
mPKGII   714  FNWEGLKARSLPSPLRRELSGPIDHSYFDKYPPEKG-VPPDEMSGWDKDF
```

FIG. 1A-3

SEQUENCE LISTING

```
<160> NUMBER OF SEQ ID NOS: 58

<210> SEQ ID NO 1
<211> LENGTH: 20
<212> TYPE: DNA
<213> ORGANISM: artificial sequence
<220> FEATURE:
<223> OTHER INFORMATION: synthetic oligonucleotide
<220> FEATURE:
<221> NAME/KEY: misc_feature
<222> LOCATION: (3)..(3)
<223> OTHER INFORMATION: y= t or c
<220> FEATURE:
<221> NAME/KEY: misc_feature
<222> LOCATION: (6)..(6)
<223> OTHER INFORMATION: y= t or c
<220> FEATURE:
<221> NAME/KEY: misc_feature
<222> LOCATION: (9)..(9)
<223> OTHER INFORMATION: y= t or c
<220> FEATURE:
<221> NAME/KEY: misc_feature
<222> LOCATION: (12)..(12)
<223> OTHER INFORMATION: n= a, c, g or t
<220> FEATURE:
<221> NAME/KEY: misc_feature
<222> LOCATION: (13)..(13)
<223> OTHER INFORMATION: m= a or c
<220> FEATURE:
<221> NAME/KEY: misc_feature
<222> LOCATION: (15)..(15)
<223> OTHER INFORMATION: n= a, c, g, or t
<220> FEATURE:
<221> NAME/KEY: misc_feature
<222> LOCATION: (15)..(15)
<223> OTHER INFORMATION: n= inosine
<220> FEATURE:
<221> NAME/KEY: misc_feature
<222> LOCATION: (18)..(18)
<223> OTHER INFORMATION: n=  a, c, g, or t

<400> SEQUENCE: 1
tayaaytgya cnmgnacngc                                                  20

<210> SEQ ID NO 2
<211> LENGTH: 20
<212> TYPE: DNA
<213> ORGANISM: artificial sequence
<220> FEATURE:
<223> OTHER INFORMATION: synthetic oligonucleotide
<220> FEATURE:
<221> NAME/KEY: misc_feature
<222> LOCATION: (3)..(3)
```

```
<223> OTHER INFORMATION: r= g or a
<220> FEATURE:
<221> NAME/KEY: misc_feature
<222> LOCATION: (6)..(6)
<223> OTHER INFORMATION: r= g or a
<220> FEATURE:
<221> NAME/KEY: misc_feature
<222> LOCATION: (9)..(9)
<223> OTHER INFORMATION: n= a, c, g or t
<220> FEATURE:
<221> NAME/KEY: misc_feature
<222> LOCATION: (15)..(15)
<223> OTHER INFORMATION: n= a, c, g or t
<220> FEATURE:
<221> NAME/KEY: misc_feature
<222> LOCATION: (18)..(18)
<223> OTHER INFORMATION: y= c or t

<400> SEQUENCE: 2
ccrcaraang tccangtytt                                              20

<210> SEQ ID NO 3
<211> LENGTH: 22
<212> TYPE: DNA
<213> ORGANISM: artificial sequence
<220> FEATURE:
<223> OTHER INFORMATION: synthetic oligonucleotide

<400> SEQUENCE: 3
cgcctgtcca gcacccatag cg                                           22

<210> SEQ ID NO 4
<211> LENGTH: 21
<212> TYPE: DNA
<213> ORGANISM: artificial sequence
<220> FEATURE:
<223> OTHER INFORMATION: synthetic oligonucleotide

<400> SEQUENCE: 4
gggtgaccgc tttcacggag g                                            21

<210> SEQ ID NO 5
<211> LENGTH: 20
<212> TYPE: DNA
<213> ORGANISM: artificial sequence
<220> FEATURE:
<223> OTHER INFORMATION: synthetic oligonucleotide

<400> SEQUENCE: 5
cggcaaggtt ctgcgtcgcc                                              20

<210> SEQ ID NO 6
<211> LENGTH: 19
<212> TYPE: DNA
<213> ORGANISM: artificial sequence
<220> FEATURE:
<223> OTHER INFORMATION: synthetic oligonucleotide

<400> SEQUENCE: 6
ggacgcgagg ggatacgtc                                               19

<210> SEQ ID NO 7
<211> LENGTH: 33
<212> TYPE: DNA
<213> ORGANISM: artificial sequence
<220> FEATURE:
<223> OTHER INFORMATION: synthetic oligonucleotide

<400> SEQUENCE: 7
```

-continued

```
ggtggaggag atagcggcgg ttctgtgaac gcc                                    33
```

<210> SEQ ID NO 8
<211> LENGTH: 21
<212> TYPE: DNA
<213> ORGANISM: artificial sequence
<220> FEATURE:
<223> OTHER INFORMATION: synthetic oligonucleotide

<400> SEQUENCE: 8

```
ggaggagtga gggtcagatc c                                                 21
```

<210> SEQ ID NO 9
<211> LENGTH: 2202
<212> TYPE: DNA
<213> ORGANISM: Aplysia californica
<220> FEATURE:
<221> NAME/KEY: CDS
<222> LOCATION: (1)..(2202)
<223> OTHER INFORMATION: PGK mRNA, complete cds

<400> SEQUENCE: 9

```
atg ggc aac ggt gcc agt tcg aac acg cac ttc acc ata gac ggt gag        48
Met Gly Asn Gly Ala Ser Ser Asn Thr His Phe Thr Ile Asp Gly Glu
 1               5                  10                  15 tcg atg gac gtt cac aaa gtc aag gcg ttg gtc cca gag ctc cgg cat        96
Ser Met Asp Val His Lys Val Lys Ala Leu Val Pro Glu Leu Arg His
             20                  25                  30 gag ctc aga cgg cgg gat aag atc atc gag cag tac gac tcg caa gtg       144
Glu Leu Arg Arg Arg Asp Lys Ile Ile Glu Gln Tyr Asp Ser Gln Val
         35                  40                  45 cga cag aag gac gag ttg ctg aaa gaa aaa gaa gcg gag atc gct cgc       192
Arg Gln Lys Asp Glu Leu Leu Lys Glu Lys Glu Ala Glu Ile Ala Arg
     50                  55                  60 ctc aaa gaa gag gtt cac aag ctg aaa tcg gtt ctg cag ctc aaa gtg       240
Leu Lys Glu Glu Val His Lys Leu Lys Ser Val Leu Gln Leu Lys Val
 65                  70                  75                  80 gac acg ctg aaa gcc cag gag agt aag cca gac ctc ctg tcc act atc       288
Asp Thr Leu Lys Ala Gln Glu Ser Lys Pro Asp Leu Leu Ser Thr Ile
                 85                  90                  95 gac gaa aac cag gcc gag cct act gct cct cgt ggc cct gct aaa aag       336
Asp Glu Asn Gln Ala Glu Pro Thr Ala Pro Arg Gly Pro Ala Lys Lys
            100                 105                 110 cag ggt gtg tcg gga gag agc ccc agc tca aag acc ctg ggc tat gtg       384
Gln Gly Val Ser Gly Glu Ser Pro Ser Ser Lys Thr Leu Gly Tyr Val
        115                 120                 125 gat cta aca cac cac gaa aag gat ttc aaa tcg aaa cag cta atc aaa       432
Asp Leu Thr His His Glu Lys Asp Phe Lys Ser Lys Gln Leu Ile Lys
    130                 135                 140 gac gcc atc ttg agc aac gag ttc atc aaa gtg cta gcg gcc acg cag       480
Asp Ala Ile Leu Ser Asn Glu Phe Ile Lys Val Leu Ala Ala Thr Gln
145                 150                 155                 160 ctc cgg gag atc atc gac tgc atg tac gag aag cgc gtg ccc aag gcg       528
Leu Arg Glu Ile Ile Asp Cys Met Tyr Glu Lys Arg Val Pro Lys Ala
                165                 170                 175 tgc tac att atc aag gga gga gag cgg ggc gag cat ctc tat gtc tgc       576
Cys Tyr Ile Ile Lys Gly Gly Glu Arg Gly Glu His Leu Tyr Val Cys
            180                 185                 190 gca gat ggt ctc ctg gag gtg cat aag gag gac aag agg ctg gga gaa       624
Ala Asp Gly Leu Leu Glu Val His Lys Glu Asp Lys Arg Leu Gly Glu
        195                 200                 205 atc aag tcc ggg ggc ctc ttc ggc gag ctc gcc ata ctg tac aac tgt       672
Ile Lys Ser Gly Gly Leu Phe Gly Glu Leu Ala Ile Leu Tyr Asn Cys
```

```
                    210                 215                 220
aag cgg acc gcc tcc gtg aaa gcg gtc acc cac act acg cta tgg gtg     720
Lys Arg Thr Ala Ser Val Lys Ala Val Thr His Thr Thr Leu Trp Val
225                 230                 235                 240 ctg gac agg cga gtg ttc cag gcc att atg atg aaa acc gga cta cag     768
Leu Asp Arg Arg Val Phe Gln Ala Ile Met Met Lys Thr Gly Leu Gln
                245                 250                 255 agg agg gag gag aat atg gcc ttc ctc aaa agc gtg cct ttg ctc aaa     816
Arg Arg Glu Glu Asn Met Ala Phe Leu Lys Ser Val Pro Leu Leu Lys
            260                 265                 270 aac ctg cct tcc gac aaa ctg gcc aag atg tct gat gtc cta gaa tac     864
Asn Leu Pro Ser Asp Lys Leu Ala Lys Met Ser Asp Val Leu Glu Tyr
        275                 280                 285 gat ttc ttc cac gag aac gaa tat atc atc aga gaa ggg gca gct ggt     912
Asp Phe Phe His Glu Asn Glu Tyr Ile Ile Arg Glu Gly Ala Ala Gly
    290                 295                 300 gac acg ttc ttc atc ctg aac aag gga gag gtc aag gtc acc cag aaa     960
Asp Thr Phe Phe Ile Leu Asn Lys Gly Glu Val Lys Val Thr Gln Lys
305                 310                 315                 320 att gca ggt cat gca gag cct aaa gaa gtg cgc cga cta aag agg ggt    1008
Ile Ala Gly His Ala Glu Pro Lys Glu Val Arg Arg Leu Lys Arg Gly
                325                 330                 335 gat tac ttt gga gaa aaa gcg tta tta agt gaa gat agg agg aca gcc    1056
Asp Tyr Phe Gly Glu Lys Ala Leu Leu Ser Glu Asp Arg Arg Thr Ala
            340                 345                 350 aac gtg atc gct cta cct cct ggt gtt gaa tgt ctc acc gtg gac aga    1104
Asn Val Ile Ala Leu Pro Pro Gly Val Glu Cys Leu Thr Val Asp Arg
        355                 360                 365 gag tct ttc acc cag ttt gtc ggt gac ctc aac gaa ctt cgc aac aaa    1152
Glu Ser Phe Thr Gln Phe Val Gly Asp Leu Asn Glu Leu Arg Asn Lys
    370                 375                 380 gac tat ggc gac gaa gcc cgg gga gca gaa cgg cgt agc ggc agc gac    1200
Asp Tyr Gly Asp Glu Ala Arg Gly Ala Glu Arg Arg Ser Gly Ser Asp
385                 390                 395                 400 agt acc gta tcc cca gtg tcg gag cga cca gtg gcc aaa gag ttt gag    1248
Ser Thr Val Ser Pro Val Ser Glu Arg Pro Val Ala Lys Glu Phe Glu
                405                 410                 415 aat tgc tcc ctg gac gac cta cag ctg gtc acc act ctg ggc atg gga    1296
Asn Cys Ser Leu Asp Asp Leu Gln Leu Val Thr Thr Leu Gly Met Gly
            420                 425                 430 ggc ttc gga cgt gtt gag ctg gtt cag ctg agt aaa gaa aag ggc aaa    1344
Gly Phe Gly Arg Val Glu Leu Val Gln Leu Ser Lys Glu Lys Gly Lys
        435                 440                 445 acg ttc gcc ctg aaa tgt ctg aag aag aag cac atc gtg gag acg agg    1392
Thr Phe Ala Leu Lys Cys Leu Lys Lys Lys His Ile Val Glu Thr Arg
    450                 455                 460 cag cag gag cac atc tac tcg gag aag aag atc atg atg gag gcg gac    1440
Gln Gln Glu His Ile Tyr Ser Glu Lys Lys Ile Met Met Glu Ala Asp
465                 470                 475                 480 tct cct ttc ata acg aag ctc cac aag acc ttc cgc gac cgg aag tac    1488
Ser Pro Phe Ile Thr Lys Leu His Lys Thr Phe Arg Asp Arg Lys Tyr
                485                 490                 495 gtg tac atg ttg atg gag gtg tgt ctg ggc ggg gag ctg tgg acc att    1536
Val Tyr Met Leu Met Glu Val Cys Leu Gly Gly Glu Leu Trp Thr Ile
            500                 505                 510 ctc aga gac agg ggt aac ttt gac gac ttg acg gca agg ttc tgc gtc    1584
Leu Arg Asp Arg Gly Asn Phe Asp Asp Leu Thr Ala Arg Phe Cys Val
        515                 520                 525 gcc tgt gtg tta gag gct ttc tcc tac ctg cat gcc aaa gga atc att    1632
Ala Cys Val Leu Glu Ala Phe Ser Tyr Leu His Ala Lys Gly Ile Ile
```

```
tac agg gat ctc aaa cca gaa aat ctt cta ctg gac gcg agg gga tac    1680
Tyr Arg Asp Leu Lys Pro Glu Asn Leu Leu Leu Asp Ala Arg Gly Tyr
545                 550                 555                 560 gtc aaa ttg gtg gac ttc ggg ttc gcc aag aag atc ggc gtg ggg aag    1728
Val Lys Leu Val Asp Phe Gly Phe Ala Lys Lys Ile Gly Val Gly Lys
                565                 570                 575 aag acg tgg aca ttc tgc ggc acg ccg gag tac gtc gct ccg gag atc    1776
Lys Thr Trp Thr Phe Cys Gly Thr Pro Glu Tyr Val Ala Pro Glu Ile
            580                 585                 590 att ctc aac aag ggc cac gac cac tcg gcc gac tac tgg tcg ctg ggt    1824
Ile Leu Asn Lys Gly His Asp His Ser Ala Asp Tyr Trp Ser Leu Gly
        595                 600                 605 atc ctc atg tat gag ctg ctc aat gga acg ccc ccg ttc tcc ggg tca    1872
Ile Leu Met Tyr Glu Leu Leu Asn Gly Thr Pro Pro Phe Ser Gly Ser
    610                 615                 620 gat cct atg cgg acg tac aac atc att ctg aag ggc atc gac cac att    1920
Asp Pro Met Arg Thr Tyr Asn Ile Ile Leu Lys Gly Ile Asp His Ile
625                 630                 635                 640 gaa ttc ccc aag aaa att agc cgc agt gca cat gta ctt atc aag aaa    1968
Glu Phe Pro Lys Lys Ile Ser Arg Ser Ala His Val Leu Ile Lys Lys
                645                 650                 655 ctg tgc cga gac aac ccc atg gaa cga ctg gga tat ggg aag aat gga    2016
Leu Cys Arg Asp Asn Pro Met Glu Arg Leu Gly Tyr Gly Lys Asn Gly
            660                 665                 670 atc agt gac att agg aag aat aag tgg ttc caa ggc ttt gac tgg gat    2064
Ile Ser Asp Ile Arg Lys Asn Lys Trp Phe Gln Gly Phe Asp Trp Asp
        675                 680                 685 gga tta atg gat ctg acc ctc act cct cca att gtg ccc aag gtg aaa    2112
Gly Leu Met Asp Leu Thr Leu Thr Pro Pro Ile Val Pro Lys Val Lys
    690                 695                 700 aat cct aca gat aca agt aac ttc gat tcc tac ccc cgc gac atg gat    2160
Asn Pro Thr Asp Thr Ser Asn Phe Asp Ser Tyr Pro Arg Asp Met Asp
705                 710                 715                 720 ata gct gca gac gag tta tcc ggc tgg gac att gat ttc tga            2202
Ile Ala Ala Asp Glu Leu Ser Gly Trp Asp Ile Asp Phe
                725                 730
```

<210> SEQ ID NO 10
<211> LENGTH: 733
<212> TYPE: PRT
<213> ORGANISM: Aplysia californica

<400> SEQUENCE: 10

```
Met Gly Asn Gly Ala Ser Ser Asn Thr His Phe Thr Ile Asp Gly Glu
1               5                   10                  15

Ser Met Asp Val His Lys Val Lys Ala Leu Val Pro Glu Leu Arg His
            20                  25                  30

Glu Leu Arg Arg Arg Asp Lys Ile Ile Glu Gln Tyr Asp Ser Gln Val
        35                  40                  45

Arg Gln Lys Asp Glu Leu Leu Lys Glu Lys Glu Ala Glu Ile Ala Arg
    50                  55                  60

Leu Lys Glu Glu Val His Lys Leu Lys Ser Val Leu Gln Leu Lys Val
65                  70                  75                  80

Asp Thr Leu Lys Ala Gln Glu Ser Lys Pro Asp Leu Leu Ser Thr Ile
                85                  90                  95

Asp Glu Asn Gln Ala Glu Pro Thr Ala Pro Arg Gly Pro Ala Lys Lys
            100                 105                 110

Gln Gly Val Ser Gly Glu Ser Pro Ser Ser Lys Thr Leu Gly Tyr Val
```

```
                115              120              125
Asp Leu Thr His His Glu Lys Asp Phe Lys Ser Lys Gln Leu Ile Lys
130                 135                 140

Asp Ala Ile Leu Ser Asn Glu Phe Ile Lys Val Leu Ala Ala Thr Gln
145                 150                 155                 160

Leu Arg Glu Ile Ile Asp Cys Met Tyr Glu Lys Arg Val Pro Lys Ala
                165                 170                 175

Cys Tyr Ile Ile Lys Gly Gly Glu Arg Gly His Leu Tyr Val Cys
                180                 185                 190

Ala Asp Gly Leu Leu Glu Val His Lys Glu Asp Lys Arg Leu Gly Glu
                195                 200                 205

Ile Lys Ser Gly Gly Leu Phe Gly Glu Leu Ala Ile Leu Tyr Asn Cys
210                 215                 220

Lys Arg Thr Ala Ser Val Lys Ala Val Thr His Thr Thr Leu Trp Val
225                 230                 235                 240

Leu Asp Arg Arg Val Phe Gln Ala Ile Met Met Lys Thr Gly Leu Gln
                245                 250                 255

Arg Arg Glu Glu Asn Met Ala Phe Leu Lys Ser Val Pro Leu Leu Lys
                260                 265                 270

Asn Leu Pro Ser Asp Lys Leu Ala Lys Met Ser Asp Val Leu Glu Tyr
                275                 280                 285

Asp Phe His Glu Asn Glu Tyr Ile Ile Arg Glu Gly Ala Ala Gly
290                 295                 300

Asp Thr Phe Phe Ile Leu Asn Lys Gly Glu Val Lys Val Thr Gln Lys
305                 310                 315                 320

Ile Ala Gly His Ala Glu Pro Lys Glu Val Arg Arg Leu Lys Arg Gly
                325                 330                 335

Asp Tyr Phe Gly Glu Lys Ala Leu Leu Ser Glu Asp Arg Arg Thr Ala
                340                 345                 350

Asn Val Ile Ala Leu Pro Pro Gly Val Glu Cys Leu Thr Val Asp Arg
                355                 360                 365

Glu Ser Phe Thr Gln Phe Val Gly Asp Leu Asn Glu Leu Arg Asn Lys
370                 375                 380

Asp Tyr Gly Asp Glu Ala Arg Gly Ala Glu Arg Arg Ser Gly Ser Asp
385                 390                 395                 400

Ser Thr Val Ser Pro Val Ser Glu Arg Pro Val Ala Lys Glu Phe Glu
                405                 410                 415

Asn Cys Ser Leu Asp Asp Leu Gln Leu Val Thr Thr Leu Gly Met Gly
                420                 425                 430

Gly Phe Gly Arg Val Glu Leu Val Gln Leu Ser Lys Glu Lys Gly Lys
                435                 440                 445

Thr Phe Ala Leu Lys Cys Leu Lys Lys His Ile Val Glu Thr Arg
450                 455                 460

Gln Gln Glu His Ile Tyr Ser Lys Lys Ile Met Met Glu Ala Asp
465                 470                 475                 480

Ser Pro Phe Ile Thr Lys Leu His Lys Thr Phe Arg Asp Arg Lys Tyr
                485                 490                 495

Val Tyr Met Leu Met Glu Val Cys Leu Gly Gly Glu Leu Trp Thr Ile
                500                 505                 510

Leu Arg Asp Arg Gly Asn Phe Asp Asp Leu Thr Ala Arg Phe Cys Val
                515                 520                 525

Ala Cys Val Leu Glu Ala Phe Ser Tyr Leu His Ala Lys Gly Ile Ile
530                 535                 540
```

Tyr Arg Asp Leu Lys Pro Glu Asn Leu Leu Asp Ala Arg Gly Tyr
545                 550                 555                 560

Val Lys Leu Val Asp Phe Gly Phe Ala Lys Ile Gly Val Gly Lys
            565                 570                 575

Lys Thr Trp Thr Phe Cys Gly Thr Pro Glu Tyr Val Ala Pro Glu Ile
        580                 585                 590

Ile Leu Asn Lys Gly His Asp His Ser Ala Asp Tyr Trp Ser Leu Gly
            595                 600                 605

Ile Leu Met Tyr Glu Leu Leu Asn Gly Thr Pro Pro Phe Ser Gly Ser
        610                 615                 620

Asp Pro Met Arg Thr Tyr Asn Ile Ile Leu Lys Gly Ile Asp His Ile
625                 630                 635                 640

Glu Phe Pro Lys Lys Ile Ser Arg Ser Ala His Val Leu Ile Lys Lys
                645                 650                 655

Leu Cys Arg Asp Asn Pro Met Glu Arg Leu Gly Tyr Gly Lys Asn Gly
            660                 665                 670

Ile Ser Asp Ile Arg Lys Asn Lys Trp Phe Gln Gly Phe Asp Trp Asp
        675                 680                 685

Gly Leu Met Asp Leu Thr Leu Thr Pro Pro Ile Val Pro Lys Val Lys
        690                 695                 700

Asn Pro Thr Asp Thr Ser Asn Phe Asp Ser Tyr Pro Arg Asp Met Asp
705                 710                 715                 720

Ile Ala Ala Asp Glu Leu Ser Gly Trp Asp Ile Asp Phe
            725                 730

<210> SEQ ID NO 11
<211> LENGTH: 72
<212> TYPE: DNA
<213> ORGANISM: artificial sequence
<220> FEATURE:
<223> OTHER INFORMATION: synthetic oligonucleotide

<400> SEQUENCE: 11
tggcggccgc tcatgagagg atcgcatcac catcaccatc acggcaacgg tgccagttcg        60
aacacgcact tc                                                            72

<210> SEQ ID NO 12
<211> LENGTH: 42
<212> TYPE: DNA
<213> ORGANISM: artificial sequence
<220> FEATURE:
<223> OTHER INFORMATION: synthetic oligonucleotide

<400> SEQUENCE: 12
gcaggctcta gagaaatcaa tgtcccagcc ggataactcg tc                           42

<210> SEQ ID NO 13
<211> LENGTH: 38
<212> TYPE: DNA
<213> ORGANISM: artificial sequence
<220> FEATURE:
<223> OTHER INFORMATION: synthetic oligonucleotide

<400> SEQUENCE: 13
gtcgtgggat ccccatcgat agcgagacgg tcatctgt                                38

<210> SEQ ID NO 14
<211> LENGTH: 37
<212> TYPE: DNA
<213> ORGANISM: artificial sequence
<220> FEATURE:

```
<223> OTHER INFORMATION: synthetic oligonucleotide

<400> SEQUENCE: 14
atcttgaatt cctcgagggt caaggagaac cccgctt                          37

<210> SEQ ID NO 15
<211> LENGTH: 20
<212> TYPE: DNA
<213> ORGANISM: artificial sequence
<220> FEATURE:
<223> OTHER INFORMATION: synthetic oligonucleotide

<400> SEQUENCE: 15
gtaccctcac aggacgagtc                                             20

<210> SEQ ID NO 16
<211> LENGTH: 20
<212> TYPE: DNA
<213> ORGANISM: artificial sequence
<220> FEATURE:
<223> OTHER INFORMATION: synthetic oligonucleotide

<400> SEQUENCE: 16
tccttggacc tctcttggtg                                             20

<210> SEQ ID NO 17
<211> LENGTH: 20
<212> TYPE: DNA
<213> ORGANISM: artificial sequence
<220> FEATURE:
<223> OTHER INFORMATION: synthetic oligonucleotide

<400> SEQUENCE: 17
aacagaaaca gtctttcccc                                             20

<210> SEQ ID NO 18
<211> LENGTH: 19
<212> TYPE: DNA
<213> ORGANISM: artificial sequence
<220> FEATURE:
<223> OTHER INFORMATION: synthetic oligonucleotide

<400> SEQUENCE: 18
tcttgactca ccaactgcc                                              19

<210> SEQ ID NO 19
<211> LENGTH: 19
<212> TYPE: DNA
<213> ORGANISM: artificial sequence
<220> FEATURE:
<223> OTHER INFORMATION: synthetic oligonucleotide

<400> SEQUENCE: 19
cagagagaag atgacccag                                              19

<210> SEQ ID NO 20
<211> LENGTH: 20
<212> TYPE: DNA
<213> ORGANISM: artificial sequence
<220> FEATURE:
<223> OTHER INFORMATION: synthetic oligonucleotide

<400> SEQUENCE: 20
gggtaagaga agcaagaaag                                             20

<210> SEQ ID NO 21
```

-continued

```
<211> LENGTH: 8
<212> TYPE: PRT
<213> ORGANISM: artificial sequence
<220> FEATURE:
<223> OTHER INFORMATION: synthetic peptide

<400> SEQUENCE: 21

Arg Lys Ile Ser Ala Ser Gly Pro
1               5

<210> SEQ ID NO 22
<211> LENGTH: 13
<212> TYPE: PRT
<213> ORGANISM: artificial sequence
<220> FEATURE:
<223> OTHER INFORMATION: synthetic peptide

<400> SEQUENCE: 22

Arg Lys Ile Ser Ala Ser Glu Phe Asp Arg Pro Leu Arg
1               5                   10

<210> SEQ ID NO 23
<211> LENGTH: 7
<212> TYPE: PRT
<213> ORGANISM: artificial sequence
<220> FEATURE:
<223> OTHER INFORMATION: synthetic peptide

<400> SEQUENCE: 23

Arg Lys Arg Ser Arg Ala Glu
1               5

<210> SEQ ID NO 24
<211> LENGTH: 10
<212> TYPE: PRT
<213> ORGANISM: artificial sequence
<220> FEATURE:
<223> OTHER INFORMATION: synthetic peptide

<400> SEQUENCE: 24

Gln Lys Arg Pro Arg Arg Lys Asp Thr Pro
1               5                   10

<210> SEQ ID NO 25
<211> LENGTH: 272
<212> TYPE: PRT
<213> ORGANISM: Aplysia californica

<400> SEQUENCE: 25

Val Ala Lys Glu Phe Glu Asn Cys Ser Leu Asp Asp Leu Gln Leu Val
1               5                   10                  15

Thr Thr Leu Gly Met Gly Gly Phe Gly Arg Val Glu Leu Val Gln Leu
            20                  25                  30

Ser Lys Glu Lys Gly Lys Thr Phe Ala Leu Lys Cys Leu Lys Lys Lys
        35                  40                  45

His Ile Val Glu Thr Arg Gln Gln Glu His Ile Tyr Ser Glu Lys Lys
    50                  55                  60

Ile Met Met Glu Ala Asp Ser Pro Phe Ile Thr Lys Leu His Lys Thr
65                  70                  75                  80

Phe Arg Asp Arg Lys Tyr Val Tyr Met Leu Met Glu Val Cys Leu Gly
                85                  90                  95

Gly Glu Leu Trp Thr Ile Leu Arg Asp Arg Gly Asn Phe Asp Asp Leu
            100                 105                 110

Thr Ala Arg Phe Cys Val Ala Cys Val Leu Glu Ala Phe Ser Tyr Leu
```

```
            115                 120                 125
His Ala Lys Gly Ile Ile Tyr Arg Asp Leu Lys Pro Glu Asn Leu Leu
    130                 135                 140

Leu Asp Ala Arg Gly Tyr Val Lys Leu Val Asp Phe Gly Phe Ala Lys
145                 150                 155                 160

Lys Ile Gly Val Gly Lys Lys Thr Trp Thr Phe Cys Gly Thr Pro Glu
                165                 170                 175

Tyr Val Ala Pro Glu Ile Ile Leu Asn Lys Gly His Asp His Ser Ala
            180                 185                 190

Asp Tyr Trp Ser Leu Gly Ile Leu Met Tyr Glu Leu Leu Asn Gly Thr
        195                 200                 205

Pro Pro Phe Ser Gly Ser Asp Pro Met Arg Thr Tyr Asn Ile Ile Leu
    210                 215                 220

Lys Gly Ile Asp His Ile Glu Phe Pro Lys Lys Ile Ser Arg Ser Ala
225                 230                 235                 240

His Val Leu Ile Lys Lys Leu Cys Arg Asp Asn Pro Met Glu Arg Leu
                245                 250                 255

Gly Tyr Gly Lys Asn Gly Ile Ser Asp Ile Arg Lys Asn Lys Trp Phe
            260                 265                 270

<210> SEQ ID NO 26
<211> LENGTH: 8
<212> TYPE: PRT
<213> ORGANISM: artificial sequence
<220> FEATURE:
<223> OTHER INFORMATION: synthetic peptide

<400> SEQUENCE: 26

Leu Arg Lys Lys Lys Lys Lys His
1               5

<210> SEQ ID NO 27
<211> LENGTH: 8
<212> TYPE: PRT
<213> ORGANISM: artificial sequence
<220> FEATURE:
<223> OTHER INFORMATION: synthetic peptide

<400> SEQUENCE: 27

Leu Arg Ala Lys Lys Lys Lys His
1               5

<210> SEQ ID NO 28
<211> LENGTH: 8
<212> TYPE: PRT
<213> ORGANISM: artificial sequence
<220> FEATURE:
<223> OTHER INFORMATION: synthetic peptide

<400> SEQUENCE: 28

Leu Arg Lys Ala Lys Lys Lys His
1               5

<210> SEQ ID NO 29
<211> LENGTH: 8
<212> TYPE: PRT
<213> ORGANISM: artificial sequence
<220> FEATURE:
<223> OTHER INFORMATION: synthetic peptide

<400> SEQUENCE: 29

Leu Arg Lys Lys Ala Lys Lys His
1               5
```

<210> SEQ ID NO 30
<211> LENGTH: 8
<212> TYPE: PRT
<213> ORGANISM: artificial sequence
<220> FEATURE:
<223> OTHER INFORMATION: synthetic peptide

<400> SEQUENCE: 30

Leu Arg Lys Lys Lys Ala Lys His
1               5

<210> SEQ ID NO 31
<211> LENGTH: 8
<212> TYPE: PRT
<213> ORGANISM: artificial sequence
<220> FEATURE:
<223> OTHER INFORMATION: synthetic peptide

<400> SEQUENCE: 31

Leu Arg Lys Lys Lys Lys Lys His
1               5

<210> SEQ ID NO 32
<211> LENGTH: 4
<212> TYPE: PRT
<213> ORGANISM: artificial sequence
<220> FEATURE:
<223> OTHER INFORMATION: synthetic peptide

<400> SEQUENCE: 32

Arg Lys Lys Lys
1

<210> SEQ ID NO 33
<211> LENGTH: 22
<212> TYPE: PRT
<213> ORGANISM: artificial sequence
<220> FEATURE:
<223> OTHER INFORMATION: synthetic peptide
<220> FEATURE:
<221> NAME/KEY: MISC_FEATURE
<222> LOCATION: (9)..(9)
<223> OTHER INFORMATION: Linker peptide delta from 0 to 100 residues

<400> SEQUENCE: 33

Leu Arg Lys Lys Lys Lys Lys His Xaa Tyr Gly Arg Lys Lys Arg Arg
1               5                   10                  15

Gln Arg Arg Pro Pro
            20

<210> SEQ ID NO 34
<211> LENGTH: 22
<212> TYPE: PRT
<213> ORGANISM: artificial sequence
<220> FEATURE:
<223> OTHER INFORMATION: synthetic peptide
<220> FEATURE:
<221> NAME/KEY: MISC_FEATURE
<222> LOCATION: (14)..(14)
<223> OTHER INFORMATION: Linker peptide delta from 0 to 100 residues

<400> SEQUENCE: 34

Tyr Gly Arg Lys Lys Arg Arg Gln Arg Arg Pro Pro Xaa Leu Arg
1               5                   10                  15

Lys Lys Lys Lys Lys His
            20

```
<210> SEQ ID NO 35
<211> LENGTH: 25
<212> TYPE: PRT
<213> ORGANISM: artificial sequence
<220> FEATURE:
<223> OTHER INFORMATION: synthetic peptide
<220> FEATURE:
<221> NAME/KEY: MISC_FEATURE
<222> LOCATION: (9)..(9)
<223> OTHER INFORMATION: Linker peptide delta from 0 to 100 residues

<400> SEQUENCE: 35

Leu Arg Lys Lys Lys Lys Lys His Xaa Arg Gln Ile Lys Ile Trp Phe
1               5                   10                  15

Gln Asn Arg Arg Met Lys Trp Lys Lys
            20                  25

<210> SEQ ID NO 36
<211> LENGTH: 25
<212> TYPE: PRT
<213> ORGANISM: artificial sequence
<220> FEATURE:
<223> OTHER INFORMATION: synthetic peptide
<220> FEATURE:
<221> NAME/KEY: MISC_FEATURE
<222> LOCATION: (17)..(17)
<223> OTHER INFORMATION: Linker peptide delta from 0 to 100 residues

<400> SEQUENCE: 36

Arg Gln Ile Lys Ile Trp Phe Gln Asn Arg Arg Met Lys Trp Lys Lys
1               5                   10                  15

Xaa Leu Arg Lys Lys Lys Lys Lys His
            20                  25

<210> SEQ ID NO 37
<211> LENGTH: 15
<212> TYPE: PRT
<213> ORGANISM: artificial sequence
<220> FEATURE:
<223> OTHER INFORMATION: synthetic peptide
<220> FEATURE:
<221> NAME/KEY: MISC_FEATURE
<222> LOCATION: (9)..(9)
<223> OTHER INFORMATION: Linker peptide epsilon from 0 to 100 residues

<400> SEQUENCE: 37

Leu Arg Lys Lys Lys Lys Lys His Xaa Pro Lys Lys Lys Arg Lys
1               5                   10                  15

<210> SEQ ID NO 38
<211> LENGTH: 15
<212> TYPE: PRT
<213> ORGANISM: artificial sequence
<220> FEATURE:
<223> OTHER INFORMATION: synthetic peptide
<220> FEATURE:
<221> NAME/KEY: MISC_FEATURE
<222> LOCATION: (7)..(7)
<223> OTHER INFORMATION: Linker peptide epsilon from 0 to 100 residues

<400> SEQUENCE: 38

Pro Lys Lys Lys Arg Lys Xaa Leu Arg Lys Lys Lys Lys Lys His
1               5                   10                  15

<210> SEQ ID NO 39
<211> LENGTH: 29
<212> TYPE: PRT
<213> ORGANISM: artificial sequence
<220> FEATURE:
```

<223> OTHER INFORMATION: synthetic peptide
<220> FEATURE:
<221> NAME/KEY: MISC_FEATURE
<222> LOCATION: (14)..(14)
<223> OTHER INFORMATION: Linker peptide delta from 0 to 100 residues
<220> FEATURE:
<221> NAME/KEY: MISC_FEATURE
<222> LOCATION: (23)..(23)
<223> OTHER INFORMATION: Linker peptide epsilon from 0 to 100 residues

<400> SEQUENCE: 39

Tyr Gly Arg Lys Lys Arg Arg Gln Arg Arg Pro Pro Xaa Leu Arg
1               5                   10                  15

Lys Lys Lys Lys Lys His Xaa Pro Lys Lys Lys Arg Lys
            20                  25

<210> SEQ ID NO 40
<211> LENGTH: 29
<212> TYPE: PRT
<213> ORGANISM: artificial sequence
<220> FEATURE:
<223> OTHER INFORMATION: synthetic peptide
<220> FEATURE:
<221> NAME/KEY: MISC_FEATURE
<222> LOCATION: (7)..(7)
<223> OTHER INFORMATION: Linker peptide epsilon from 0 to 100 residues
<220> FEATURE:
<221> NAME/KEY: MISC_FEATURE
<222> LOCATION: (16)..(16)
<223> OTHER INFORMATION: Linker peptide delta from 0 to 100 residues

<400> SEQUENCE: 40

Pro Lys Lys Lys Arg Lys Xaa Leu Arg Lys Lys Lys Lys Lys His Xaa
1               5                   10                  15

Tyr Gly Arg Lys Lys Arg Arg Gln Arg Arg Pro Pro
            20                  25

<210> SEQ ID NO 41
<211> LENGTH: 32
<212> TYPE: PRT
<213> ORGANISM: artificial sequence
<220> FEATURE:
<223> OTHER INFORMATION: synthetic peptide
<220> FEATURE:
<221> NAME/KEY: MISC_FEATURE
<222> LOCATION: (17)..(17)
<223> OTHER INFORMATION: Linker peptide delta from 0 to 100 residues
<220> FEATURE:
<221> NAME/KEY: MISC_FEATURE
<222> LOCATION: (26)..(26)
<223> OTHER INFORMATION: Linker peptide epsilon from 0 to 100 residues

<400> SEQUENCE: 41

Arg Gln Ile Lys Ile Trp Phe Gln Asn Arg Arg Met Lys Trp Lys Lys
1               5                   10                  15

Xaa Leu Arg Lys Lys Lys Lys Lys His Xaa Pro Lys Lys Lys Arg Lys
            20                  25                  30

<210> SEQ ID NO 42
<211> LENGTH: 32
<212> TYPE: PRT
<213> ORGANISM: artificial sequence
<220> FEATURE:
<223> OTHER INFORMATION: synthetic peptide
<220> FEATURE:
<221> NAME/KEY: MISC_FEATURE
<222> LOCATION: (7)..(7)
<223> OTHER INFORMATION: Linker peptide epsilon from 0 to 100 residues
<220> FEATURE:
<221> NAME/KEY: MISC_FEATURE
<222> LOCATION: (16)..(16)

<223> OTHER INFORMATION: Linker peptide delta from 0 to 100 residues

<400> SEQUENCE: 42

Pro Lys Lys Lys Arg Lys Xaa Leu Arg Lys Lys Lys Lys His Xaa
1               5                   10                  15
Arg Gln Ile Lys Ile Trp Phe Gln Asn Arg Arg Met Lys Trp Lys Lys
            20                  25                  30

<210> SEQ ID NO 43
<211> LENGTH: 13
<212> TYPE: PRT
<213> ORGANISM: artificial sequence
<220> FEATURE:
<223> OTHER INFORMATION: synthetic peptide

<400> SEQUENCE: 43

Tyr Gly Arg Lys Lys Arg Arg Gln Arg Arg Pro Pro
1               5                   10

<210> SEQ ID NO 44
<211> LENGTH: 9
<212> TYPE: PRT
<213> ORGANISM: artificial sequence
<220> FEATURE:
<223> OTHER INFORMATION: synthetic peptide

<400> SEQUENCE: 44

Arg Lys Lys Arg Arg Gln Arg Arg Arg
1               5

<210> SEQ ID NO 45
<211> LENGTH: 16
<212> TYPE: PRT
<213> ORGANISM: artificial sequence
<220> FEATURE:
<223> OTHER INFORMATION: synthetic peptide

<400> SEQUENCE: 45

Arg Gln Ile Lys Ile Trp Phe Gln Asn Arg Arg Met Lys Trp Lys Lys
1               5                   10                  15

<210> SEQ ID NO 46
<211> LENGTH: 6
<212> TYPE: PRT
<213> ORGANISM: artificial sequence
<220> FEATURE:
<223> OTHER INFORMATION: synthetic peptide

<400> SEQUENCE: 46

Pro Lys Lys Lys Arg Lys
1               5

<210> SEQ ID NO 47
<211> LENGTH: 10
<212> TYPE: PRT
<213> ORGANISM: artificial sequence
<220> FEATURE:
<223> OTHER INFORMATION: synthetic peptide

<400> SEQUENCE: 47

Cys Thr Pro Pro Lys Lys Lys Arg Lys Val
1               5                   10

<210> SEQ ID NO 48
<211> LENGTH: 5
<212> TYPE: PRT
<213> ORGANISM: artificial sequence

```
<220> FEATURE:
<223> OTHER INFORMATION: synthetic peptide

<400> SEQUENCE: 48

Lys Lys Lys Arg Lys
1               5

<210> SEQ ID NO 49
<211> LENGTH: 7
<212> TYPE: PRT
<213> ORGANISM: artificial sequence
<220> FEATURE:
<223> OTHER INFORMATION: synthetic peptide

<400> SEQUENCE: 49

Pro Pro Lys Lys Lys Arg Lys
1               5

<210> SEQ ID NO 50
<211> LENGTH: 8
<212> TYPE: PRT
<213> ORGANISM: artificial sequence
<220> FEATURE:
<223> OTHER INFORMATION: synthetic peptide

<400> SEQUENCE: 50

Thr Pro Pro Lys Lys Lys Arg Lys
1               5

<210> SEQ ID NO 51
<211> LENGTH: 8
<212> TYPE: PRT
<213> ORGANISM: artificial sequence
<220> FEATURE:
<223> OTHER INFORMATION: synthetic peptide

<400> SEQUENCE: 51

Pro Lys Lys Lys Lys Arg Lys Val
1               5

<210> SEQ ID NO 52
<211> LENGTH: 768
<212> TYPE: PRT
<213> ORGANISM: Drosophila melanogaster

<400> SEQUENCE: 52

Met Ala Ala Gly Met Leu Thr Asp Arg Glu Arg Glu Ala Ile Val Ser
1               5                   10                  15

Asn Leu Thr Lys Asp Val Gln Ala Leu Arg Glu Met Val Arg Ser Arg
                20                  25                  30

Glu Ser Glu Leu Val Lys Leu His Arg Glu Ile His Lys Leu Lys Ser
            35                  40                  45

Val Leu Gln Gln Thr Thr Asn Asn Leu Asn Val Thr Arg Asn Glu Lys
        50                  55                  60

Ala Lys Lys Lys Leu Tyr Ser Leu Pro Glu Gln Cys Gly Glu Gln Glu
65                  70                  75                  80

Ser Arg Asn Gln Asn Pro His Leu Cys Ser Ser Cys Gly Met Val Leu
                85                  90                  95

Pro Thr Ser Pro Glu Phe Ala Leu Glu Ala Leu Ser Leu Gly Pro Leu
                100                 105                 110

Ser Pro Leu Ala Ser Thr Ser Ser Ala Ser Pro Ser Gly Arg Thr Ser
            115                 120                 125

Ala Asp Glu Val Arg Pro Lys Ala Met Pro Ala Ala Ile Lys Lys Gln
```

```
                    130                 135                 140
Gly Val Ser Ala Glu Ser Cys Val Gln Ser Met Gln Gln Ser Tyr Ser
145                 150                 155                 160

Ile Pro Ile Pro Lys Tyr Glu Lys Asp Phe Ser Asp Lys Gln Gln Ile
                165                 170                 175

Lys Asp Ala Ile Met Asp Asn Asp Phe Leu Lys Asn Ile Asp Ala Ser
                180                 185                 190

Gln Val Arg Glu Leu Val Asp Ser Met Tyr Ser Lys Ser Ile Ala Ala
                195                 200                 205

Gly Glu Phe Val Ile Arg Glu Gly Val Gly Ala His Leu Tyr Val
                210                 215                 220

Ser Ala Ala Gly Glu Phe Ala Val Met Gln His Gly Lys Val Leu Asp
225                 230                 235                 240

Lys Met Gly Ala Gly Lys Ala Phe Gly Glu Leu Ala Ile Leu Tyr Asn
                245                 250                 255

Cys Thr Arg Thr Ala Ser Ile Arg Val Leu Ser Glu Ala Ala Arg Val
                260                 265                 270

Trp Val Leu Asp Arg Arg Val Phe Gln Gln Ile Met Met Cys Thr Gly
                275                 280                 285

Leu Gln Arg Ile Glu Asn Ser Val Asn Phe Leu Arg Ser Val Pro Leu
                290                 295                 300

Leu Met Asn Leu Ser Glu Leu Leu Ala Lys Ile Ala Asp Val Leu
305                 310                 315                 320

Glu Leu Glu Phe Tyr Ala Ala Gly Thr Tyr Ile Ile Arg Gln Gly Thr
                325                 330                 335

Ala Gly Asp Ser Phe Phe Leu Ile Ser Gln Gly Asn Val Arg Val Thr
                340                 345                 350

Gln Lys Leu Thr Pro Thr Ser Pro Glu Glu Thr Glu Leu Arg Thr Leu
                355                 360                 365

Ser Arg Gly Asp Tyr Phe Gly Glu Gln Ala Leu Ile Asn Glu Asp Lys
                370                 375                 380

Arg Thr Ala Asn Ile Ile Ala Leu Ser Pro Gly Val Glu Cys Leu Thr
385                 390                 395                 400

Leu Asp Arg Asp Ser Phe Lys Arg Leu Ile Gly Asp Leu Cys Glu Leu
                405                 410                 415

Lys Glu Lys Asp Tyr Gly Asp Glu Ser Arg Lys Leu Ala Met Lys Gln
                420                 425                 430

Ala Arg Glu Ser Cys Gln Asp Glu Pro Lys Glu Gln Leu Gln Gln Glu
                435                 440                 445

Phe Pro Asp Leu Lys Leu Thr Asp Leu Glu Val Val Ser Thr Leu Gly
450                 455                 460

Ile Gly Gly Phe Gly Arg Val Glu Leu Val Lys Ala His His Gln Asp
465                 470                 475                 480

Arg Val Asp Ile Phe Ala Leu Lys Cys Leu Lys Lys Arg His Ile Val
                485                 490                 495

Asp Thr Lys Gln Glu Glu His Ile Phe Ser Glu Arg His Ile Met Leu
                500                 505                 510

Ser Ser Arg Ser Pro Phe Ile Cys Arg Leu Tyr Arg Thr Phe Arg Asp
                515                 520                 525

Glu Lys Tyr Val Tyr Met Leu Leu Glu Ala Cys Met Gly Gly Glu Ile
                530                 535                 540

Trp Thr Met Leu Arg Asp Arg Gly Ser Phe Glu Asp Asn Ala Ala Gln
545                 550                 555                 560
```

Phe Ile Ile Gly Cys Val Leu Gln Ala Phe Glu Tyr Leu His Ala Arg
                565                 570                 575

Gly Ile Ile Tyr Arg Asp Leu Lys Pro Glu Asn Leu Met Leu Asp Glu
            580                 585                 590

Arg Gly Tyr Val Lys Ile Val Asp Phe Gly Phe Ala Lys Gln Ile Gly
        595                 600                 605

Thr Ser Ser Lys Thr Trp Thr Phe Cys Gly Thr Pro Glu Tyr Val Ala
    610                 615                 620

Pro Glu Ile Ile Leu Asn Lys Gly His Asp Arg Ala Val Asp Tyr Trp
625                 630                 635                 640

Ala Leu Gly Ile Leu Ile His Glu Leu Leu Asn Gly Thr Pro Pro Phe
                645                 650                 655

Ser Ala Pro Asp Pro Met Gln Thr Tyr Asn Leu Ile Leu Lys Gly Ile
            660                 665                 670

Asp Met Ile Ala Phe Pro Lys His Ile Ser Arg Trp Ala Val Gln Leu
        675                 680                 685

Ile Lys Arg Leu Cys Arg Asp Val Pro Ser Glu Arg Leu Gly Tyr Gln
    690                 695                 700

Thr Gly Gly Ile Gln Asp Ile Lys Lys His Lys Trp Phe Leu Gly Phe
705                 710                 715                 720

Asp Trp Asp Gly Leu Ala Ser Gln Leu Leu Ile Pro Pro Phe Val Arg
                725                 730                 735

Pro Ile Ala His Pro Thr Asp Val Arg Tyr Phe Asp Arg Phe Pro Cys
            740                 745                 750

Asp Leu Asn Glu Pro Pro Asp Leu Ser Gly Trp Asp Ala Asp Phe
        755                 760                 765

<210> SEQ ID NO 53
<211> LENGTH: 742
<212> TYPE: PRT
<213> ORGANISM: Drosophila melanogaster

<400> SEQUENCE: 53

Met Gln Ser Leu Arg Ile Ser Gly Cys Thr Pro Ser Gly Thr Gly Gly
1               5                   10                  15

Ser Ala Thr Pro Ser Pro Val Gly Leu Val Asp Pro Asn Phe Ile Val
            20                  25                  30

Ser Asn Tyr Val Ala Ala Ser Pro Gln Glu Arg Phe Ile Gln Ile
        35                  40                  45

Ile Gln Ala Lys Glu Leu Lys Ile Gln Glu Met Gln Arg Ala Leu Gln
    50                  55                  60

Phe Lys Asp Asn Glu Ile Ala Glu Leu Lys Ser His Leu Asp Lys Phe
65                  70                  75                  80

Gln Ser Val Phe Pro Phe Ser Arg Gly Ser Ala Ala Gly Cys Ala Gly
                85                  90                  95

Thr Gly Gly Ala Ser Gly Ser Gly Ala Gly Gly Ser Gly Gly Ser Gly
            100                 105                 110

Pro Gly Thr Ala Thr Gly Ala Thr Arg Lys Ser Gly Gln Asn Phe Gln
        115                 120                 125

Arg Gln Arg Ala Leu Gly Ile Ser Ala Glu Pro Gln Ser Glu Ser Ser
    130                 135                 140

Leu Leu Leu Glu His Val Ser Phe Pro Lys Tyr Asp Lys Asp Glu Arg
145                 150                 155                 160

Ser Arg Glu Leu Ile Lys Ala Ile Leu Asp Asn Asp Phe Met Lys
                165                 170                 175

-continued

Asn Leu Asp Leu Thr Gln Ile Arg Glu Ile Val Asp Cys Met Tyr Pro
            180                 185                 190

Val Lys Tyr Pro Ala Lys Asn Leu Ile Ile Lys Glu Gly Asp Val Gly
        195                 200                 205

Ser Ile Val Tyr Val Met Glu Asp Gly Arg Val Glu Val Ser Arg Glu
210                 215                 220

Gly Lys Tyr Leu Ser Thr Leu Ser Gly Ala Lys Val Leu Gly Glu Leu
225                 230                 235                 240

Ala Ile Leu Tyr Asn Cys Gln Arg Thr Ala Thr Ile Thr Ala Ile Thr
                245                 250                 255

Glu Cys Asn Leu Trp Ala Ile Glu Arg Gln Cys Phe Gln Thr Ile Met
            260                 265                 270

Met Arg Thr Gly Leu Ile Arg Gln Ala Glu Tyr Ser Asp Phe Leu Lys
        275                 280                 285

Ser Val Pro Ile Phe Lys Asp Leu Ala Glu Asp Thr Leu Ile Lys Ile
290                 295                 300

Ser Asp Val Leu Glu Glu Thr His Tyr Gln Arg Gly Asp His Ile Val
305                 310                 315                 320

Arg Gln Gly Ala Arg Gly Asp Thr Phe Phe Ile Ile Ser Lys Gly Lys
                325                 330                 335

Val Arg Val Thr Ile Lys Gln Gln Asp Arg Gln Glu Glu Lys Phe Ile
            340                 345                 350

Arg Met Leu Gly Lys Gly Asp Phe Phe Gly Glu Lys Ala Leu Gln Gly
        355                 360                 365

Asp Asp Leu Arg Thr Ala Asn Ile Ile Cys Glu Ser Ala Asp Gly Val
370                 375                 380

Ser Cys Leu Val Ile Asp Arg Glu Thr Phe Asn Gln Leu Ile Ser Asn
385                 390                 395                 400

Leu Asp Glu Ile Lys His Arg Tyr Asp Asp Glu Gly Ala Met Glu Arg
                405                 410                 415

Arg Lys Ile Asn Glu Glu Phe Arg Asp Ile Asn Leu Thr Asp Leu Arg
            420                 425                 430

Val Ile Ala Thr Leu Gly Val Gly Gly Phe Gly Arg Val Glu Leu Val
        435                 440                 445

Gln Thr Asn Gly Asp Ser Ser Arg Ser Phe Ala Leu Lys Gln Met Lys
450                 455                 460

Lys Ser Gln Ile Val Glu Thr Arg Gln Gln His Ile Met Ser Glu
465                 470                 475                 480

Lys Glu Ile Met Gly Glu Ala Asn Cys Gln Phe Ile Val Lys Leu Phe
                485                 490                 495

Lys Thr Phe Lys Asp Lys Lys Tyr Leu Tyr Met Leu Met Glu Ser Cys
            500                 505                 510

Leu Gly Gly Glu Leu Trp Thr Ile Leu Arg Asp Lys Gly Asn Phe Asp
        515                 520                 525

Asp Ser Thr Thr Arg Phe Tyr Thr Ala Cys Val Val Glu Ala Phe Asp
530                 535                 540

Tyr Leu His Ser Arg Asn Ile Ile Tyr Arg Asp Leu Lys Pro Glu Asn
545                 550                 555                 560

Leu Leu Leu Asn Glu Arg Gly Tyr Gly Lys Leu Val Asp Phe Gly Phe
                565                 570                 575

Ala Lys Lys Leu Gln Thr Gly Arg Lys Thr Trp Thr Phe Cys Gly Thr
            580                 585                 590

Pro Glu Tyr Val Ala Pro Glu Val Ile Leu Asn Arg Gly His Asp Ile
        595                 600                 605

```
Ser Ala Asp Tyr Trp Ser Leu Gly Val Leu Met Phe Glu Leu Leu Thr
    610                 615                 620

Gly Thr Pro Pro Phe Thr Gly Ser Asp Pro Met Arg Thr Tyr Asn Ile
625                 630                 635                 640

Ile Leu Lys Gly Ile Asp Ala Ile Glu Phe Pro Arg Asn Ile Thr Arg
                645                 650                 655

Asn Ala Ser Asn Leu Ile Lys Lys Leu Cys Arg Asp Asn Pro Ala Glu
            660                 665                 670

Arg Leu Gly Tyr Gln Arg Gly Ile Ser Glu Ile Gln Lys His Lys
        675                 680                 685

Trp Phe Asp Gly Phe Tyr Trp Trp Gly Leu Gln Asn Cys Thr Leu Glu
690                 695                 700

Pro Pro Ile Lys Pro Ala Val Lys Ser Val Val Asp Thr Thr Asn Phe
705                 710                 715                 720

Asp Asp Tyr Pro Pro Asp Pro Glu Gly Pro Pro Asp Asp Val Thr
                725                 730                 735

Gly Trp Asp Lys Asp Phe
            740

<210> SEQ ID NO 54
<211> LENGTH: 671
<212> TYPE: PRT
<213> ORGANISM: Homo sapiens

<400> SEQUENCE: 54

Met Ser Glu Leu Glu Glu Asp Phe Ala Lys Ile Leu Met Leu Lys Glu
1               5                   10                  15

Glu Arg Ile Lys Glu Leu Glu Lys Arg Leu Ser Glu Lys Glu Glu Glu
            20                  25                  30

Ile Gln Glu Leu Lys Arg Lys Leu His Lys Cys Gln Ser Val Leu Pro
        35                  40                  45

Val Pro Ser Thr His Ile Gly Pro Arg Thr Thr Arg Ala Gln Gly Ile
    50                  55                  60

Ser Ala Glu Pro Gln Thr Tyr Arg Ser Phe His Asp Leu Arg Gln Ala
65                  70                  75                  80

Phe Arg Lys Phe Thr Lys Ser Glu Arg Ser Lys Asp Leu Ile Lys Glu
                85                  90                  95

Ala Ile Leu Asp Asn Asp Phe Met Lys Asn Leu Glu Leu Ser Gln Ile
            100                 105                 110

Gln Glu Ile Val Asp Cys Met Tyr Pro Val Glu Tyr Gly Lys Asp Ser
        115                 120                 125

Cys Ile Ile Lys Glu Gly Asp Val Gly Ser Leu Val Tyr Val Met Glu
    130                 135                 140

Asp Gly Lys Val Glu Val Thr Lys Glu Gly Val Lys Leu Cys Thr Met
145                 150                 155                 160

Gly Pro Gly Lys Val Phe Gly Glu Leu Ala Ile Leu Tyr Asn Cys Thr
                165                 170                 175

Arg Thr Ala Thr Val Lys Thr Leu Val Asn Val Lys Leu Trp Ala Ile
            180                 185                 190

Asp Arg Gln Cys Phe Gln Thr Ile Met Met Arg Thr Gly Leu Ile Lys
        195                 200                 205

His Thr Glu Tyr Met Glu Phe Leu Lys Ser Val Pro Thr Phe Gln Ser
    210                 215                 220

Leu Pro Glu Glu Ile Leu Ser Lys Leu Ala Asp Val Leu Glu Glu Thr
225                 230                 235                 240
```

```
His Tyr Glu Asn Gly Glu Tyr Ile Ile Arg Gln Gly Ala Arg Gly Asp
                245                 250                 255

Thr Phe Phe Ile Ile Ser Lys Gly Thr Val Asn Val Thr Arg Glu Asp
                260                 265                 270

Ser Pro Ser Glu Asp Pro Val Phe Leu Arg Thr Leu Gly Lys Gly Asp
            275                 280                 285

Trp Phe Gly Glu Lys Ala Leu Gln Gly Glu Asp Val Arg Thr Ala Asn
290                 295                 300

Val Ile Ala Ala Glu Ala Val Thr Cys Leu Val Ile Asp Arg Asp Ser
305                 310                 315                 320

Phe Lys His Leu Ile Gly Gly Leu Asp Asp Val Ser Asn Lys Ala Tyr
                325                 330                 335

Glu Asp Ala Glu Ala Lys Ala Lys Tyr Glu Ala Glu Ala Ala Phe Phe
            340                 345                 350

Ala Asn Leu Lys Leu Ser Asp Phe Asn Ile Ile Asp Thr Leu Gly Val
                355                 360                 365

Gly Gly Phe Gly Arg Val Glu Leu Val Gln Leu Lys Ser Glu Glu Ser
370                 375                 380

Lys Thr Phe Ala Met Lys Ile Leu Lys Lys Arg His Ile Val Asp Thr
385                 390                 395                 400

Arg Gln Gln Glu His Ile Arg Ser Glu Lys Gln Ile Met Gln Gly Ala
                405                 410                 415

His Ser Asp Phe Ile Val Arg Leu Tyr Arg Thr Phe Lys Asp Ser Lys
            420                 425                 430

Tyr Leu Tyr Met Leu Met Glu Ala Cys Leu Gly Gly Glu Leu Trp Thr
        435                 440                 445

Ile Leu Arg Asp Arg Gly Ser Phe Glu Asp Ser Thr Thr Arg Phe Tyr
    450                 455                 460

Thr Ala Cys Val Val Glu Ala Phe Ala Tyr Leu His Ser Lys Gly Ile
465                 470                 475                 480

Ile Tyr Arg Asp Leu Lys Pro Glu Asn Leu Ile Leu Asp His Arg Gly
                485                 490                 495

Tyr Ala Lys Leu Val Asp Phe Gly Phe Ala Lys Lys Ile Gly Phe Gly
            500                 505                 510

Lys Lys Thr Trp Thr Phe Cys Gly Thr Pro Glu Tyr Val Ala Pro Glu
        515                 520                 525

Ile Ile Leu Asn Lys Gly His Asp Ile Ser Ala Asp Tyr Trp Ser Leu
    530                 535                 540

Gly Ile Leu Met Tyr Glu Leu Leu Thr Gly Ser Pro Pro Phe Ser Gly
545                 550                 555                 560

Pro Asp Pro Met Lys Thr Tyr Asn Ile Ile Leu Arg Gly Ile Asp Met
                565                 570                 575

Ile Glu Phe Pro Lys Lys Ile Ala Lys Asn Ala Ala Asn Leu Ile Lys
            580                 585                 590

Lys Leu Cys Arg Asp Asn Pro Ser Glu Arg Leu Gly Asn Leu Lys Asn
        595                 600                 605

Gly Val Lys Asp Ile Gln Lys His Lys Trp Phe Glu Gly Phe Asn Trp
    610                 615                 620

Glu Gly Leu Arg Lys Gly Thr Leu Thr Pro Pro Ile Ile Pro Ser Val
625                 630                 635                 640

Ala Ser Pro Thr Asp Thr Ser Asn Phe Asp Ser Phe Pro Glu Asp Asn
                645                 650                 655

Asp Glu Pro Pro Pro Asp Asp Asn Ser Gly Trp Asp Ile Asp Phe
```

-continued

```
                 660             665             670
```

<210> SEQ ID NO 55
<211> LENGTH: 762
<212> TYPE: PRT
<213> ORGANISM: Homo sapiens

<400> SEQUENCE: 55

```
Met Gly Asn Gly Ser Val Lys Pro Lys His Ser Lys His Pro Asp Gly
1               5                   10                  15

His Ser Gly Asn Leu Thr Thr Asp Ala Leu Arg Asn Lys Val Thr Glu
            20                  25                  30

Leu Glu Arg Glu Leu Arg Arg Lys Asp Ala Glu Ile Gln Glu Arg Glu
        35                  40                  45

Tyr His Leu Lys Glu Leu Arg Glu Gln Leu Ser Lys Gln Thr Val Ala
    50                  55                  60

Ile Ala Glu Leu Thr Glu Glu Leu Gln Asn Lys Cys Ile Gln Leu Asn
65                  70                  75                  80

Lys Leu Gln Asp Val Val His Met Gln Gly Gly Ser Pro Leu Gln Ala
                85                  90                  95

Ser Pro Asp Lys Val Pro Leu Glu Val His Arg Lys Thr Ser Gly Leu
            100                 105                 110

Val Ser Leu His Ser Arg Arg Gly Ala Lys Ala Gly Val Ser Ala Glu
        115                 120                 125

Pro Thr Thr Arg Thr Tyr Asp Leu Asn Lys Pro Pro Glu Phe Ser Phe
    130                 135                 140

Glu Lys Ala Arg Val Arg Lys Asp Ser Ser Glu Lys Lys Leu Ile Thr
145                 150                 155                 160

Asp Ala Leu Asn Lys Asn Gln Phe Leu Lys Arg Leu Asp Pro Gln Gln
                165                 170                 175

Ile Lys Asp Met Val Glu Cys Met Tyr Gly Arg Asn Tyr Gln Gln Gly
            180                 185                 190

Ser Tyr Ile Ile Lys Gln Gly Glu Pro Gly Asn His Ile Phe Val Leu
        195                 200                 205

Ala Glu Gly Arg Leu Glu Val Phe Gln Gly Glu Lys Leu Leu Ser Ser
    210                 215                 220

Ile Pro Met Trp Thr Thr Phe Gly Glu Leu Ala Ile Leu Tyr Asn Cys
225                 230                 235                 240

Thr Arg Thr Ala Ser Val Lys Ala Ile Thr Asn Val Lys Thr Trp Ala
                245                 250                 255

Leu Asp Arg Glu Val Phe Gln Asn Ile Met Arg Arg Thr Ala Gln Ala
            260                 265                 270

Arg Asp Glu Gln Tyr Arg Asn Phe Leu Arg Ser Val Ser Leu Leu Lys
        275                 280                 285

Asn Leu Pro Glu Asp Lys Leu Thr Lys Ile Ile Asp Cys Leu Glu Val
    290                 295                 300

Glu Tyr Tyr Asp Lys Gly Asp Tyr Ile Ile Arg Glu Gly Glu Glu Gly
305                 310                 315                 320

Ser Thr Phe Phe Ile Leu Ala Lys Gly Lys Val Lys Val Thr Gln Ser
                325                 330                 335

Thr Glu Gly His Asp Gln Pro Gln Leu Ile Lys Thr Leu Gln Lys Gly
            340                 345                 350

Glu Tyr Phe Gly Glu Lys Ala Leu Ile Ser Asp Asp Val Arg Ser Ala
        355                 360                 365

Asn Ile Ile Ala Glu Glu Asn Asp Val Ala Cys Leu Val Ile Asp Arg
```

```
                370             375             380
Glu Thr Phe Asn Gln Thr Val Gly Thr Phe Glu Leu Gln Lys Tyr
385                 390                 395                 400

Leu Glu Gly Tyr Val Ala Asn Leu Asn Arg Asp Asp Glu Lys Arg His
                405                 410                 415

Ala Lys Arg Ser Met Ser Asn Trp Lys Leu Ser Lys Ala Leu Ser Leu
                420                 425                 430

Glu Met Ile Gln Leu Lys Glu Lys Val Ala Arg Phe Ser Ser Ser Ser
            435                 440                 445

Pro Phe Gln Asn Leu Glu Ile Ile Ala Thr Leu Gly Val Gly Gly Phe
    450                 455                 460

Gly Arg Val Glu Leu Val Lys Val Lys Asn Glu Asn Val Ala Phe Ala
465                 470                 475                 480

Met Lys Cys Ile Arg Lys Lys His Ile Val Asp Thr Lys Gln Gln Glu
                485                 490                 495

His Val Tyr Ser Glu Lys Arg Ile Leu Glu Glu Leu Cys Ser Pro Phe
            500                 505                 510

Ile Val Lys Leu Tyr Arg Thr Phe Lys Asp Asn Lys Tyr Val Tyr Met
            515                 520                 525

Leu Leu Glu Ala Cys Leu Gly Gly Glu Leu Trp Ser Ile Leu Arg Asp
530                 535                 540

Arg Gly Ser Phe Asp Glu Pro Thr Ser Lys Phe Cys Val Ala Cys Val
545                 550                 555                 560

Thr Glu Ala Phe Asp Tyr Leu His Arg Leu Gly Ile Ile Tyr Arg Asp
                565                 570                 575

Leu Lys Pro Glu Asn Leu Ile Leu Asp Ala Glu Gly Tyr Leu Lys Leu
            580                 585                 590

Val Asp Phe Gly Phe Ala Lys Lys Ile Gly Ser Gly Gln Lys Thr Trp
            595                 600                 605

Thr Phe Cys Gly Thr Pro Glu Tyr Val Ala Pro Glu Val Ile Leu Asn
            610                 615                 620

Lys Gly His Asp Phe Ser Val Asp Phe Trp Ser Leu Gly Ile Leu Val
625                 630                 635                 640

Tyr Glu Leu Leu Thr Gly Asn Pro Pro Phe Ser Gly Val Asp Gln Met
                645                 650                 655

Met Thr Tyr Asn Leu Ile Leu Lys Gly Ile Glu Lys Met Asp Phe Pro
                660                 665                 670

Arg Lys Ile Thr Arg Arg Pro Glu Asp Leu Ile Arg Arg Leu Cys Arg
            675                 680                 685

Gln Asn Pro Thr Glu Arg Leu Gly Asn Leu Lys Asn Gly Ile Asn Asp
690                 695                 700

Ile Lys Lys His Arg Trp Leu Asn Gly Phe Asn Trp Glu Gly Leu Lys
705                 710                 715                 720

Ala Arg Ser Leu Pro Ser Pro Leu Gln Arg Glu Leu Lys Gly Pro Ile
                725                 730                 735

Asp His Ser Tyr Phe Asp Lys Tyr Pro Pro Glu Lys Gly Met Pro Pro
            740                 745                 750

Asp Glu Leu Ser Gly Trp Asp Lys Asp Phe
            755                 760

<210> SEQ ID NO 56
<211> LENGTH: 762
<212> TYPE: PRT
<213> ORGANISM: Mus musculus
```

<400> SEQUENCE: 56

```
Met Gly Asn Gly Ser Val Lys Pro Lys His Ser Lys His Pro Asp Gly
1               5                   10                  15

His Ser Gly Asn Leu Thr Thr Asp Ala Leu Arg Asn Lys Val Thr Glu
            20                  25                  30

Leu Glu Arg Glu Leu Arg Arg Lys Asp Ala Glu Ile Gln Glu Arg Glu
        35                  40                  45

Tyr His Leu Lys Glu Leu Arg Glu Gln Leu Ser Lys Gln Thr Val Ala
    50                  55                  60

Ile Ala Glu Leu Thr Glu Glu Leu Gln Asn Lys Cys Ile Gln Leu Asn
65                  70                  75                  80

Lys Leu Gln Asp Val Val His Met Gln Gly Gly Ser Pro Leu Gln Ala
                85                  90                  95

Ser Pro Asp Lys Val Pro Leu Glu Val His Arg Lys Thr Ser Gly Leu
            100                 105                 110

Val Ser Leu His Ser Arg Arg Gly Ala Lys Ala Gly Val Ser Ala Glu
        115                 120                 125

Pro Thr Thr Arg Thr Tyr Asp Leu Asn Lys Pro Pro Glu Phe Ser Phe
    130                 135                 140

Glu Lys Ala Arg Val Arg Lys Asp Ser Ser Glu Lys Lys Leu Ile Thr
145                 150                 155                 160

Asp Ala Leu Asn Lys Asn Gln Phe Leu Lys Arg Leu Asp Pro Gln Gln
                165                 170                 175

Ile Lys Asp Met Val Glu Cys Met Tyr Gly Arg Asn Tyr Gln Gln Gly
            180                 185                 190

Ser Tyr Ile Ile Lys Gln Gly Glu Pro Gly Asn His Ile Phe Val Leu
        195                 200                 205

Ala Glu Gly Arg Leu Glu Val Phe Gln Gly Glu Lys Leu Leu Ser Ser
    210                 215                 220

Ile Pro Met Trp Thr Thr Phe Gly Glu Leu Ala Ile Leu Tyr Asn Cys
225                 230                 235                 240

Thr Arg Thr Ala Ser Val Lys Ala Ile Thr Asn Val Lys Thr Trp Ala
                245                 250                 255

Leu Asp Arg Glu Val Phe Gln Asn Ile Met Arg Arg Thr Ala Gln Ala
            260                 265                 270

Arg Asp Glu Gln Tyr Arg Asn Phe Leu Arg Ser Val Ser Leu Leu Lys
        275                 280                 285

Asn Leu Pro Glu Asp Lys Leu Thr Lys Ile Ile Asp Cys Leu Glu Val
    290                 295                 300

Glu Tyr Tyr Asp Lys Gly Asp Tyr Ile Ile Arg Glu Gly Glu Glu Gly
305                 310                 315                 320

Ser Thr Phe Phe Ile Leu Ala Lys Gly Lys Val Lys Val Thr Gln Ser
                325                 330                 335

Thr Glu Gly His Asp Gln Pro Gln Leu Ile Lys Thr Leu Gln Lys Gly
            340                 345                 350

Glu Tyr Phe Gly Glu Lys Ala Leu Ile Ser Asp Asp Val Arg Ser Ala
        355                 360                 365

Asn Ile Ile Ala Glu Glu Asn Asp Val Ala Cys Leu Val Ile Asp Arg
    370                 375                 380

Glu Thr Phe Asn Gln Thr Val Gly Thr Phe Glu Glu Leu Gln Lys Tyr
385                 390                 395                 400

Leu Glu Gly Tyr Val Ala Asn Leu Asn Arg Asp Asp Glu Lys Arg His
                405                 410                 415
```

```
Ala Lys Arg Ser Met Ser Asn Trp Lys Leu Ser Lys Ala Leu Ser Leu
            420                 425                 430

Glu Met Ile Gln Leu Lys Glu Lys Val Ala Arg Phe Ser Ser Ser Ser
            435                 440                 445

Pro Phe Gln Asn Leu Glu Ile Ile Ala Thr Leu Gly Val Gly Gly Phe
450                 455                 460

Gly Arg Val Glu Leu Val Lys Val Lys Asn Glu Asn Val Ala Phe Ala
465                 470                 475                 480

Met Lys Cys Ile Arg Lys Lys His Ile Val Asp Thr Lys Gln Gln Glu
                485                 490                 495

His Val Tyr Ser Glu Lys Arg Ile Leu Glu Glu Leu Cys Ser Pro Phe
            500                 505                 510

Ile Val Lys Leu Tyr Arg Thr Phe Lys Asp Asn Lys Tyr Val Tyr Met
            515                 520                 525

Leu Leu Glu Ala Cys Leu Gly Gly Glu Leu Trp Ser Ile Leu Arg Asp
530                 535                 540

Arg Gly Ser Phe Asp Glu Pro Thr Ser Lys Phe Cys Val Ala Cys Val
545                 550                 555                 560

Thr Glu Ala Phe Asp Tyr Leu His Arg Leu Gly Ile Ile Tyr Arg Asp
                565                 570                 575

Leu Lys Pro Glu Asn Leu Ile Leu Asp Ala Glu Gly Tyr Leu Lys Leu
            580                 585                 590

Val Asp Phe Gly Phe Ala Lys Lys Ile Gly Ser Gly Gln Lys Thr Trp
            595                 600                 605

Thr Phe Cys Gly Thr Pro Glu Tyr Val Ala Pro Glu Val Ile Leu Asn
610                 615                 620

Lys Gly His Asp Phe Ser Val Asp Phe Trp Ser Leu Gly Ile Leu Val
625                 630                 635                 640

Tyr Glu Leu Leu Thr Gly Asn Pro Pro Phe Ser Gly Val Asp Gln Met
                645                 650                 655

Met Thr Tyr Asn Leu Ile Leu Lys Gly Ile Glu Lys Met Asp Phe Pro
            660                 665                 670

Arg Lys Ile Thr Arg Arg Pro Glu Asp Leu Ile Arg Arg Leu Cys Arg
            675                 680                 685

Gln Asn Pro Thr Glu Arg Leu Gly Asn Leu Lys Asn Gly Ile Asn Asp
690                 695                 700

Ile Lys Lys His Arg Trp Leu Asn Gly Phe Asn Trp Glu Gly Leu Lys
705                 710                 715                 720

Ala Arg Ser Leu Pro Ser Pro Leu Gln Arg Glu Leu Lys Gly Pro Ile
                725                 730                 735

Asp His Ser Tyr Phe Asp Lys Tyr Pro Pro Glu Lys Gly Met Pro Pro
            740                 745                 750

Asp Glu Leu Ser Gly Trp Asp Lys Asp Phe
            755                 760

<210> SEQ ID NO 57
<211> LENGTH: 762
<212> TYPE: PRT
<213> ORGANISM: Mus musculus

<400> SEQUENCE: 57

Met Gly Asn Gly Ser Val Lys Pro Lys His Ala Lys His Pro Asp Gly
1               5                   10                  15

His Ser Gly Asn Leu Ser Asn Glu Ala Leu Arg Ser Lys Val Leu Glu
            20                  25                  30
```

-continued

```
Leu Glu Arg Glu Leu Arg Arg Lys Asp Ala Glu Leu Gln Glu Arg Glu
        35                  40                  45
Tyr His Leu Lys Glu Leu Arg Glu Gln Leu Ala Lys Gln Thr Val Ala
    50                  55                  60
Ile Ala Glu Leu Thr Glu Glu Leu Gln Ser Lys Cys Ile Gln Leu Asn
65                  70                  75                  80
Lys Leu Gln Asp Val Ile His Val Gln Gly Gly Ser Pro Leu Gln Ala
                85                  90                  95
Ser Pro Asp Lys Val Pro Leu Asp Val His Arg Lys Thr Ser Gly Leu
            100                 105                 110
Val Ser Leu His Ser Arg Arg Gly Ala Lys Ala Gly Val Ser Ala Glu
        115                 120                 125
Pro Thr Thr Arg Thr Tyr Asp Leu Asn Lys Pro Pro Glu Phe Ser Phe
    130                 135                 140
Glu Lys Ala Arg Val Arg Lys Asp Ser Ser Glu Lys Lys Leu Ile Thr
145                 150                 155                 160
Asp Ala Leu Asn Lys Asn Gln Phe Leu Lys Arg Leu Asp Pro Gln Gln
                165                 170                 175
Ile Lys Asp Met Val Glu Cys Met Tyr Gly Glu Lys Leu Ser Thr Gly
            180                 185                 190
Ser Tyr Val Ile Lys Gln Gly Glu Pro Gly Asn His Ile Phe Val Leu
        195                 200                 205
Ala Glu Gly Arg Leu Glu Val Phe Gln Gly Glu Lys Leu Leu Ser Ser
    210                 215                 220
Ile Pro Met Trp Thr Thr Phe Gly Glu Leu Ala Ile Leu Tyr Asn Cys
225                 230                 235                 240
Thr Arg Thr Ala Ser Val Lys Ala Ile Thr Asn Val Lys Thr Trp Ala
                245                 250                 255
Leu Asp Arg Glu Val Phe Gln Asn Ile Met Arg Arg Thr Ala Gln Ala
            260                 265                 270
Arg Asp Glu Glu Tyr Arg Asn Phe Leu Arg Ser Val Ser Leu Leu Lys
        275                 280                 285
Asn Leu Pro Glu Asp Lys Leu Thr Lys Ile Ile Asp Cys Leu Glu Val
    290                 295                 300
Glu Tyr Tyr Asp Lys Gly Asp Tyr Ile Ile Arg Glu Gly Glu Glu Gly
305                 310                 315                 320
Ser Thr Phe Phe Ile Leu Ala Lys Gly Lys Val Lys Val Thr Gln Ser
                325                 330                 335
Thr Glu Gly His Asp Gln Pro Gln Leu Ile Lys Thr Leu Gln Lys Gly
            340                 345                 350
Glu Tyr Phe Gly Glu Lys Ala Leu Ile Ser Asp Asp Val Arg Ser Ala
        355                 360                 365
Asn Ile Ile Ala Glu Glu Asn Asp Val Ala Cys Leu Val Ile Asp Arg
    370                 375                 380
Glu Thr Phe Asn Gln Thr Val Gly Thr Phe Asp Glu Leu Gln Lys Tyr
385                 390                 395                 400
Leu Glu Gly Tyr Val Ala Thr Leu Asn Arg Asp Asp Glu Lys Arg His
                405                 410                 415
Ala Lys Arg Ser Met Ser Ser Trp Lys Leu Ser Lys Ala Leu Ser Leu
            420                 425                 430
Glu Met Ile Gln Leu Lys Glu Lys Val Ala Arg Phe Ser Ser Thr Ser
        435                 440                 445
Pro Phe Gln Asn Leu Glu Ile Ile Ala Thr Leu Gly Val Gly Gly Phe
    450                 455                 460
```

Gly Arg Val Glu Leu Val Lys Val Lys Asn Glu Asn Val Ala Phe Ala
465                 470                 475                 480

Met Lys Cys Ile Arg Lys His Ile Val Asp Thr Lys Gln Gln Glu
            485                 490                 495

His Val Tyr Ser Glu Lys Arg Ile Leu Glu Glu Leu Cys Ser Pro Phe
            500                 505                 510

Ile Val Lys Leu Tyr Arg Thr Phe Lys Asp Asn Lys Tyr Val Tyr Met
            515                 520                 525

Leu Leu Glu Ala Cys Leu Gly Gly Glu Leu Trp Ser Ile Leu Arg Asp
        530                 535                 540

Arg Gly Ser Phe Asp Glu Pro Thr Ser Lys Phe Cys Val Ala Cys Val
545                 550                 555                 560

Thr Glu Ala Phe Asp Tyr Leu His Leu Leu Gly Ile Ile Tyr Arg Asp
            565                 570                 575

Leu Lys Pro Glu Asn Leu Ile Leu Asp Ala Asp Gly Tyr Leu Lys Leu
            580                 585                 590

Val Asp Phe Gly Phe Ala Lys Lys Ile Gly Ser Gly Gln Lys Thr Trp
            595                 600                 605

Thr Phe Cys Gly Thr Pro Glu Tyr Val Ala Pro Glu Val Ile Leu Asn
            610                 615                 620

Lys Gly His Asp Phe Ser Val Asp Phe Trp Ser Leu Gly Ile Leu Val
625                 630                 635                 640

Tyr Glu Leu Leu Thr Gly Asn Pro Pro Phe Ser Gly Ile Asp Gln Met
            645                 650                 655

Met Thr Tyr Asn Leu Ile Leu Lys Gly Ile Glu Lys Met Asp Phe Pro
            660                 665                 670

Arg Lys Ile Thr Arg Arg Pro Glu Asp Leu Ile Arg Arg Leu Cys Arg
            675                 680                 685

Gln Asn Pro Thr Glu Arg Leu Gly Asn Leu Lys Asn Gly Ile Asn Asp
            690                 695                 700

Ile Lys Lys His Arg Trp Leu Asn Gly Phe Asn Trp Glu Gly Leu Lys
705                 710                 715                 720

Ala Arg Ser Leu Pro Ser Pro Leu Arg Arg Glu Leu Ser Gly Pro Ile
            725                 730                 735

Asp His Ser Tyr Phe Asp Lys Tyr Pro Pro Gly Lys Gly Val Pro Pro
            740                 745                 750

Asp Glu Met Ser Gly Trp Asp Lys Asp Phe
            755                 760

<210> SEQ ID NO 58
<211> LENGTH: 762
<212> TYPE: PRT
<213> ORGANISM: Rattus norvegicus

<400> SEQUENCE: 58

Met Gly Asn Gly Ser Val Lys Pro Lys His Ala Lys His Pro Asp Gly
1               5                   10                  15

His Ser Gly Asn Leu Ser Asn Glu Ala Leu Arg Ser Lys Val Leu Glu
            20                  25                  30

Leu Glu Arg Glu Leu Arg Arg Lys Asp Ala Glu Leu Gln Glu Arg Glu
        35                  40                  45

Tyr His Leu Lys Glu Leu Arg Glu Gln Leu Ala Lys Gln Thr Val Ala
    50                  55                  60

Ile Ala Glu Leu Thr Glu Glu Leu Gln Ser Lys Cys Ile Gln Leu Asn
65                  70                  75                  80

```
Lys Leu Gln Asp Val Ile His Val Gln Gly Gly Ser Pro Leu Gln Ala
                85                  90                  95

Ser Pro Asp Lys Val Pro Leu Asp Val His Arg Lys Thr Ser Gly Leu
            100                 105                 110

Val Ser Leu His Ser Arg Arg Gly Ala Lys Ala Gly Val Ser Ala Glu
        115                 120                 125

Pro Thr Thr Arg Thr Tyr Asp Leu Asn Lys Pro Pro Glu Phe Ser Phe
    130                 135                 140

Glu Lys Ala Arg Val Arg Lys Asp Ser Ser Glu Lys Lys Leu Ile Thr
145                 150                 155                 160

Asp Ala Leu Asn Lys Asn Gln Phe Leu Lys Arg Leu Asp Pro Gln Gln
                165                 170                 175

Ile Lys Asp Met Val Glu Cys Met Tyr Gly Glu Lys Leu Ser Thr Gly
            180                 185                 190

Ser Tyr Val Ile Lys Gln Gly Glu Pro Gly Asn His Ile Phe Val Leu
        195                 200                 205

Ala Glu Gly Arg Leu Glu Val Phe Gln Gly Glu Lys Leu Leu Ser Ser
    210                 215                 220

Ile Pro Met Trp Thr Thr Phe Gly Glu Leu Ala Ile Leu Tyr Asn Cys
225                 230                 235                 240

Thr Arg Thr Ala Ser Val Lys Ala Ile Thr Asn Val Lys Thr Trp Ala
                245                 250                 255

Leu Asp Arg Glu Val Phe Gln Asn Ile Met Arg Arg Thr Ala Gln Ala
            260                 265                 270

Arg Asp Glu Glu Tyr Arg Asn Phe Leu Arg Ser Val Ser Leu Leu Lys
        275                 280                 285

Asn Leu Pro Glu Asp Lys Leu Thr Lys Ile Ile Asp Cys Leu Glu Val
    290                 295                 300

Glu Tyr Tyr Asp Lys Gly Asp Tyr Ile Ile Arg Glu Gly Glu Glu Gly
305                 310                 315                 320

Ser Thr Phe Phe Ile Leu Ala Lys Gly Lys Val Lys Val Thr Gln Ser
                325                 330                 335

Thr Glu Gly His Asp Gln Pro Gln Leu Ile Lys Thr Leu Gln Lys Gly
            340                 345                 350

Glu Tyr Phe Gly Glu Lys Ala Leu Ile Ser Asp Asp Val Arg Ser Ala
        355                 360                 365

Asn Ile Ile Ala Glu Glu Asn Asp Val Ala Cys Leu Val Ile Asp Arg
    370                 375                 380

Glu Thr Phe Asn Gln Thr Val Gly Thr Phe Asp Glu Leu Gln Lys Tyr
385                 390                 395                 400

Leu Glu Gly Tyr Val Ala Thr Leu Asn Arg Asp Asp Glu Lys Arg His
                405                 410                 415

Ala Lys Arg Ser Met Ser Ser Trp Lys Leu Ser Lys Ala Leu Ser Leu
            420                 425                 430

Glu Met Ile Gln Leu Lys Glu Lys Val Ala Arg Phe Ser Ser Thr Ser
        435                 440                 445

Pro Phe Gln Asn Leu Glu Ile Ile Ala Thr Leu Gly Val Gly Gly Phe
    450                 455                 460

Gly Arg Val Glu Leu Val Lys Val Lys Asn Glu Asn Val Ala Phe Ala
465                 470                 475                 480

Met Lys Cys Ile Arg Lys Lys His Ile Val Asp Thr Lys Gln Gln Glu
                485                 490                 495

His Val Tyr Ser Glu Lys Arg Ile Leu Glu Glu Leu Cys Ser Pro Phe
```

-continued

```
                        500                 505                 510
Ile Val Lys Leu Tyr Arg Thr Phe Lys Asp Asn Lys Tyr Val Tyr Met
        515                 520                 525

Leu Leu Glu Ala Cys Leu Gly Gly Glu Leu Trp Ser Ile Leu Arg Asp
        530                 535                 540

Arg Gly Ser Phe Asp Glu Pro Thr Ser Lys Phe Cys Val Ala Cys Val
545                 550                 555                 560

Thr Glu Ala Phe Tyr Leu His Leu Leu Gly Ile Ile Tyr Arg Asp
                565                 570                 575

Leu Lys Pro Glu Asn Leu Ile Leu Asp Ala Asp Gly Tyr Leu Lys Leu
                580                 585                 590

Val Asp Phe Gly Phe Ala Lys Lys Ile Gly Ser Gly Gln Lys Thr Trp
        595                 600                 605

Thr Phe Cys Gly Thr Pro Glu Tyr Val Ala Pro Glu Val Ile Leu Asn
        610                 615                 620

Lys Gly His Asp Phe Ser Val Asp Phe Trp Ser Leu Gly Ile Leu Val
625                 630                 635                 640

Tyr Glu Leu Leu Thr Gly Asn Pro Pro Phe Ser Gly Ile Asp Gln Met
                645                 650                 655

Met Thr Tyr Asn Leu Ile Leu Lys Gly Ile Glu Lys Met Asp Phe Pro
                660                 665                 670

Arg Lys Ile Thr Arg Arg Pro Glu Asp Leu Ile Arg Arg Leu Cys Arg
        675                 680                 685

Gln Asn Pro Thr Glu Arg Leu Gly Asn Leu Lys Asn Gly Ile Asn Asp
        690                 695                 700

Ile Lys Lys His Arg Trp Leu Asn Gly Phe Asn Trp Glu Gly Leu Lys
705                 710                 715                 720

Ala Arg Ser Leu Pro Ser Pro Leu Arg Arg Glu Leu Ser Gly Pro Ile
                725                 730                 735

Asp His Ser Tyr Phe Asp Lys Tyr Pro Pro Glu Lys Gly Val Pro Pro
                740                 745                 750

Asp Glu Met Ser Gly Trp Asp Lys Asp Phe
        755                 760
```

NEURONAL PAIN PATHWAY

The present application claims priority to U.S. Provisional Patent Application Ser. No. 60/713,435 which was filed Sep. 1, 2005, and U.S. Provisional Patent Application Ser. No. 60/664,071 which was filed Mar. 21, 2005 each of which is hereby incorporated by reference in their entireties.

GRANT INFORMATION

The subject matter of this application was developed at least in part under National Institutes of Health Grants NS12250 and NS35979, so that the United States Government has certain rights herein.

1. INTRODUCTION

The present invention relates to the discovery of a novel molecular pathway involved in long-term hyperexcitability of sensory neurons, which, in higher animals, is associated with persistent pain.

2. BACKGROUND OF THE INVENTION

Pain is perceived as a result of communication between the two main divisions—central and peripheral—of the nervous system. While the two divisions work together to produce our subjective experience, the central and peripheral nervous systems are anatomically and functionally different.

A painful stimulus impinging on a specialized pain receptor is propagated along a peripheral branch of a sensory axon to a neuron lying within a dorsal root ganglion (part of the peripheral nervous system) and then along a central branch of the axon into the spinal cord (central nervous system). The signal is subsequently relayed to a central nervous system neuron in the spinal cord which in turn passes the signal, through its axon, to the opposite ("contralateral") side of the spinal cord and then up to pain perceiving structures in the brain.

Peripheral pain receptors are located on free nerve endings which can respond to mechanical, thermal or chemical stimuli. Pain can be acute or chronic. Acute pain is typically transmitted from the receptor through Aδ sensory nerve fibers, which are thinly coated with the insulating compound, myelin, which facilitates impulse conduction. Chronic pain typically travels through C fibers, which, because they are unmyelinated, transmit impulses slowly, leading to the characteristic dull, diffuse nature of chronic pain. Chemical mediators of inflammation such as bradykinin and prostaglandins stimulate pain receptors, and are important agents in chronic pain syndromes, such as the persistent pain associated with arthritis or nerve inflammation.

The perception of pain can be altered at various stages of the pain pathway. For example, the painful stimulus can be eliminated by administering a local anesthetic to the peripheral receptor. Drugs like opioids were classically known to intervene at the central nervous system stage of the pain pathway, and non-steroidal anti-inflammatory drugs at the peripheral stage (although it is now realized that there is some cross-reactivity of both). Likewise, what is perceived as chronic pain (not due to primary spinal cord injury) is typically associated with sensitization of peripheral pain receptors as well as changes in the excitability of spinal neurons, and therefore has both peripheral and central nervous system components. The peripheral and central components involved in chronic pain are referred to, respectively, as "primary" and "secondary" hyperalgesia (Urban and Gebhart, 1999, citing Woolf, 1983 and La Motte et al., 1991).

In terms of the central nervous system components of chronic pain, the spinal cord neuron which receives the stimulus from the dorsal root ganglion axon, exhibits changes in gene expression in the context of chronic pain and is believed to contribute to the phenomenon of "central sensitization" or "spinal hyperalgesia." Spinal N-methyl-D-aspartate ("NMDA") receptors are believed to play an important role in this process (Urban and Gebhart, 1999, citing Urban and Gebhart, 1998; Palacek et al., 2003; Lee et al., 1993). Spinal cord injury without activation of the peripheral nervous system can also produce spinal hyperalgesia resulting in a central pain syndrome (Zhang et al., 2005). Central neuropathic pain has been associated with phosphorylation of the transcription factor, cyclic AMP response element binding protein ("CREB") (Cron et al., 2005).

Regarding the peripheral nervous system component of chronic pain associated with nerve injury ("neuropathic pain"), persistent neuropathic pain is a major clinical problem that has mostly resisted effective treatment. In humans (Gracely et al., 1992) and mammalian model systems (Millan, 1999), persistent pain after nerve injury is associated with long-term hyperexcitability (LTH) of sensory neurons (SNs) having axons in the injured nerve. LTH is manifested as increased sensitivity to electrical stimuli in the SN cell body and axon at the injury site (Wall and Devor, 1983; Study and Kral, 1996; Zhang et al., 1997; Chen and Devor, 1998; Kim et al., 1998; Abdulla and Smith, 2001). These changes result in discharge of action potentials from SNs at rest or during innocuous stimulation, leading to continuing excitation of higher order neurons in the central nervous system and to secondary, or spinal hyperalgesia and persistent pain. Because the appearance of LTH involves alterations in gene expression (Waxman et al., 1994; Wang et al., 2002; Park et al., 2003), a central question is, how are such changes in the nucleus induced by an injury that occurs far from the cell body? Answering this question has been extremely difficult using the complex mammalian nervous system.

An experimentally favorable alternative is the homogeneous cluster of SNs that reside in the bilateral pleural ganglia of the mollusk *Aplysia californica* (Walters et al., 2004). Noxious mechanical stimulation of the body wall (Walters et al., 1983a) or crushing SN axons in vivo or in vitro, elicits an LTH with electrophysiological properties similar to those seen after axotomy of mammalian SNs (Walters et al., 1991; Walters, 1994; Ambron et al., 1996; Bedi et al., 1998; Ungless et al., 2002; Sung and Ambron, 2004). The LTH appears after a delay, suggesting that its induction after nerve crush is attributable to a positive molecular injury signal (Walters et al., 1991; Ambron and Walters, 1996; Lin et al., 2003). Two studies support this idea. First, blocking axonal transport after nerve injury in excised nervous systems prevented the appearance of LTH (Gunstream et al., 1995). Second, LTH was induced in noninjured SNs by injecting axoplasm from injured axons (Ambron et al., 1995). LTH was also elicited in the SNs after intrasomatic injection of an ERK (extracellular signal-regulated kinase) member of the MAPK (mitogen-activated protein kinase) family (Sung et al., 2000). Other experiments have suggested that cGMP and PKG (cGMP-dependent protein kinase; protein kinase G) are probably involved (Lewin and Walters, 1999). However, despite these observations, the identity of the signal from the axon, how PKG and the ERK are activated, or how these kinases might interact were not known. Moreover, LTH was also reported to be induced by cAMP acting on PKA (protein kinase A) in a learning paradigm (Dale et al., 1988; Scholz and Byrne, 1988).

U.S. Pat. No. 6,476,007 by Tao and Johns ("Tao and Johns") relates to a proposed signalling pathway in the central nervous system in which stimulation of an N-methyl-D-aspartate ("NMDA") receptor leads to activation of nitric oxide synthase ("NOS") and production of nitric oxide ("NO"), which then stimulates guanylate cylase ("GC") and the production of cyclic guanoside monophosphate (cGMP), which in turn activates cGMP-dependent protein kinase Iα ("PKG"). It was observed that administration of the PKG inhibitor Rp-8-[4-chlorophenyl)thio-cGMPS triethylamine into the central nervous system by intrathecal administration, after the induction of an inflammatory response, produced significant antinociception in rats 10 and 60 minutes later. Further, they noted an upregulation of PKG expression in the lumbar spinal cord 96 hours after noxious stimulation was blocked by administration of a neuronal NOS inhibitor, a soluble GC inhibitor, and a NMDA receptor antagonist.

However, while Tao and Johns purports to address the mechanism of inflammatory hyperalgesia in the central nervous system, prior to the present invention the need remained to determine the mechanism of pain, and in particular chronic pain and long-term hyperexcitability, in the sensory neurons of the peripheral nervous system.

The need to address the mechanism of pain in the peripheral nervous system is important for several reasons, the first of which is drug accessibility. The central nervous system is sequestered from the rest of the body by the blood-brain-barrier, which is created by tight junctions between endothelial cells of the central nervous system and prevents many therapeutic drugs from ever reaching the central nervous system. Because of the extremely limited permeability of the blood-brain-barrier, treatment of spinal hyperalgesia according to Tao and Johns would be problematic. The ability, according to the present invention, to treat the primary hyperalgesia aspect of pain by delivering agents to the peripheral nervous system, which does not have the same permeability issues, confers a substantial advantage.

A second reason that treatment of peripheral pain mechanisms is important is that the periphery is the portal for pain perception. The present invention offers the advantage of intervening in subjective pain as it first arises, such as in the context of a normally non-painful stimulous which results in the perception of pain as a result of long term hyperexcitability (LTH). Subjective pain can be triggered in chronic pain sufferers by stimuli—such as the light touch of a sheet or a passing breeze—which would not normally be painful. The present invention is directed at this first stage of the pain pathway.

3. SUMMARY OF THE INVENTION

The present invention relates to the discovery of a novel molecular pathway involved in long-term hyperexcitability of sensory neurons in the peripheral nervous system, which, in higher animals, is associated with persistent pain. It is based on the discovery that, following injury to an axon of a sensory neuron, an increase in nitric oxide synthase ("NOS") activity results in increased nitric oxide ("NO") production, which, in turn, activates guanylyl cyclase ("GC"), thereby increasing levels of cyclic guanosine monophosphate ("cGMP"). Increased cGMP results in activation of protein kinase G ("PKG"), which then is retrogradely transported along the axon to the neuron cell body, where it phosphorylates mitogen-activated protein kinase-erk ("MAPKerk").

The activated MAPKerk then translocates into the cell nucleus, where it modulates expression of pain-related genes.

In various embodiments, the present invention provides for methods of and compositions for inhibiting and/or treating long-term hyperexcitability and/or persistent pain in a subject suffering from primary (peripheral nervous system) hyperalgesia, comprising administering, to the subject, an agent that inhibits a step in the above pathway. In particular embodiments, the agent is administered so as to be delivered to a sensory neuron in a dorsal root ganglion. In specific embodiments, the agent comprises a peptide that facilitates retrograde transport from the periphery to a sensory neuron cell body. In further embodiments, the present invention provides for assays that may be used to identify molecules that can modulate (inhibit or promote) steps in this pathway and thereby modulate long-term hyperexcitability and/or pain perception.

In still further embodiments, the present invention provides for a cloned PKG gene of *Aplysia californica*, its encoded protein and homologues thereof, and antibodies directed toward the purified protein.

4. BRIEF DESCRIPTION OF THE FIGURES

FIG. 1A-D. A, Top, A schematic diagram of apPKG showing the position of the conserved tandem cGMP binding domains, the ATP binding and catalytic sites, and the position of an autoinhibitory sequence. Bottom, Clustal W sequence alignment of the predicted apPKG amino acid sequence with *Drosophila* DG1 (GenBank accession number AAB03405; SEQ ID NO:52) and DG2T3a (AAA28459; SEQ ID NO:53), human Iα (BAA08297; SEQ ID NO:54) and II (CAA64318; SEQ ID NO:55), mouse Iβ (AAD16044; SEQ ID NO:56) and II (AAA02572; SEQ ID NO:57), and rat II (CAA85284; SEQ ID NO:58) PKGs. Conserved amino acids are shaded in black; similar amino acids are shaded in light gray. B, Phylogenetic analysis of the PKG family. C, Expression of apPKG in neurons. A multiple-tissue Northern blot was hybridized with a $^{32}$P-labeled N-terminal apPKG cDNA fragment. The arrow indicates apPKG mRNA. The sizes of RNA standards are indicated to the left of the figure. A $^{32}$P-labeled probe to 5S ribosomal RNA (arrow) was used to ensure loading uniformity. D, apPKG mRNA localization in pleural and pedal ganglia by in situ hybridization with a digoxigenin-labeled antisense RNA (left) or sense-RNA (right). apPKG mRNA is expressed in the pleural sensory cluster (arrow). Scale bar, 200 µm.

Figure 2A:
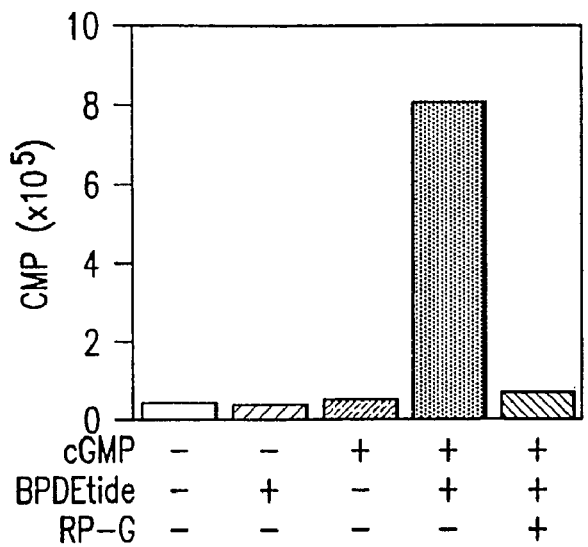
Figure 2B:
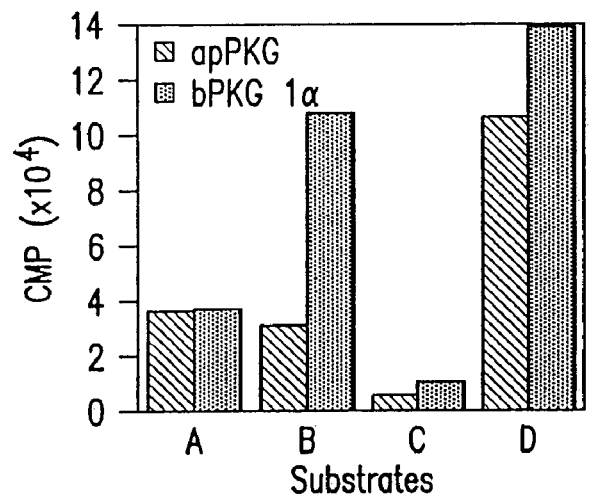
Figure 2C:
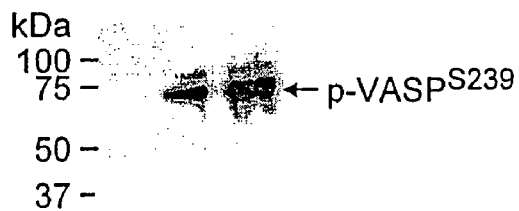

FIG. 2A-C. apPKG is a type-I PKG. A, The kinase activity of purified inactive recombinant apPKG protein (100 ng) was measured by the transfer of $^{32}$P from [$^{32}$P]ATP to BPDEtide in the presence (+) or absence (−) of 100 nM 8-Br-cGMP. Activity caused by autophosphorylation was subtracted using a peptide control reaction (see Materials and Methods). Note that the kinase activity was inhibited in the presence of 10 µM PKG inhibitor Rp-8-pCPT-cGMPS (RP-G). B, Kinase activity of active recombinant apPKG (25 ng) and bovine PKG type-Iα (bPKG1α) (50 ng) in the presence of four type-I PKG peptide substrates: peptide A, RKISASGP (SEQ ID NO:21); B, RKISASEFDRPLR (SEQ ID NO:22; BPDEtide); and D, RKRSRAE (SEQ ID NO:23) H$_2$Btide). Peptide C, QKRPRRKDTP (SEQ ID NO:24), is a type-II PKG substrate. C, apPKG phosphorylates recombinant VASP at serine-239. Purified recombinant VASP-GST (0.5 µg) was incubated with active apPKG (100 ng) or the recombinant bovine PKG (50 ng), or in the kinase buffer alone, at room temperature for 20 min. After SDS-PAGE, a Western blot was probed with an anti-phospho-VASP (Ser 239) (p-VASP S239) antibody.

Figure 3A:
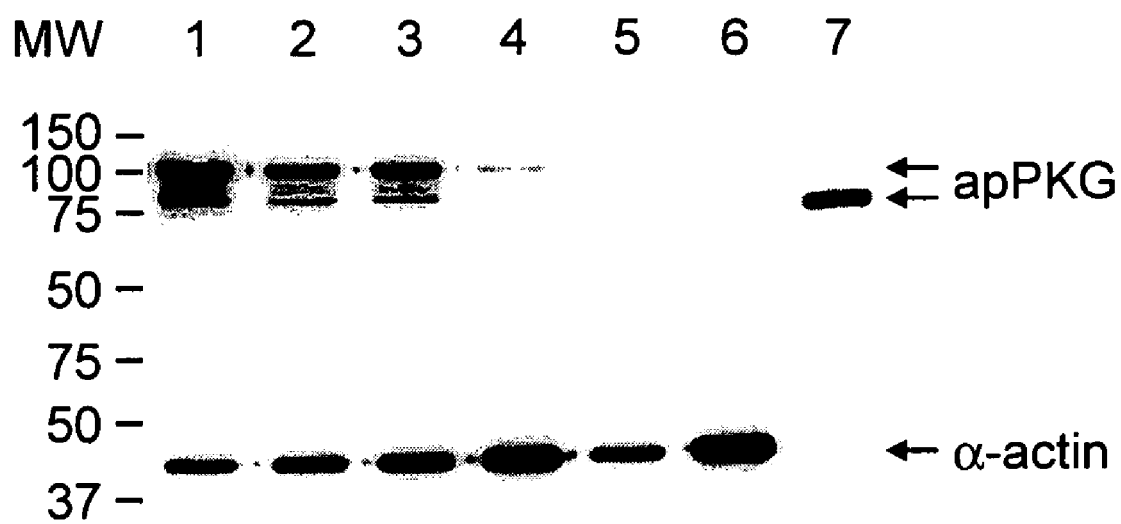
Figure 3B:
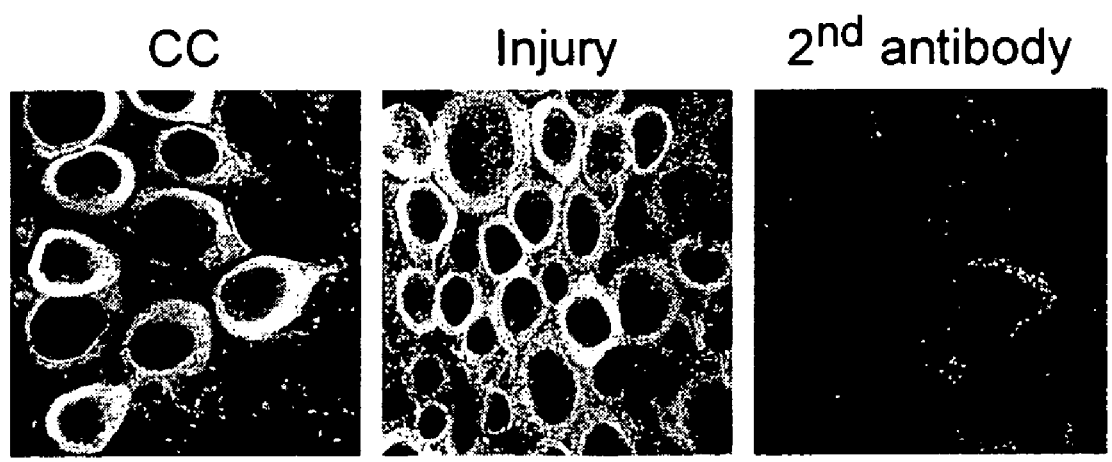

FIG. 3A-B. A, apPKG protein expression in the nervous system. Top, A Western blot (10 μg of protein per lane) was probed with antibody Ab apPKG raised against an N-terminal peptide of apPKG protein. Lane 1, Pedal ganglia; lane 2, pleural ganglia; lane 3, axoplasm extruded from peripheral nerves; lane 4, body wall muscle; lane 5, buccal mass; lane 6, genitalia; lane 7, recombinant apPKG. The two specific apPKG signals are indicated by arrows. Bottom, The blot was stripped and reprobed with an antibody against α-actin to indicate protein load. Positions of molecular mass markers in kilodaltons are indicated on the left. B, apPKG is expressed in the *Aplysia* SNs. Confocal microscopy of a 2 μm optical section taken from a Z-series through the pleural sensory cluster exposed to Ab apPKG 24 hr after nerve crush in vivo. Shown are representative images of contralateral uninjured (CC) and injured sensory clusters from sections in the middle of the neuron to show the nucleus. An injured sensory cluster stained in the presence of second Ab only shows the background staining. Scale bar, 20 μm. Although the staining is primarily in cytoplasm, the nucleus of some neurons is also stained. Note that the apPKG staining pattern is essentially identical between injured and contralateral uninjured sensory clusters.

Figure 4A:
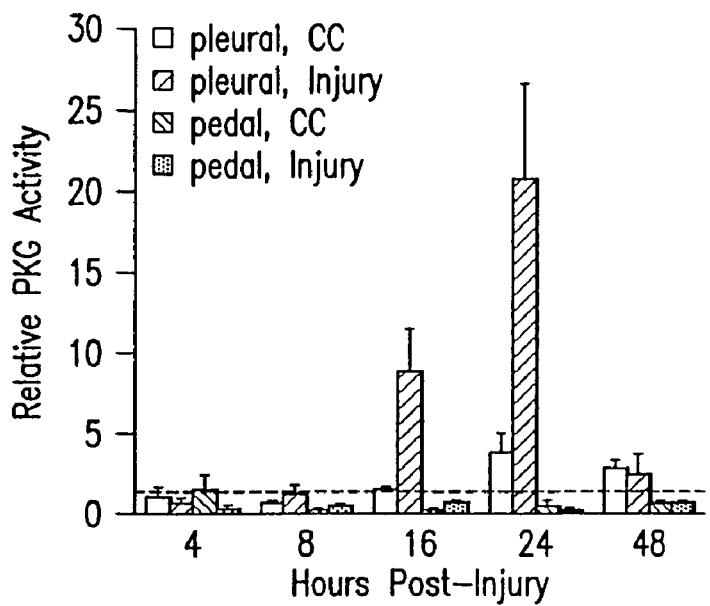
Figure 4B:
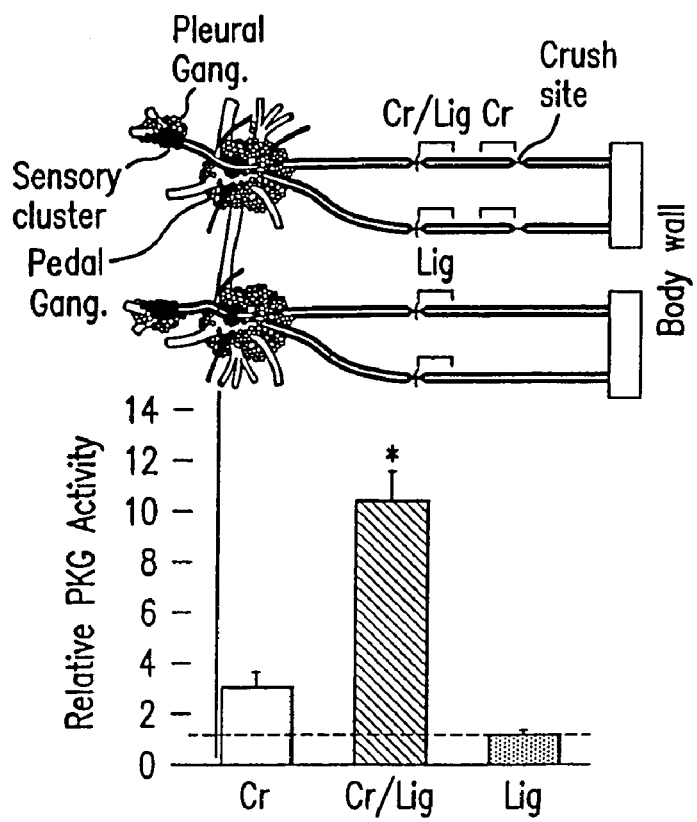
Figure 4C:
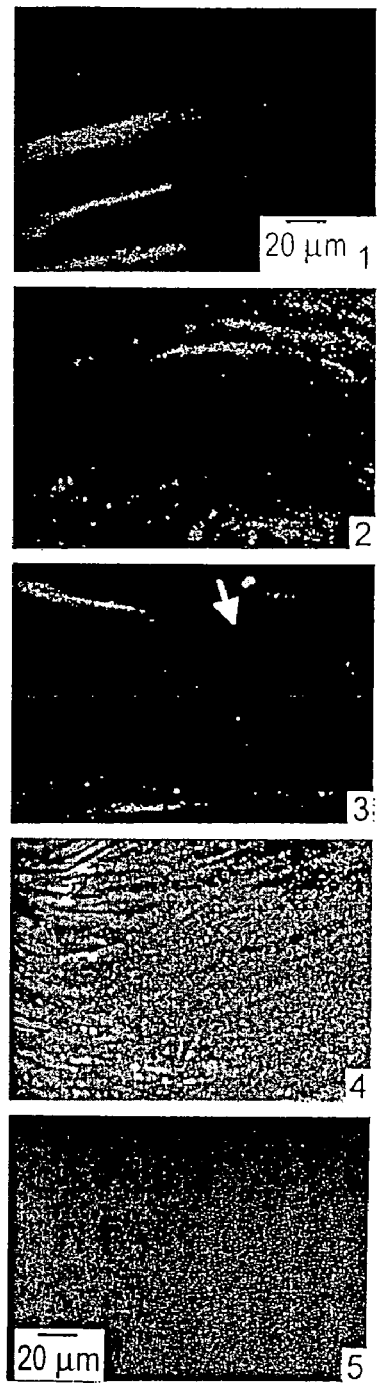

FIG. 4A-C. ApPKG activity appears in the pleural ganglion after a delay after nerve crush. A, Peripheral nerves p5-p9 were crushed on one side. At the indicated times, pleural (white/gray squares) and pedal (dotted/black squares) ganglia were collected from the injured (black/gray) and contralateral control (CC) (white/dotted) sides and assayed for apPKG activity using BPDEtide as substrate in the presence of the PKA-specific inhibitor 6-22 amide. ApPKG activity at each point was corrected for autophosphorylation and was normalized to total apPKG activity elicited by adding 1_M 8-Br-cGMP to a duplicate sample. Relative apPKG activity was the ratio of the apPKG activity of each sample to the basal apPKG activity in a sample from a naive animal. Six animals were examined independently at each time point. Two-way ANOVA with repeated measures showed significant effects of axotomy, time, and their interaction in the pleural ganglia ($p < 0.001$ in each case). B, apPKG is activated and retrogradely transported after injury. p5-p9 nerves were crushed and ligated. Twenty-four hours later, axoplasm was extruded from the crush (Cr) site, from the crush/ligation (Cr/Lig) site, and from the ligation (Lig) site on the control nerves, as indicated by brackets in the schematic. Axoplasm containing equal amounts of protein from each segment was assayed for apPKG activity as in A. The line indicates the level of basal apPKG activity, determined by assaying axoplasm collected from noninjured nerves. Error bars represent ±SEM. An asterisk indicates significant difference compared with all of the other groups ($p < 0.05$; ANOVA and Newman-Keuls tests). An enrichment of active apPKG at the Cr/Lig site is characteristic of positive molecular injury signals. C, ApPKG protein is retrogradely transported after injury. Peripheral nerves were crushed and ligated as in B. Twenty-four hours later, injured and control nerves were fixed, exposed to Ab apPKG, and processed for immunohistochemistry. Optical sections (2 μm) through each nerve were examined by confocal microscopy. All of the images were at the same magnification and were captured after identical exposures to the confocal beam. Each image is aligned in the same direction; the central somata are to the left of the segment shown. 1, Segment of a nerve from a noninjured animal 2, Segment containing the Lig site (arrow) on a nerve contralateral to the injury. 3, Segment of nerve containing the Cr site (arrow), which has expanded over the 24 hr. 4, Segment of nerve containing the Cr/Lig site (arrow). 5, Segment of nerve exposed to the second antibody only. Scale bar, 20 μm for all of the images.

Figure 5A:
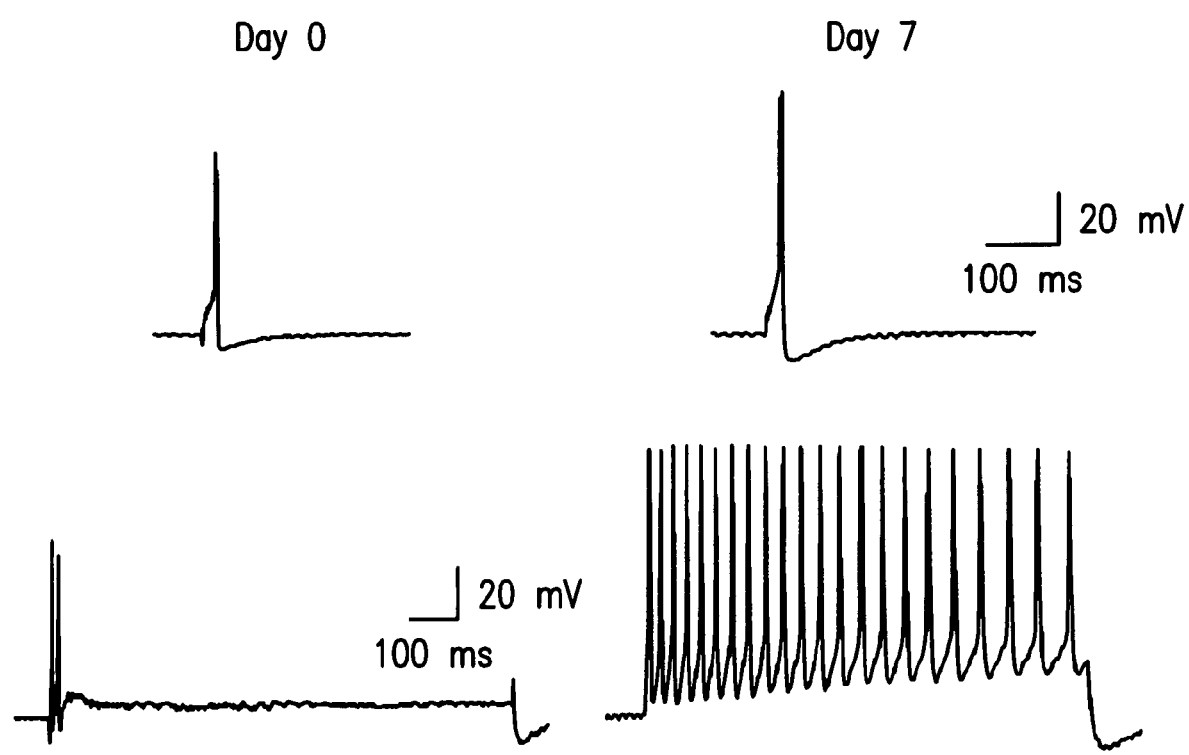
Figure 5B:
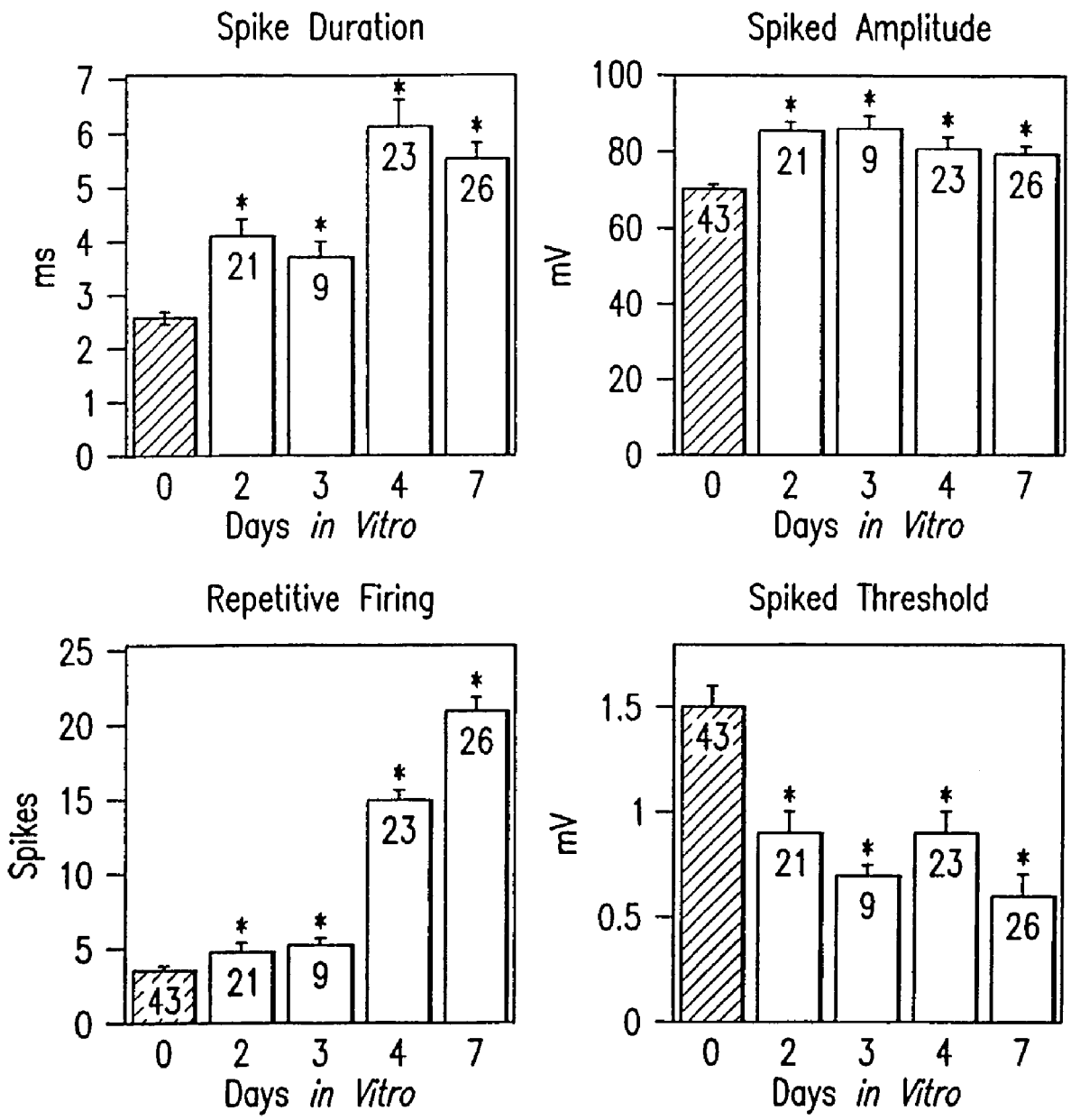

FIG. 5A-B. SNs develop an LTH in vitro. The electrical properties of SNs after time in vitro were compared with those in control SNs in the sensory cluster in vivo (d 0). A, Top, A representative single action potential elicited in response to a 20 msec depolarizing pulse showing the increase in spike amplitude after 7 d in vitro. Bottom, Action potential discharge in response to a normalized 1 sec intracellular test pulse. Note the repetitive firing in the neurons after 7 d in vitro. B, Data comparing spike duration, spike amplitude, spike threshold, and repetitive firing of control SNs (gray bars) with those after 2-7 d in vitro (open bars). Each bar contains the number of cells examined. Error bars represent ±SEM. An asterisk indicates significant difference from the in vivo value ($p < 0.01$; ANOVA and Newman-Keuls test).

FIG. 6A-D. Inhibiting NOS, sGC, or apPKG prevents the induction of LTH in SNs in vitro. SNs were removed from the cluster and grown in vitro in the presence of Rp-8-pCPT-cGMPS (RpcGMPS), Rp-8-pCPT-cAMPS (RpcAMPS), or ODQ (all 10 μM). Other SNs removed at the same time were not exposed to any inhibitors as controls (C). A, B, On the third day in vitro, 12 SNs exposed to Rp-cGMPS, Rp-cAMPS, or ODQ, and 12 control SNs were impaled with a microelectrode to assess repetitive firing in response to stimulation at three test currents (A) and to determine spike threshold (B). We examined the cells on the third day, and not later, to avoid more prolonged exposure to the drugs. Two-way ANOVA with repeated measures showed that both Rp-cGMPS and ODQ significantly reduced repetitive firing elicited by test currents of 2 and 3 nA relative to controls. Error bars indicate SEM, and the asterisks indicate significance ($p < 0.0001$ in each case). Similarly, Rp-cGMPS and ODQ significantly prevented the injury-induced decrease in threshold compared 4 with C cells (ANOVA and Fisher's PLSD tests; $p < 0.05$). There was a considerable variability in threshold in the presence of the Rp-cAMPS, and the mean difference from controls was not significant. C, Detection of nNOS mRNA in single SNs by RT-PCR. Fragments of appropriate lengths were amplified with primer sets for apnNOS, sensorin A, and the neuron-specific isoform of actin from five separate sets of samples from SNs in vivo (0) or after 16 hr in vitro. The size of the synthesized fragments detected by ethidium bromide staining on 2% agarose gels were identical with those predicted from the known sequences in the database. In addition, the PCR products were verified by DNA sequence analysis. Finally, there was no amplification in the absence of reverse transcriptase, indicating the RNA preparations were not contaminated by genomic DNA (bottom panel). Positions of molecular markers are indicated on the left. D, Effects of the NOS inhibitors on LTH. L-Thiocitrulline (50 μM) and L-NAME (1 mM) were used as described above. n, Number of SNs. The data were normalized to the average excitability of control cells in the same preparation. The asterisk indicates significance ($p < 0.001$), comparing LTH with and without inhibitor by ANOVA and Dunnett's test. Error bars indicate SEM.

FIG. 7A-F. A, Activation of apMAPK in pleural ganglia after nerve crush. Top, Left, Twenty-five micrograms of a pleural ganglia lysate collected at the indicated times after p5-p9 nerve crush were resolved by SDS-PAGE, and a Western blot was probed with Ab pTpYmapk to detect active ERK-MAPKs. The antibody recognized a 43 kDa kinase whose activity was increased on the injured side (I) relative to the contralateral control (CC) 16 hr and later after injury.

Bottom, Left, The injury-activated kinase was apMAPK. The blot was stripped and probed with the D8 antibody, which recognizes both active and inactive apMAPK. D8 recognized the same 43 kDa protein that was recognized by the pTpY antibody. Right, Relative MAPK pTpY was determined by densitometry (Sung et al., 2003). All of the values were normalized to levels of total apMAPK. The ratio of the normalized MAPK pTpY intensity at each time to the normalized naive control is presented. The value for the naive control was arbitrarily set to 1.0. The Western analysis in this figure was performed with the same material used to assess apPKG activity in FIG. 4A. The apMAPK values represent an average of six animals. The line indicates the basal level of apMAPK activity from naive animals. Each of the following experiments (B-E) was repeated twice at least, and representative results are shown. B, apPKG phosphorylates endogenous apMAPK in neurons, but not axoplasm, in vitro. Left, Pleural neurons were removed from a noninjured animal, a lysate was prepared, and 25 µg was incubated with 100 ng of active apPKG protein or with 1 µM 8-Br-cGMP in the presence or absence of 10 µM U0126. Right, Twenty-five micrograms of axoplasm was incubated with active apPKG as above. Active apMAPK was detected by immunoblotting with Ab pTpYmapk. C, apPKG phosphorylates serine-383 in Elk1. One hundred nanograms of apPKG and 0.5 µg of purified recombinant Elk1 protein were incubated with either 5 µg of the pleural neuronal lysate or 0.2 µg of purified recombinant ERK2. Phosphorylated Elk1 (p-Elk1) was detected by probing a Western blot with an antibody that recognizes phosphorylated Ser 383. D, Direct phosphorylation of ERK2 at T183 by apPKG. Two hundred nanograms of recombinant ERK2 was incubated with 100 ng of apPKG in the presence or absence of 1 µg of BPDEtide. The reaction mixture was divided into thirds, a Western blot of each was prepared, and ERK2 was detected with $Ab^{pTpYmapk}$ (top), $Ab^{pYmapk}$ (middle), and $Ab^{pTmapk}$ (bottom), respectively. E, Relative activation of ERK2 by apPKG and MEK1. One hundred nanograms of apPKG, the catalytic subunit of MEKK1, and MEK1 were used as indicated, and the production of phospho-Elk1 was measured with $Ab^{pElk1}$ as shown in C. F, Nerve injury increases the level of apMAPK pY in the cell soma of injured (I) relative to contralateral control (CC) neurons. A Western blot prepared using 25 µg of a pleural neuronal lysate collected at the indicated times after p5-p9 nerve crush was probed with the monospecific pYantibody, $Ab^{pYmapk}$, followed by D8 to detect total apMAPK as in A. The blot shows the results of two animals for each point. N, Lysate from animal without nerve crush.

Figure 8A:
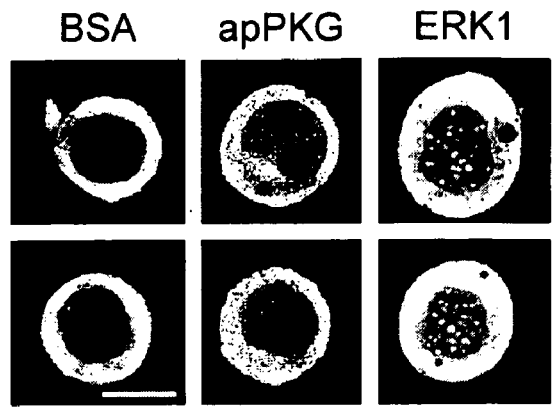
Figure 8B:
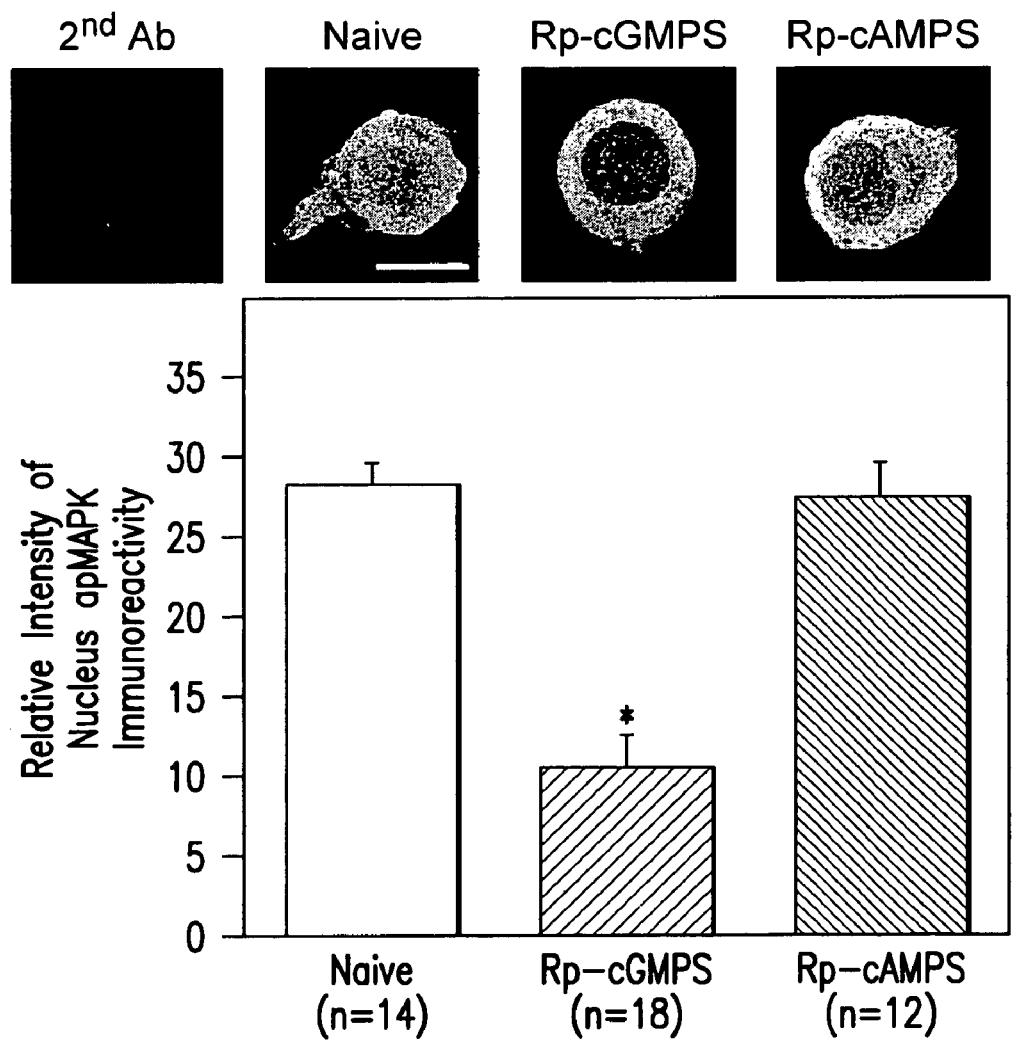

FIG. 8A-B. A, apPKG does not enter the nucleus of SNs. Equal amounts of Alexa Fluor 546-labeled BSA, apPKG, or ERK1 were microinjected into the cytoplasm of SNs after 2 d in vitro. The neurites were then severed with a fine needle to elicit an injury response, and 30 min later, the cells were examined by confocal microscopy. The image is a 2 µm optical section through the center of the cell that shows the nucleus. Scale bar, 20 µm. B, Rp-8-pCPT-cGMPs inhibits axotomy-induced apMAPK nuclear translocation. SNs untreated as controls, and those exposed to either 10 µM Rp-8-pCPT-cGMPs (Rp-cGMPs) or Rp-cAMPs for 2 d in vitro, were immunostained with D8 antibody to localize apMAPK. Top, Representative examples of 2 µm optical sections of control SNs and those exposed to Rp-8-pCPT-cGMPs or Rp-cAMPs. Scale bar, 20 µm. Bottom, Histogram of the mean value of nuclear MAPK immunoreactivity. The staining intensity was determined by a person who was blind to the treatment that the cells received. n, Number of cells for each treatment. Asterisk indicates significant difference from control ($p<0.05$ by ANOVA and Newman-Keuls tests).

Figure 9:
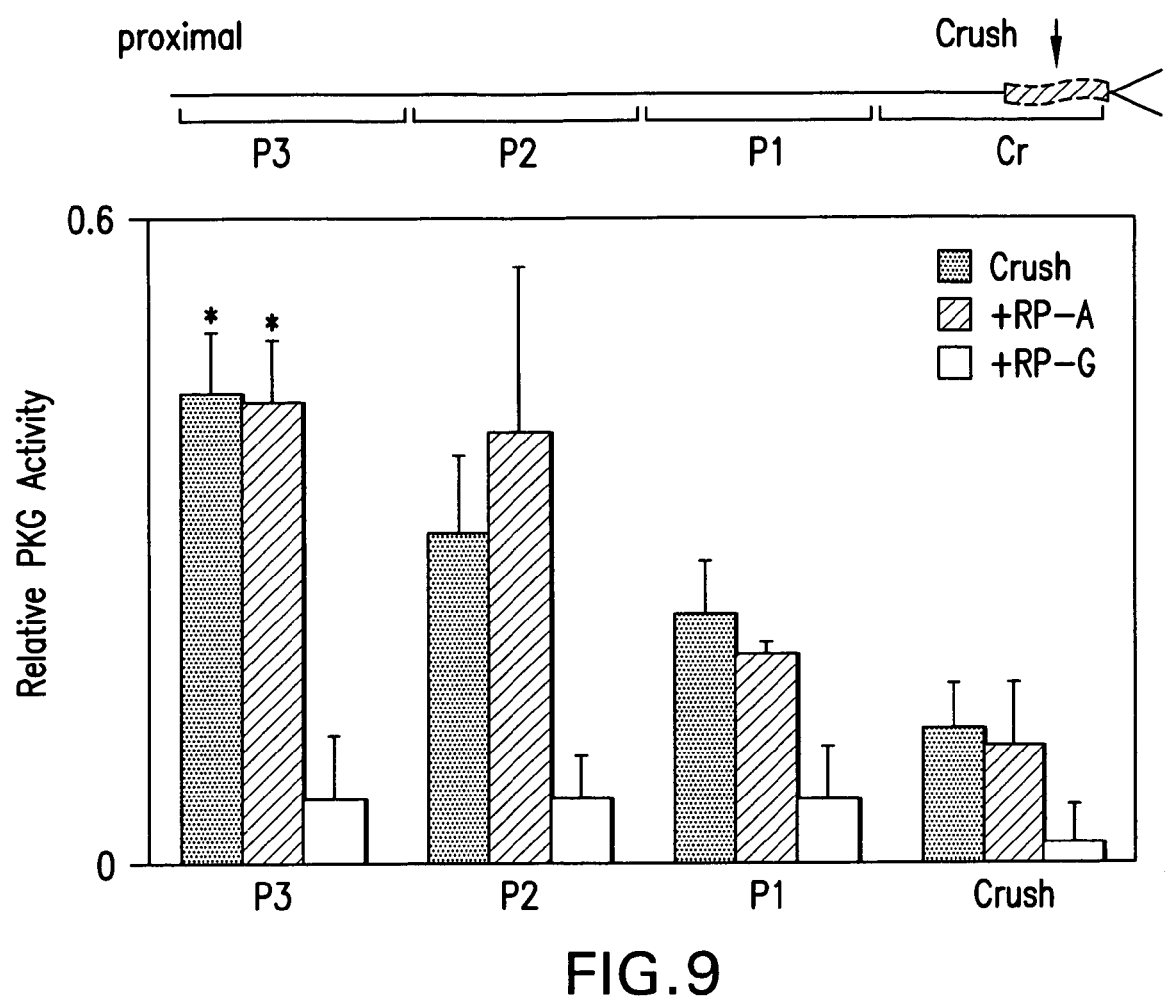

FIG. 9. Relative PKG activity at various positions of the sciatic nerve relative to point of injury, shown schematically above the graph.

Figure 10A:
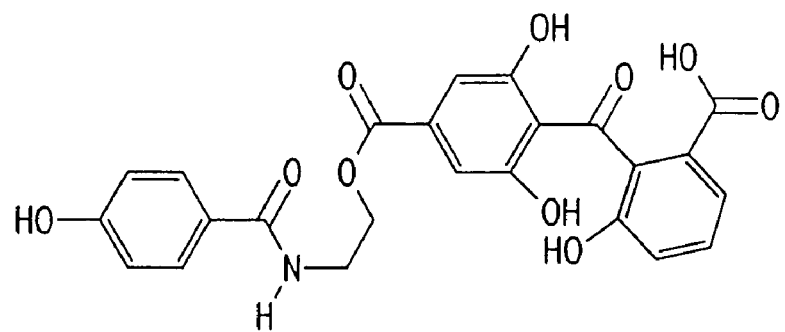
Figure 10B:
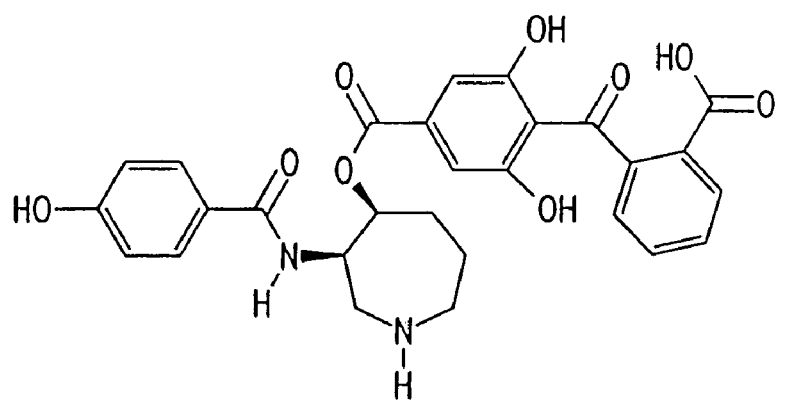
Figure 10C:
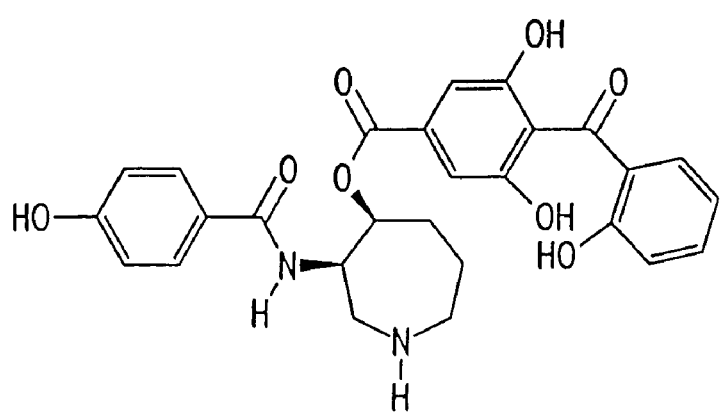

FIG. 10A-C. A. balanol-7R; B. 10" deoxybalanol; C. 14" decarboxy balanol.

Figure 11A:
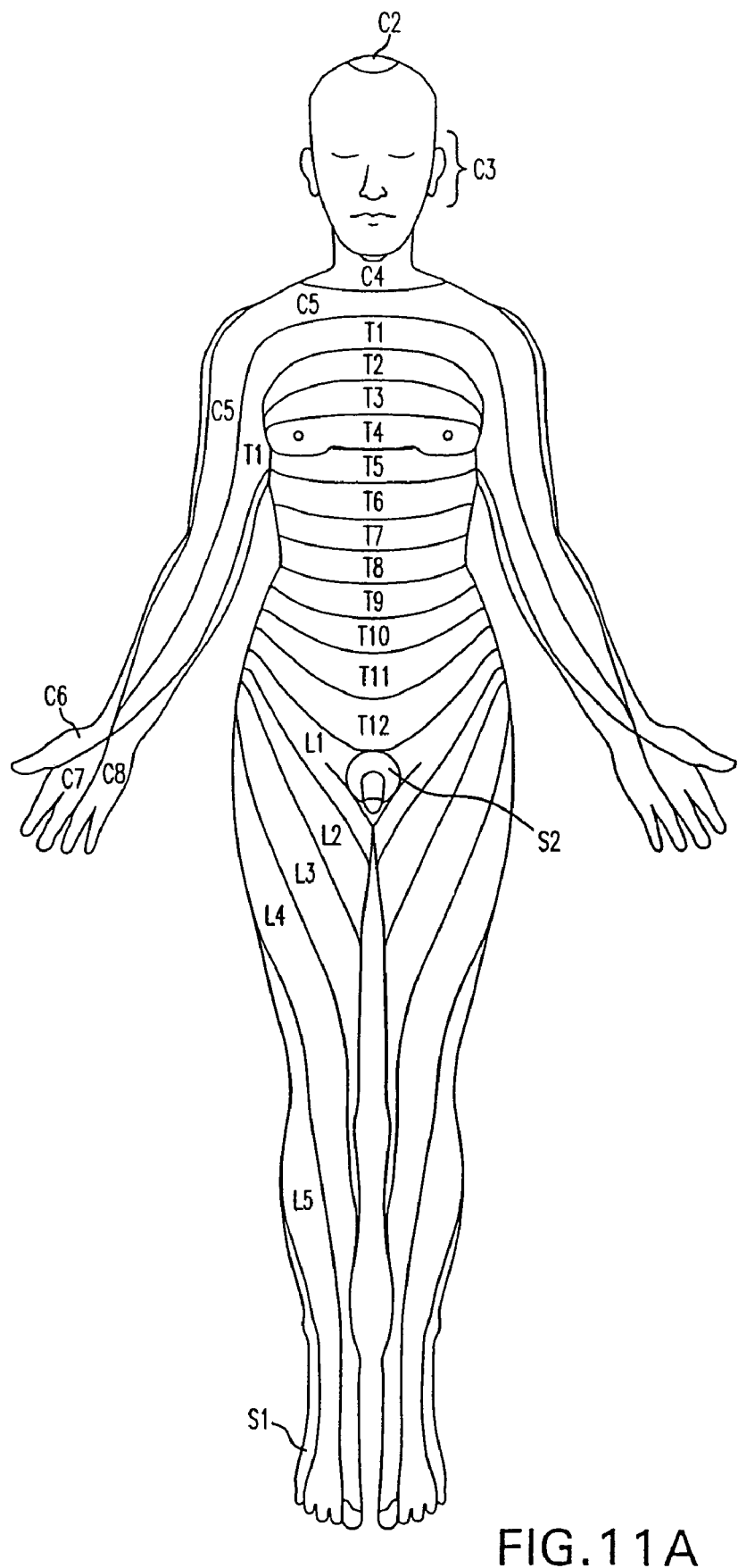
Figure 11B:
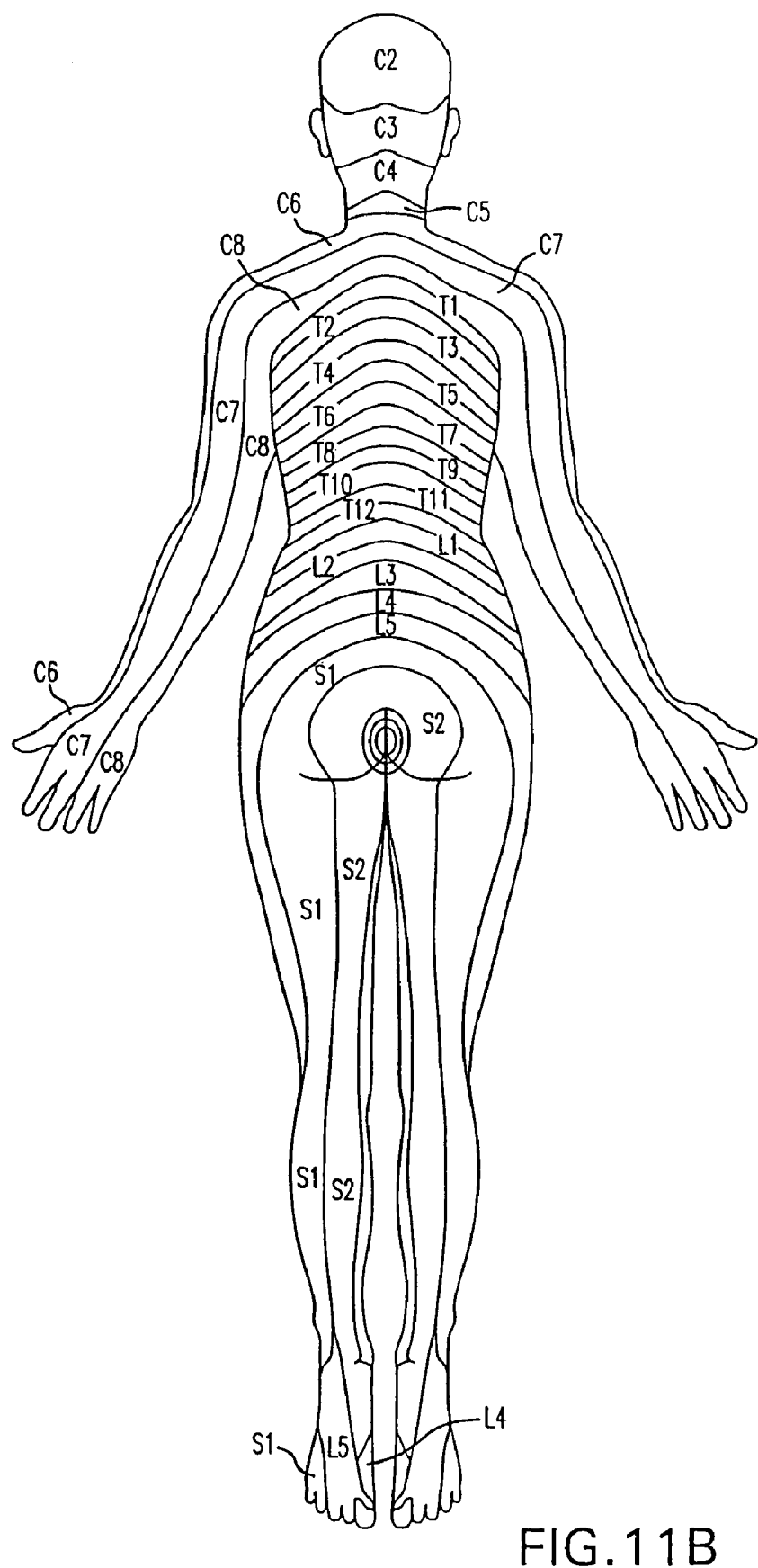

FIG. 11A-B. Surface dermatomes, A. front view, B. back view.

SEQUENCE LISTING

The specification further incorporates by reference the Substitute Sequence Listing submitted herewith via EFS on Mar. 11, 2008. Pursuant to 37 C.F.R. §1.52(e)(5), the Sequence Listing text file, identified as 070053091seqlist2.txt, is 77,465 bytes and was created on Feb. 25, 2008. The Substitute Sequence Listing, electronically filed herewith, does not extend beyond the scope of the specification and thus does not contain new matter.

5. DETAILED DESCRIPTION OF THE INVENTION

For clarity of description, and not by way of limitation, this section is divided into the following subsections:
(i) the NO/cGMP/PKG pathway;
(ii) assays for identifying modulators of the NO/cGMP/PKG pathway; and
(iii) modulating the NO/cGMP/PKG pathway;
(iv) modulation of pain pathways by utilizing neuronal retrograde transport mechanisms; and
(v) apPKG.

5.1 The NO/cGMP/PKG Pathway

The present invention provides a model for the induction of LTH and/or persistent pain in which nerve injury activates neuronal nitric oxide synthase ("nNOS") in the axon, leading to NO production, resulting in the activation of soluble guanylyl cyclase ("GC"), the formation of cyclic guanosine monphosphate ("cGMP"), and the activation of protein kinase G ("PKG"). Activated PKG is retrogradely transported to the cell body of the sensory neurons (SNs) where it activates MAPK-erk in the cytoplasm, which then enters the nucleus and activates transcription of genes responsible for the appearance of LTH and/or persistent pain.

Long-term hyperexcitability ("LTH"), as defined herein, is increased sensitivity of a sensory neuron cell body or axon to stimuli. During electrophysiological testing, LTH is manifested as a decrease in the spike threshold, an increase in repetitive firing, broader spikes, and/or an increase in spike amplitude. In animals that perceive pain, LTH is associated with persistent pain (see Sung and Ambron, Mar. 22, 2004).

Electrophysiological testing may be performed using methods known in the art. One specific, non-limiting example of electrophysiological testing using *Aplysia californica* (hereafter referred to as either "*Aplysia californica*" or simply as "*Aplysia*") SNs may be performed as follows (see Liao et al., 1999). Intracellular recordings from SN somata may be made with glass microelectrodes filled with 3 M potassium acetate (electrode resistance 8-20 M). Recordings may be made at 19-21° C. while the preparation is bathed in buffered artificial sea water ("ASW"), L15 medium, or a 1:1 mixture of ASW and L15, pH 7.6. Soma spike threshold may be measured with a standard series of 20 msec depolarizing pulses. Repetitive firing (spike accommodation) may be quantified by counting the number of spikes evoked by a 1 sec intracellular depolarizing pulse using 2.5 times the threshold current determined with the 20 msec pulse. Repetitive firing may, for example, be examined by counting the number of spikes evoked by a series of 1 sec depolarizing pulses at 1.25, 2.5, and 5 times the threshold current, or by 1, 2, 3, and 5 nA. Input resistance (Rin) may be determined from the voltage change produced during injection of a 1 sec hyperpolarizing pulse (0.5 nA). Axon excitability may be tested by passing current between two compartments through a narrow, Vaseline-sealed opening containing nerves p7, p8, and p9. Threshold may be determined with a rapid series of 2 msec pulses. Repetitive firing may be tested by applying two 1 sec pulses at 0.4 and 0.8 times the 2 msec threshold current.

Persistent pain includes pain that endures longer than the period of acute injury, and includes chronic pain syndromes such as, but not limited to, neuropathic pain (see Bennett et al., 2005). In specific, non-limiting embodiments, the duration of persistent pain is at least 1 day, at least one week, at least one month, or at least one year.

5.2 Assays for Identifying Modulators of the NO/cGMP/PKG Pathway

The present invention provides for assays that identify modulators (inhibitors or promoters/inducers) of the NO/cGMP/PKG pathway. Such assays may be used to evaluate a test agent in order to determine whether the test agent is an agent that modulates at least one step of the pathway and thereby modulates LTH. An inhibitor of the pathway may be used to inhibit LTH and may be used to inhibit and/or treat persistent pain in a sensory neuron and/or a subject. The term "inhibit," as used herein, means lessen, delay, or prevent. A promoter/inducer of LTH may be used to develop a model system for persistent pain, preferably in an animal which, like *Aplysia*, is believed to not subjectively experience pain.

The assays of the invention utilize a model system which comprises a test sensory neuron ("TSN") under physiological conditions which at least approximate the in vivo environment in which the sensory neuron exists in nature. The TSN comprises a cell body that contains the nucleus as well as an axonal segment, which constitutes at least a portion of the TSN's axon and more preferably constitutes the complete axon. In certain non-limiting embodiments, the TSN is an *Aplysia* SN. In other non-limiting embodiments, the TSN is a vertebrate SN, preferably a mammalian SN. The TSN may be maintained isolated in a culture, as part of a group of neurons which may or may not all be SNs, or as an explanted nerve or section thereof (e.g., an excised segment of rat sciatic nerve). In alternate embodiments, the TSN may be retained in an animal in vivo. In still further non-limiting embodiments, the axonal segment may contain at least one ligation.

The TSN is injured. For example, and not by way of limitation, the injury may be created by crushing, cutting and/or chemically injuring the TSN using methods known in the art. Other methods include inducing an inflammatory response, ischemia, a reduction of the blood supply to neurons, and hyperglycemia.

In the assays of the invention, a test agent is administered to the TSN, either prior to, concurrent with, or following injury, either comprised in culture medium, systemically administered, locally injected, or directly injected or otherwise introduced into the TSN. In non-limiting embodiments, the test agent may be administered to a particular cellular location of the TSN, such as the cell body or the axon. Preferably, the effects of the test agent on the TSN are compared to comparable values in a control SN ("CSN"), such as an injured CSN. Thereafter, one of the following evaluation steps is performed. In specific non-limiting embodiments, the evaluation steps are performed within 48 hours of injury.

In a first set of embodiments, the assay of the present invention determines whether the agent modulates nitric oxide synthase ("NOS", which preferably is nNOS, but may also be eNOS and/or iNOS) activity in an injured TSN, preferably relative to NOS activity in an injured CSN to which test agent has not been administered. An ability to inhibit the increase in NOS (preferably nNOS) activity associated with SN injury indicates that the test agent is an LTH inhibitor. An ability to promote a further increase in NOS activity relative to control values indicates that the test agent is an LTH promoter. NOS activity may be measured, for example and not by way of limitation, by measuring either the amount of nNOS mRNA, the amount of nNOS protein, or the amount of nitric oxide ("NO") produced. For example, nNOS mRNA may be measured by PCR amplification, using primers such as oligonucleotides having SEQ ID NOS; 15 and 16, below, or by in situ hybridization using a detectably labeled complementary oligonucleotide probe. For example, nNOS protein may be measured by immunohistochemistry using detectably labeled antibody (polyclonal or monoclonal) specific for nNOS. The amount of NO produced may be measured by, for example, and where the amount of cellular material is sufficient, measuring conversion of L-[$^{14}$C] arginine to L-[$^{14}$C]-citrulline as described in Smith et al., 2002.

In a second set of embodiments, the assay of the present invention determines whether the agent modulates guanylyl cyclase ("GC") activity in an injured TSN, preferably relative to GC activity in an injured CSN to which test agent has not been administered. An ability to inhibit the increase in GC activity associated with SN injury indicates that the test agent is an LTH inhibitor. An ability to promote a further increase in GC activity relative to control values indicates that the test agent is an LTH promoter. GC activity may be measured, for example and not by way of limitation, by measuring either the amount of GC mRNA, the amount of GC protein, or the amount of cGMP produced. For example, GC mRNA may be measured by PCR amplification, using primers designed based on the GC nucleic acid sequence, and GC protein may be measured by immunohistochemistry using detectably labeled antibody (polyclonal or monoclonal) specific for GC. As one non-limiting example, where the volume of cellular material is appropriate, GC activity may be measured by a modification of the method set forth in Mo et al., 2004. For example, TSN may be lysed using a 2-fold concentrated lysis buffer containing 200 μM dithiothreitol and EDTA-free protease inhibitor, and the mixture may be sonicated and kept on ice. The lysed TSN may be assayed in 50 mM Tris-HCl buffer (pH 7.4) supplemented with 3 mM MgCl2, 0.1 mM EGTA, 0.05% (w/v) bovine serum albumin, 1 mM 3-isobutyl-1-methylxanthine, 5 mM creatine phosphate, 200 μg/ml creatine phosphokinase, 300 μM GTP, 1000 units/ml superoxide dismutase, 300 μM uric acid, and 200 μM cPTIO (2-(4-carboxyphenyl)-4,4,5,5-tetramethylimidazoline-1-oxyl-3-oxide). SPER/NO(N-4-1-3-aminopropyl-2-hydroxy-2-nitrosohydrazinobutyl-1,3-propane-diamine) was added, and aliquots may be removed at various intervals, inactivated, and assayed for cGMP. The amount of cGMP produced may be measured by, for example, and where the amount of cellular material is sufficient, by a chemiluminescence assay (HitHunter, Amersham Biosciences Corp., Piscataway, N.J.)

In a third set of embodiments, the assay of the present invention determines whether the agent modulates protein kinase G ("PKG") activity in an injured TSN, preferably relative to PKG activity in an injured CSN to which test agent has not been administered. An ability to inhibit the increase in PKG activity associated with SN injury indicates that the test agent is an LTH inhibitor. An ability to promote a further increase in PKG activity relative to control values indicates that the test agent is an LTH promoter. PKG activity may be measured, for example and not by way of limitation, by measuring the kinase activity in a SN extract. For example, the amount of PKG activity in a SN extract may be determined by measuring the ability of extract to transfer $^{32}$P from [$^{32}$P]-ATP to BPDEtide (Calbiochem, La Jolla, Calif.)

In a fourth set of embodiments, the assay of the present invention determines whether the agent modulates protein kinase G ("PKG") transport in an injured TSN, preferably relative to PKG transport in an injured CSN to which test agent has not been administered. An ability to inhibit the transport of PKG associated with SN injury indicates that the test agent is an LTH inhibitor. An ability to promote a further increase in PKG transport relative to control values indicates that the test agent is an LTH promoter. PKG transport may be measured, for example and not by way of limitation, by determining whether an increase in PKG activity moves, over time, from the region of the SN that is injured toward the cell body. This increase may be measured by a number of methods, including, but not limited to, testing sequential, distal to proximal, axonal segments for PKG activity (see FIG. 9). In another non-limiting example, the axonal segment may be ligated and axonal material may be collected from regions of the axon at different relative distances from the injury and/or ligation, where, for example, the amount of activated PKG in the region of the injury becomes less, over time, relative to the amount of PKG activity on the side of the ligation facing the injury (see FIG. 4).

In a fifth set of embodiments, the assay of the present invention determines whether the agent modulates phosphorylation of mitogen-activated protein kinase-erk ("MAP-Kerk") in an injured TSN, preferably relative to phosphorylation of MAPKerk in an injured CSN to which test agent has not been administered. An ability to inhibit phosphorylation of MAPKerk associated with SN injury indicates that the test agent is an LTH inhibitor. An ability to promote a further increase in phosphorylation of MAPKerk relative to control values indicates that the test agent is an LTH promoter. Phosphorylation of MAPKerk may be measured by determining the level of MAPKerk activity in phosphorylating its substrate, or by detecting the presence of phosphorylated MAP-Kerk using an antibody that selectively binds to phosphorylated rather than unphosphorylated protein (for example, but not by way of limitation $Ab^{pTpYmapk}$.

In a sixth set of embodiments, the assay of the present invention determines whether the agent modulates MAPKerk translocation into the nucleus of an injured TSN, preferably relative to MAPKerk translocation into the nucleus of an injured CSN to which test agent has not been administered. An ability to inhibit MAPKerk translocation into the nucleus associated with SN injury indicates that the test agent is an LTH inhibitor. An ability to promote a further increase in MAPKerk translocation into the nucleus relative to control values indicates that the test agent is an LTH promoter. MAPKerk translocation into the nucleus may be measured by using a MAPKerk-specific antibody to measure the amount of MAPKerk in the SN nucleus using laser confocal immunohistochemical techniques.

5.3 Modulating the NO/cGMP/PKG Pathway

According to the present invention, the NO/cGMP/PKG pathway, and thereby the development of LTH and persistent pain, may be modulated using inhibitors disclosed in this section or promoters/inducers identified or having the properties set forth in the preceding section 5.2. In particular embodiments, an inhibitor may be administered to a sensory neuron in need of such treatment in an amount effective in inhibiting LTH. Where the SN to which the inhibitor is to be administered is a SN in vivo in an animal subject, the inhibitor may be administered systemically (e.g. by intravenous injection, oral administration, inhalation, etc.), may be injected locally (in proximity to the damaged nerve), may be applied topically (for example, together with a skin permeability enhancing agent, such as a chemical compound or an electrical stimulus) or may be administered by any other means known in the art, except that introduction into the central nervous system, such as intrathecal administration, would not be used to administer inhibitor to a SN. The amount of inhibitor to be administered may be determined using methods known in the art, for example, by doing dose response studies in one or more model system, such as the *Aplysia* system described above or a mammalian model of peripheral neuropathic pain, followed by approved clinical testing in humans. Where concentrations are set forth below, they refer to the concentration to which the sensory neuron or any component thereof, including axon, cell body or receptor, is exposed.

In related embodiments, an effective amount of an inhibitor may be administered to a subject in need of such treatment, where the subject suffers from chronic pain. The chronic pain preferably has a peripheral nervous system (primary) hyperalgesia component, where the method inhibits pain mediated by the peripheral nervous system, but in specific non-limiting embodiments the present invention also encompasses the treatment of spinal hyperalgesia as either a component of or the basis of (e.g., chronic central neuropathic pain resulting from spinal cord injury) chronic pain. Any of the foregoing modes of administration may be used, but if a spinal hyperalgesia component is to be treated, the inhibitor, which is directed to a neuron having its cell body in the central nervous system and not in the dorsal root ganglion, should be administered intrathecally.

An effective amount is an amount of inhibitor which decreases the level of pain subjectively perceived by the subject, preferably amount determined, in controlled experiments, which is greater than placebo effect. For example, and not by way of limitation, in certain embodiments of the invention, where perceived pain can be quantified on a scale from 0 to 10, where 0 is no pain, 1-5 is progressively more intense mild pain, 6-7 is progressively more intense moderate pain, 8-9 is progressively more intense severe pain, and 10 is the worst pain possible, an effective amount of inhibitor may decrease the pain scale quantification of perceived pain by at least 2 points, or by at least 3 points.

In specific, non-limiting embodiments, the present invention provides for a method for treating chronic pain in a subject comprising administering, to the location from which the pain arises, an effective amount of an inhibitor as set forth herein (alternatively referred to as an "LTH inhibitor"), where administration can be by local injection or topical application (e.g., via a cream, ointment, or transdermal device, which may be a patch or may be an apparatus or an apparatus containing or otherwise associated with a patch), and the location can be, as non-limiting examples, a wound site, tissue overlying an inflamed joint, or an area within the dermatome associated with the perceived pain (e.g., L4, L5, S1, C3, C4, C5, C6 or C7, see below).

5.3.1 Modulation of NOS

In one specific non-limiting embodiment, the present invention provides for inhibiting the NO/cGMP/LTH pathway, LTH, and/or persistent pain, by a method comprising administering, to a SN (which may or may not be a SN in vivo in a subject), an effective amount of an inhibitor of NOS (preferably nNOS, and/or eNOS and/or iNOS), such as, but not limited to, L-NAME [N$^G$-nitro-L-arginine methyl ester hydrochloride], L-thiocitrulline, or an antisense nucleic acid or RNAi that inhibits NOS expression. Such an antisense nucleic acid molecule or RNAi may hybridize to the target NOS under stringent hybridization conditions, as defined below.

5.3.2 Modulation of NO Levels

In another specific non-limiting embodiment, the present invention provides for inhibiting the NO/cGMP/LTH pathway, LTH, and/or persistent pain, by a method comprising administering, to a SN (which may or may not be a SN in vivo in a subject), an effective amount of an agent which decreases NO levels, including, but not limited to, quercetin (which is an NO scavenger (Griffiths et al., 2003)).

5.3.3 Modulation of GC

In another specific non-limiting embodiment, the present invention provides for inhibiting the NO/cGMP/LTH pathway, LTH, and/or persistent pain, by a method comprising administering, to a SN (which may or may not be a SN in vivo in a subject), an effective amount of an agent that inhibits the increase in GC activity, such as, but not limited to, L-H-[1,2,4]oxadiazolo[4,3-a]quinoxalin-1-one ("ODQ"), or an antisense nucleic acid molecule or RNAi that inhibits expression of GC. Such an antisense nucleic acid molecule or RNAi may hybridize to the target GC under stringent hybridization conditions, as defined below.

5.3.4 Modulation of cGMP Levels

In another specific non-limiting embodiment, the present invention provides for inhibiting the NO/cGMP/LTH pathway, LTH, and/or persistent pain, by a method comprising administering, to a SN (which may or may not be a SN in vivo in a subject), an effective amount of an agent that decreases cGMP levels, such as, but not limited to, an agent that increases phosphodiesterase, preferably PDE5, activity, such as, but not limited to, administering phosphodiesterase (e.g. PDE5) itself, or the PDE5 activator Ant-cGMP-2'-O-anthranyloyl cGMP (Guanosine 3',5' cyclic monophosphate, 2'-O-anthraniloyl cGMP).

5.3.5 Modulation of PKG Activity

In another specific non-limiting embodiment, the present invention provides for inhibiting the NO/cGMP/LTH pathway, LTH, and/or persistent pain, by a method comprising administering, to a SN (which may or may not be a SN in vivo in a subject), an effective amount of an agent that inhibits PKG activity. In specific, non-limiting embodiments, the agent inhibits activated PKG and/or its arrival from the axon in a neuronal cell body.

In non-limiting embodiments, the agent is a peptide inhibitor of PKG. Non-limiting examples of peptide inhibitors of PKG are disclosed in Dostmann, 2000, and include a peptide comprising the sequence LRKKKKKH (SEQ ID NO:26), LRAKKKKH (SEQ ID NO:27), LRKAKKKH (SEQ ID NO:28), LRKKAKKH (SEQ ID NO:29), LRKKKAKH (SEQ ID NO:30) or LRKKKKKH (SEQ ID NO:31). In other embodiments, a peptide inhibitor of PKG may comprise a core sequence, RKK or RKKK (SEQ ID NO:32), and may be between about 5 and 100, or between 5 and 50, or between 10 and 30, or between 10 and 20, amino acids long.

A peptide inhibitor of PKG according to the invention may further comprise one or more transport peptide, one or more carrier peptide, or both transport and carrier peptides, as well as additional peptide or non-peptide components which may improve transport, effectiveness, and/or stability. Thus, the present invention provides for peptides comprising inhibitor-Δ-carrier, carrier-Δ-inhibitor, inhibitor-Σ-transport, transport-Σ-inhibitor, carrier-Δ-inhibitor-Σ-transport, and transport-Σ-inhibitor-Δ-carrier, where Δ and Σ are optional linker peptides, carrier is a carrier peptide, inhibitor is an inhibitor peptide, and transport is a transport peptide, as set forth herein, where in non-limiting embodiments the size of the entire peptide is between 10 and 100, or between 10 and 50, or between 10 and 30 amino acids long. In specific, non-limiting embodiments of the invention, the present invention provides for peptides comprising LRKKKKKH-ΔYGRKKRRQRRRPP (SEQ ID NO:33), YGRKKRRQR-RRPPΔLRKKKKKH (SEQ ID NO:34), LRKKKKKHΔR-QIKIWFQNRRMKWKK (SEQ ID NO:35), RQIKIWFQNRRMKWKKΔLRKKKKKH (SEQ ID NO:36), LRKKKKKHΣPKKKRK (SEQ ID NO:37), PKKKRKΣLRKKKKKH (SEQ ID NO:38), YGRKKRRQRRRPPΔLRKKKKKHΣPKKKRK (SEQ ID NO:39), PKKKRKΣLRKKKKKHΔYGRKKRRQRRRPP (SEQ ID NO:40), RQIKIWFQNRRMKWKKΔL-RKKKKKHΣPKKKRK (SEQ ID NO:41), PKKKRKΣL-RKKKKKHΔRQIKIWFQNRRMKWKK (SEQ ID NO:42), where Δ and Σ are optional linker molecules of between 0 and 5, or between 0 and 10, or between 0 and 20, amino acids, which peptides may be between 5 and 100, or between 5 and 50, or between 10 and 30 amino acids long. The present invention further provides for peptide inhibitors which are at least about 90 or about 95 percent homologous to the above-recited peptides, as determined using standard homology assessing software such as BLAST or FASTA, and which inhibit PKG, and which may be between about 5 and 100, or between 5 and 50, or between 10 and 30, or between 10 and 20, amino acids long. In specific, non-limiting embodiments, the effective concentration of peptide inhibitor may be between 1 nanomolar and 10 micromolar.

In other non-limiting embodiments, the inhibitor of PKG is a compound of formula I, as set forth below:

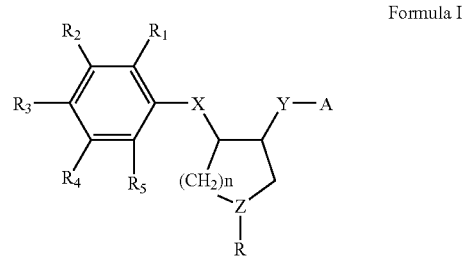

Formula I

In Formula I, n is 1, 2 or 3; Z is N or CH

In Formula I, X represents one of the following functional groups:

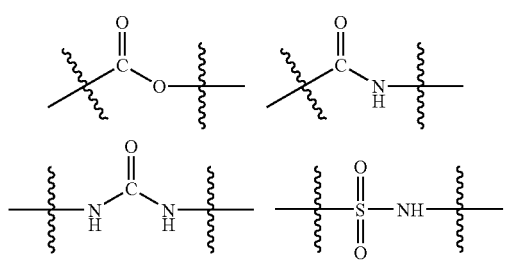

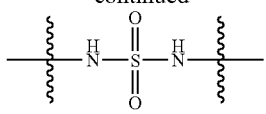

In Formula I, Y represents one of the following functional groups:

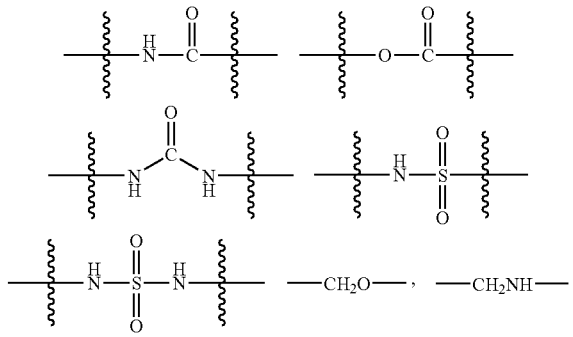

In Formula I, A represents aryl or heteroaryl groups unsubstituted or substituted by one or more lower-alkyl, lower-alkoxy, hydroxy, alkoxy, amino, alkylamino or halogen groups. Examples of the aryl or heteroaryl groups are listed below:

When Y is:

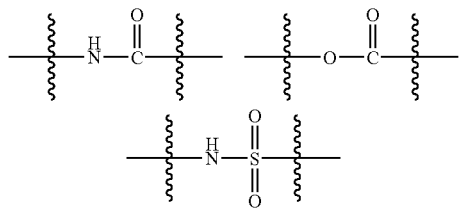

A is:

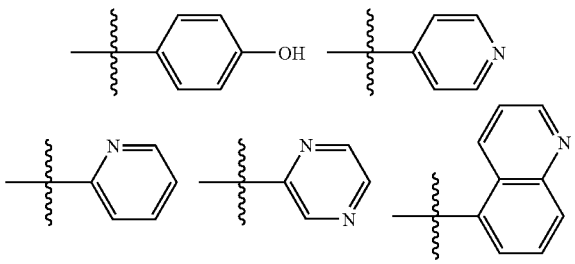

When Y is:

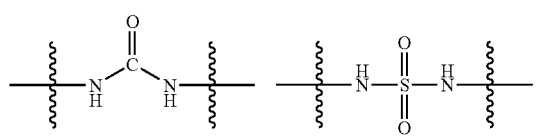

A is:

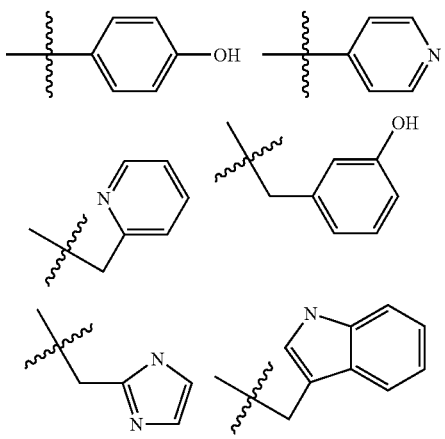

In Formula I, R is hydrogen, lower-alkyl, or amidino.

In Formula I, R1, R2, R4, R5 is independently hydrogen, hydroxyl, lower-alkoxy, amino, halogen.

In Formula I, R3 is alkyl, aryl, heteroaryl, alkoxy, aryloxy, or one of the groups listed below:

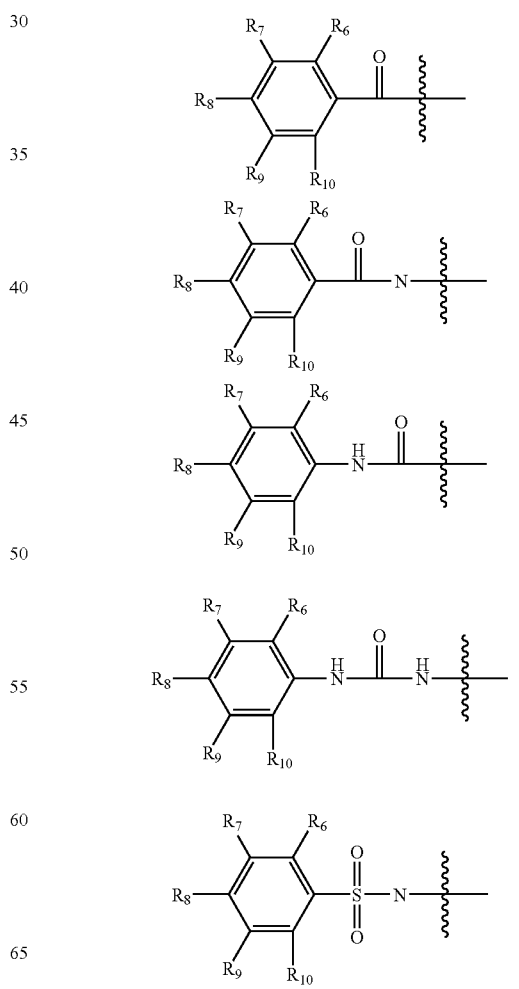

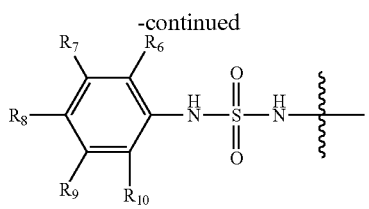

where R6-R10 are independently hydrogen, hydroxy, lower-alkyl, lower-alkoxy, halogen, trifluoromethyl, carboxy, alkoxycarbonyl, amino, alkylamino, alkylcarbonylamino, alkylsulfonylamino (e.g. $CF_3SO_2NH-$, $CH_3SO_2NH-$), tetrazole. In one specific, non-limiting embodiment, the compound of formula I is balanol or a derivative thereof, as disclosed in Internation Patent Application No. PCT/US92/07124, Publication No. WO93/03730, where balanol has formula Ia, as follows:

Formula Ia

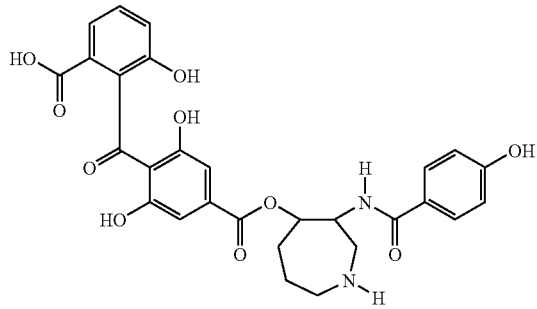

In particular nonlimiting embodiments of the invention, Formula Ia may be varied to provide "balanol variants" which inhibit PKG. Non-limiting examples of such balanol variants include balanol-7R, 14" decarboxy balanol, and 10" deoxybalanol, as set forth in FIG. 10A-C, which are inhibitory of PKG at concentration of 291, 19 and 31 nM, respectively, where balanol is inhibitory at 1.6 nM (see Setyawan et al., 1999).

The present invention further provides for molecules of Formula I, Formula Ia, and balanol variants which are conjugated to one or more carrier peptide, one or more transport peptide, or one or more carrier peptide and one or more transport peptide (also referred to as balanol variants, or balanol double variants). In specific non-limiting embodiments, the concentration of balanol or balanol variant administered to the neuron, for example via its axon, may be between about 1 and 500 nM, or between about 2 and 100 nM, depending on the potency of the compound.

In another specific, non-limiting embodiment, the agent is Rp-8-pCPT-cGMPS. In a related embodiment, the agent is Rp-8-pCPT-cGMPS conjugated to one or more transport peptide. In another related embodiment, the agent is Rp-8-pCPT-cGMPS conjugated to one or more carrier peptide. In yet another related embodiment, the agent is Rp-8-pCPT-cGMPS conjugated to both one or more transport peptide and one or more carrier peptide. (see below for definition of transport and carrier peptides). In specific, non-limiting embodiments, the concentration of Rp-8-pCPT-cGMPs may be between 1 micromolar and 500 micromolar.

In another specific, non-limiting embodiment, the agent is an antisense nucleic acid molecule or RNAi that inhibits expression of PKG. Such an antisense nucleic acid molecule or RNAi may hybridize to the target PKG under stringent hybridization conditions, as defined below.

5.3.6 Modulation of PKG Transport

In another specific non-limiting embodiment, the present invention provides for inhibiting the NO/cGMP/LTH pathway, LTH, and/or persistent pain, by a method comprising administering, to a SN (which may or may not be a SN in vivo in a subject), an effective amount of an agent that inhibits PKG transport.

In non-limiting embodiments of the invention, an agent that inhibits PKG transport may comprise a transport peptide, as set forth below, in an amount effective to inhibit the axonal retrograde transport system. In non-limiting specific embodiments, an agent that inhibits PKG transport may comprise a plurality of transport peptides, for example, but not by way of limitation, comprised in surface loops of a decoy molecule.

5.3.7 Modulation of MAPKerk Activity

In another specific non-limiting embodiment, the present invention provides for inhibiting the NO/cGMP/LTH pathway, LTH, and/or persistent pain, by a method comprising administering, to a SN (which may or may not be a SN in vivo in a subject), an effective amount of an agent that inhibits activation (phosphorylation) of MAPKerk. Such molecules include, but are not limited to, tyrosine kinase inhibitors such as K252a and genistein.

5.3.8 Modulation of MAPKerk Transport

In another specific non-limiting embodiment, the present invention provides for inhibiting the NO/cGMP/LTH pathway, LTH, and/or persistent pain, by a method comprising administering, to a SN (which may or may not be a SN in vivo in a subject), an effective amount of an agent that inhibits translocation of MAPKerk into the nucleus, including, but not limited to, a calcium antagonist such as felodipine (Yang et al., 2002), verapamil, diltiazem, nifedipine, etc., or apolipoprotein D (Sarjeant et al., 2003).

5.3.9 Compositions for Treating Pain

Compositions of the invention may comprise an inhibitor agent as described above, where the inhibitor agent optionally comprises a carrier molecule which facilitates its translocation through a neuronal cell or nuclear membrane. Examples of carrier molecules which may be used include but are not limited to HIV-1 tat protein (YGRKKRRQRRRPP; SEQ ID NO:43) and peptides that are about 9-30 or about 9-20 residues long comprising its cores sequence RKKRRQRRR (SEQ ID NO:44), *Drosophila* Antennapedia homeo-domain (RQIKIWFQNRRMKWKK; SEQ ID NO:45). Other carrier molecules that may be used according to the invention may be largely comprised (contain at least 60 percent, at least 70 percent, or at least 80 percent) of positively charged amino acids such as arginine (Wender et al., 2000) and/or lysine (Mai et al., 2002). Also encompassed by the invention are peptides and derivatized peptides which are at least about 90 or about 95 percent homologous to the above-recited peptides, as determined using standard homology assessing software such as BLAST or FASTA. The inhibitor agent may optionally alternatively or additionally comprise a transport peptide, as described below.

The present invention provides for such inhibitor agents, in either lyophilized form or dissolved in a suitable pharmaceutical carrier. Compositions that comprise more than one inhibitor agent are encompassed by the invention.

In non-limiting embodiments, the invention provides for a pharmaceutical composition comprising one or more inhibitor agent, as set forth above, together with at least one agent that promotes uptake of the inhibitor agent into a peripheral nerve. Examples of such agents include membrane permeability enhancing agents such as dimethyl sulfoxide and/or 2 hydroxypropyl-b-cyclodextrin.

In other non-limiting embodiments, the invention provides for a pharmaceutical composition comprising one or more inhibitor agent, as set forth above, together with at least one agent that treats an underlying cause of the pain, including, but not limited to, an anti-inflammatory agent (such as aspirin, a non-steroidal anti-inflammatory agent such as ibuprofen, or a corticosteroid).

In other non-limiting embodiments, the invention provides for a pharmaceutical composition comprising one or more inhibitor agent, as set forth above, together with at least one agent having a local anesthetic effect, such as lidocaine.

In a further non-limiting embodiment, the present invention provides for a transdermal device, such as a patch or apparatus comprising one or more inhibitor agent, as set forth above, and optionally one or more additional agent which promotes the uptake of agent in a peripheral nerve, treats an underlying cause of the pain, and/or has local anesthetic effect, where exemplary compounds in each of these categories is provided above. The device may in general utilize transdermal patch technology known in the art, to facilitate sustained release of its therapeutic agents through the skin of a subject. In specific, non-limiting embodiments, the device creates an electrical potential which promotes uptake of the inhibitor agent(s) into local tissue (iontophoresis) or improves drug transfer using ultrasound or radiofrequency waves (see Bryan, 2004; U.S. Pat. No. 5,405,614, U.S. Pat. No. 4,708,716).

5.4 Modulation of Pain Pathways by Utilizing Neuronal Retrograde Transport Mechanisms The present invention provides for a method for modulating and specifically inhibiting pain pathways, the perception of pain and primary (peripheral nervous system) hyperalgesia, comprising delivering a pain inhibitor compound to an axon of a sensory nerve such that the pain inhibitor compound is retrogradely transported along the axon to the sensory neuron cell body in the dorsal root ganglion. According to this embodiment of the invention, the pain inhibitor compound is not limited to the LTH inhibitors set forth herein, but may be any pain inhibitor that operates on sensory neurons, such as prostaglandin inhibitors (e.g., COX-2 inhibitors), peripherally acting opioids, anesthetic compounds, etc., linked to a transport peptide which facilitates retrograde axonal transport.

In one non-limiting example, the transport peptide is PKKKRK (SEQ ID NO:46), or a peptide or derivatized peptide which is at least about 80 percent homologous thereto as determined using standard homology assessing software such as BLAST or FASTA and which facilitate axonal transport. In another non-limiting example, the transport peptide is the related peptide CTPPKKKRKV (SEQ ID NO:47)(see Ambron, 1992), or a peptide or derivatized peptide which is at least about 70, at least about 80, or at least about 90 percent homologous thereto as determined using standard homology assessing software such as BLAST or FASTA and which facilitate axonal transport. In specific, non-limiting embodiments of the invention, the transport peptide is between 5 and 20 amino acids long and comprises the peptide KKKRK (SEQ ID NO:48), PKKKRK (SEQ ID NO:46), PPKKKRK (SEQ ID NO:49), TPPKKKRK (SEQ ID NO:50), or PKKKRKV (SEQ ID NO:51).

For example, the pain inhibitor compound (comprising an agent that inhibits pain associated with a sensory neuron and a transport peptide; preferably an LTH inhibitor as set forth above) may be delivered to a peripheral pain receptor at the site of injury or in the same dermatome as the injury, as sensory axons arising throughout the dermatome converge on the same dorsal root ganglion. FIG. 11A-B presents the sensory dermatomes (from The Merck Manual of Diagnosis and Therapy, Section 14, Chapter 165, FIG. 165-2, which references Keegan J J and Garrett F D, "Anatomical Record 102: 409-437, 1948, used with permission of the Wistar Institute, Philadelphia, Pa.). As examples, arthritis pain associated with the fingers is communicated via axons whose cell bodies reside in DRGs at levels C5-T1 and pain from the knees is communicated via axons whose cell bodies reside in DRGs at levels L3-S2.

Accordingly, the present invention provides for a method of treating pain in a subject, where the pain is determined to be associated with a dorsal root ganglion at a particular spinal cord level, comprising topically applying a pain inhibitor comprising a transport peptide to skin lying within the dermatome corresponding to the spinal cord level associated with the pain.

The pain inhibitor compound may be comprised in a cream, ointment, or transdermal device (see above), applied to the appropriate dermatome.

For example, a person suffering from lower back pain as a result of compression of the nerve exiting a bony foramen in the lower spine (lumbar, sacral, or lumbosacral radiculopathy) could be treated with a transdermal patch containing a pain inhibitor compound (comprising a transport peptide) applied to the dermatome corresponding to the spinal cord level from which the compressed nerve originates, which may be identified by the person's symptoms and physical exam. As one specific example, because the radiculopathy often involves nerves that supply the L4, L5 and/or S1 dermatomes, a transdermal patch according to the invention may be applied to the buttock of the patient. As another specific non-limiting example, a person having arthritis involving the finger joints, dermatomes C6-C8, could wear a patch according to the invention on the upper arm or shoulder, for example above the spine of the scapula.

This aspect of the invention provides the advantage that it treats pain while avoiding systemic administration of antinociceptive compound, thereby decreasing substantially the potential for substance abuse and avoiding potential side effects, such as those associated with COX-2 inhibitors.

5.5 apPKG

The present invention further provides for nucleic acid molecules encoding protein kinase G as well as their encoded proteins.

In certain non-limiting embodiments, the present invention provides for an isolated nucleic acid that encodes a protein kinase G of *Aplysia* having the amino acid sequence set forth in GenBank Acc. No. AY362340 and SEQ ID NO:10 herein. In particular embodiments, the present invention provides for an isolated nucleic acid molecule having a sequence as set forth in GenBank Acc. No. AY362340 and SEQ ID NO:9 herein, as well as nucleic acid molecules that are at least 85, at least 90, or at least 95 percent homologous thereto, where homology is determined by standard homology determining software such as BLAST or FASTA. The present invention further provides for isolated nucleic acid molecules that hybridize to a nucleic acid molecule having SEQ ID NO:9 under stringent conditions, and that encode a molecule having protein kinase activity. Stringent conditions are defined herein as hybridization to filter-bound DNA in 0.5 M NaHPO4, 7% sodium dodecyl sulfate (SDS), 1 mM EDTA at 65° C., and washing in 0.1×SSC/0.1% SDS at 68° C. (Ausubel F. M. et al., eds., 1989, Current Protocols in Molecular Biology, Vol. I, Green Publishing Associates, Inc., and John Wiley & sons, Inc., New York, at p. 2.10.3).

The nucleic acids of the invention may be comprised in a vector molecule, which may be a phage, plasmid, phagemid, or virus.

The nucleic acids of the invention may be operably linked to a promoter element to create an expression cassette.

The present invention further provides for an isolated protein having a sequence as set forth in SEQ ID NO:10, as well as proteins that are at least 85, at least 90, or at least 95 percent homologous thereto and exhibit protein kinase activity. The proteins of the invention may be comprised in fusion proteins. As one non-limiting example, the proteins of the invention may be fused to an immunologically recognizable tag, such as a His tag (see Section 6, below).

In further embodiments, the present invention provides for an isolated protein comprising the catalytic portion of apPKG, including a catalytic portion of apPKG having the amino acid sequence:

```
VAKEFENCSLDDLQLVTTLGMGGFGRVELVQLSKEK (SEQ ID NO:25)
GKTFALKCLKKKHIVETRQQEHIYSEKKIMMEADSP
FITKLHKTFRDRKYVYMLMEVCLGGELWTILRDRGN
FDDLTARFCVACVLEAFSYLHAKGIIYRDLKPENLL
LDARGYVKLVDFGFAKKIGVGKKTWTFCGTPEYVAP
EIILNKGHDHSADYWSLGILMYELLNGTPPFSGSDP
MRTYNIILKGIDHIEFPKKISRSAHVLIKKLCRDNP
MERLGYGKNGISDIRKNKWF,
``` and amino acid sequences that are at least 85 percent, at least 90 percent, or at least 95 percent homologous thereto. The catalytic portion of apPKG, and molecules that are at least 85, at least 90, or at least 95 percent homologous thereto, may be comprised in a fusion protein, linked to another amino acid sequence at the N and/or C terminal end. The present invention further provides for isolated nucleic acid molecules encoding said isolated proteins, which may be operably linked to a promoter element comprised in an expression cassette and/or a vector molecule.

The present invention further provides for antibody molecules that are prepared by immunizing an animal with a purified protein according to the invention. Such antibody molecules may be polyclonal or monoclonal, prepared using standard laboratory techniques.

6. EXAMPLE

A Neuronal Isoform of Protein Kinase G Couples Mitogen-Activated Protein Kinase Nuclear Import to Axotomy-Induced Long Term Hyperexcitability in *Aplysia* Sensory Neurons

6.1 Materials and Methods

In vivo nerve crush. *Aplysia* (100-150 gm) were anesthetized with isotonic MgCl2, and a small incision was made on one side of the body wall. Pedal nerves 5-9 were crushed 2 cm from the pedal-pleural ganglia on one side. The wound was sutured, and the animal was returned to its tank. The crush-ligation protocol followed was as described (Ambron et al., 1995).

Cloning. Degenerate oligonucleotide primers 5'-tayaaytgyacnmgiacngc (SEQ ID NO:1) and 5'-ccrcaraangtccangtytt (SEQ ID NO:2) were used to amplify an apPKG cDNA fragment from *Aplysia* CNS cDNA. The resulting PCR product from this amplification was cloned into pCR-II (Invitrogen, Carlsbad, Calif.) and subsequently sequenced by the core facility at Columbia University. The 5' end and 3' end of the cDNA were cloned using 5'-rapid amplification of cDNA ends (RACE) and 3'-RACE, respectively. A Marathon cDNA Amplification kit (BD Clontech, Palo Alto, Calif.) was used to generate cDNA from *Aplysia* CNS poly(A+) RNA according to the manufacturer's instructions. For the 5'-RACE reaction, a specific primer, 5'-cgcctgtccagcacccatagcg (SEQ ID NO:3), was used. The product of this PCR reaction was then confirmed by a second amplification using a nested, specific 5' primer, 5'-gggtgaccgctttcacggagg (SEQ ID NO:4). For the 3'-RACE reaction, a specific primer, 5'-cggcaaggttctgcgtcgcc (SEQ ID NO:5), was used. The PCR product was then subjected to a second amplification using a nested, 3' primer, 5'-ggacgcgaggggatacgtc (SEQ ID NO:6). Both 5'- and 3'-RACE products were subcloned into pCR-II and sequenced. To obtain the full-length cDNA in one piece, another PCR was performed with oligonucleotides 5'-ggtg-gaggagatagcggcggttctgtgaacgcc (SEQ ID NO: 7) and 5'-ggaggagtgagggtcagatcc (SEQ ID NO:8), corresponding to the 5' and 3' ends of 5'- and 3'-RACE products, respectively. The PCR product was sequenced and designated apPKG and was deposited in the GenBank database under accession number AY362340 (SEQ ID NO:9) The deduced amino acid sequence is SEQ ID NO:10.

Sequence analysis. Sequence alignment of various PKGs and identification of conserved residues was performed using the Clustal W and box-shade algorithms provided in the suite of programs available from Biology Workbench. Protein expression and purification. A His tag was added to the N terminus of the apPKG-coding region by PCR amplification from *Aplysia* CNS cDNA with the following primers: 5'-tg-gcggccgctcatgagaggatcgcatcac-catcaccatcacggcaacggtgccagttcgaacacgcacttc (SEQ ID NO:11) and 5'-gcaggctctagagaaatcaatgtcccagccggataactcgtc (SEQ ID NO:12). The PCR product was subcloned into the NotI and XbaI sites of pFasBac-1 (Invitrogen) and was subsequently confirmed by sequencing. The resulting construct pFB1apPKG contains an N-terminal histidine epitope tag. Transformation of pFB1apPKG into Max Efficiency DH10Bac cells (Invitrogen), identification of recombinant clones, and isolation of the recombinant baculovirus shuttle vector DNA (bacmid) were performed according to the manufacturer's instructions (Invitrogen). Recombinant baculovirus was obtained by transfecting Sf9 cells (*Spodoptera frugiperda*), which were propagated as monolayers at 27° C. in Sf-900 IISFM medium (Invitrogen) containing 100 U/ml penicillin (Invitrogen) and 0.1 mg/ml streptomycin (Invitrogen). Transfection with recombinant bacmid DNA was performed using CellFectin (Invitrogen) according to the instructions of the manufacturer. Positive viral clones were identified by their ability to direct the expression of the appropriate protein as revealed by immunoblotting of whole-cell extracts of transfected Sf9 cells harvested 3 d posttransfection using an antibody to the His tag of the protein. For apPKG proteinexpression, Sf9 cells were infected with the recombinant baculovirus at a multiplicity of infection of greater than 10. After 72 hr, cells were harvested and recombinant His-apPKG was purified on nickel nitriloacetic acid resin (Qiagen, Valencia, Calif.) according to the manufacturer's instructions. To express VASP (vasodilator-stimulated phosphoprotein), the coding region of VASP was first obtained by PCR amplification from mouse brain cDNA with the following primers: 5'-gtcgtgggatccccatcgatagcgagacggtcatctgt (SEQ ID NO:13) and 5'-atcttgaattcctcgagggtcaag-gagaaccccgctt (SEQ ID NO:14). The PCR product was subcloned into the EcoRI and BamHI sites of pGEX3X (Amersham Biosciences, Arlington Heights, Ill.) and was subsequently confirmed by sequencing. The resulting construct pGEXVASP contains a C-terminal GST (glutathione S-transferase) epitope tag. VASP-GST, Elk1-GST, MEKK1C (MAP kinase kinase kinase 1C)-GST, MEK1 (MAP kinase kinase 1)-GST, and ERK1-GST fusion proteins were expressed in *Escherichia coli* DH5α and purified as described (Sung et al., 1996).

Northern blots. Total RNA was extracted from various tissues and resolved by denaturing agarose gel electrophoresis; the gel was then transferred to a nylon membrane. The resulting blot was hybridized with radioactively labeled apPKG and 5S ribosomal cDNA as described previously (Alberini et al., 1994; Sung et al., 2001).

Single-cell RT-PCR. Single SNs were transferred to 500 µl of Tri Reagent (Molecular Research Center, Cincinnati, Ohio), and total RNA was isolated according to the manufacturer's instructions. cDNA from each sample was synthesized using random hexamers as primers and reverse transcriptase (SuperScript II). Aliquots (2 µl) from each sample were used to amplify specific fragments by PCR (40 cycles), using specific primer sets for the following: (1) neuronal nitric oxide synthase (NOS) (GenBank accession number AAK83069), 5'-gtaccctcacaggacgagtc (SEQ ID NO:15) and 5'-tccttggac-ctctcttggtg (SEQ ID NO:16) (nt 3610-4049); (2) SN-specific neuropeptide sensorin A (GenBank accession number X56770), 5'-aacagaaacagtctttcccc (SEQ ID NO:17) and 5'-tcttgactcaccaactgcc (SEQ ID NO:18) (nt 43-331); and (3) neuron-specific actin (GenBank accession number U01352), 5'-cagagagaagatgacccag (SEQ ID NO:19) and 5'-gggtaa-gagaagcaagaaag (SEQ ID NO:20) (nt416-1298).

Kinase assays. In vitro PKG activity was measured as described (Pohler et al., 1995). Briefly, 100 ng of His-apPKG was incubated with 5 µg of various peptides in a buffer containing the following (in mM): 25 Tris-HCl, pH 7.5, 5 β-glycerol phosphate, 2 DTT, 0.1 $Na_3VO_4$, and 10 $MgCl_2$. The reaction was initiated by adding 10 µM [γ-$^{32}$P]ATP. The incubation was allowed to proceed for 20 min at room temperature and terminated with 50 mM EDTA (final concentration). Labeled peptides were captured on P81 filters (Whatman, Maidstone, UK). The filters were washed with 0.5% phosphoric acid and dried, and the bound $^{32}$P-phosphopeptide was detected by liquid scintillation counting. All of the values were corrected for background counts per minute obtained without the substrate. To evaluate endogenous apPKG activity, 5 µg of ganglia extract or axoplasm was used in the kinase buffer (above) with 5 µg of PKA inhibitor and in the presence or absence of 1 µM cGMP. ERK activity was assayed as described (Sung et al., 2001). Briefly, proteins and 500 µM ATP were incubated in kinase buffer for 20 min at room temperature. The reaction mixtures were resolved on 10% SDS polyacrylamide gels and subjected to Western blotting with antibody (Ab)pTpYmapk, AbpYmapk, AbpTmapk, or AbpElk1.

In situ hybridization. Ganglia were first isolated from animals, desheathed, and fixed in 4% paraformaldehyde in PBS, pH 7.4, for 3 hr. The ganglia were then washed several times in 1×PBS and then digested with 80 µg/ml proteinase K (Ambion, Austin, Tex.) in 1 µPBS for 30 min at room temperature (RT). After several washes in 1×PBS, the ganglia were fixed again for 20 min with 4% paraformaldehyde and then washed several more times in 1×PBS. After treatment with 1.32% triethanolamine HCl, pH 8.0 (10 min at RT), and 0.24% acetic anhydride in 1.32% triethanolamine HCl, pH 8.0 (20 min at RT), and several washes with 1×PBS, the ganglia were prehybridized in Hyb buffer (50% formamide, 5×SSC, 5×Denhardt's solution, 0.25 mg/ml yeast tRNA, and 0.5 mg/ml salmon sperm DNA) at 60° C. for 2 hr, and then hybridized overnight at 60° C. with fresh Hyb buffer containing either antisense or sense digoxigenin (DIG)-labeled cRNA (1 µg/ml). After hybridization, ganglia were first washed for 30 min in fresh Hyb buffer at 68° C., and then in 0.2×SSC at 68° C. for 1 hr. After equilibration in PBST (1×PBS and 0.1% Triton X-100), ganglia were blocked with 10% sheep serum in PBST for 30 min at RT, and then incubated with anti-DIG antibody (1:5000) coupled to alkaline phosphatase (Roche, Indianapolis, Ind.) in 1×PBST containing 1% sheep serum overnight at 4° C. Hybridization signals were visualized with nitroblue tetrazolium chloride/5-bromo-4-chloro-3-indolyl phosphate (Roche).

Western blotting. Protein samples were resolved on 10% SDS polyacrylamide gels and subsequently transferred onto nitrocellulose membranes (Schleicher & Schuell, Keene, N.H.); the blots were probed with various gene-specific primary antibodies and appropriate horseradish peroxidase-conjugated secondary antibodies. Immunoreactivity was detected using the Pico-tag chemiluminescence system (Pierce, Rockford, Ill.).

Immunocytochemistry. Ganglia, nerve, or cultured cells were fixed with 4% paraformaldehyde in PBS, pH 7.4. The primary antibody was diluted in TBS supplemented with 0.1-0.5% Triton X-100 in TBS and 5% goat serum, and incubated overnight at 4° C. After several washes, an Alexa Fluor 594- or 488-conjugated secondary antibody (Molecular Probes, Eugene, Oreg.) was applied for 1 hr at room temperature. Subsequently, the cells were visualized by confocal fluorescence microscopy (LSM510 confocal microscope; Zeiss, Oberkochen, Germany), and images were collected.

Cell culture. SNs were isolated from the pleural ganglia of 50-80 gm animals and were plated on poly-L-lysine-coated dishes containing L15 medium and 50% hemolymph (Dagan and Levitan, 1981; Glanzman et al., 1989). Cultures were maintained at 18° C. for up to 7 d. Medium was changed every 2 d. Drugs were washed out 1 hr before electrophysiological tests.

Electrophysiology. Before the start of each recording, the hemolymph was replaced with a 1:1 mixture of artificial seawater and culture medium (without hemolymph; pH 7.6). Standard techniques were used for intracellular stimulation and recording (Ambron et al., 1996). The soma spike threshold was measured with a standard series of 20 msec depolarizing pulses. Repetitive firing was quantified by counting the number of spikes evoked by a series of 2 sec depolarizing pulses at 1, 2, 3, 4, and 5 nA, or 1 sec depolarizing pulses at 2.5 times the current for the 20 msec threshold. Spike amplitude was measured from baseline to the peak of the action potential, and spike duration was the breadth of the action potential at one-half of its maximal height.

Fluorescence protein labeling. BSA, apPKG, and ERK1 protein were labeled using an Alexa Fluor 546 Protein Labeling kit (Molecular Probes) according to the manufacturer's instructions.

SN microinjection. Microinjection pipettes were prepared with a Sutter programmable puller. Alexa Fluor 546-labeled protein (0.75 µg/µl in 10 mM Tris-HCl, pH 7.3, 100 mM NaCl, and 0.05% fast green dye) was microinjected into cultured SNs by applying positive air pressure under defined conditions (pounds per square inch and duration) using a picospritzer (Sung et al., 2000).

Materials. Recombinant bovine PKG 1α, guanosine 3',5'-cyclic monophosphorothioate, 8-(4-chlorophenylthio)-, Rp isomer (Rp-8-pCPT-cGMPS), adenosine 3',5'-cyclic monophosphorothioate, Rp isomer (Rp-cAMPS), 1-H[1,2,4]oxa-diazolo[4,3-a]quinoxalin-1-one (ODQ), L-thiocitrulline, $N^G$-nitro-L-arginine methyl ester hydochloride (L-NAME), protein kinase A inhibitor 6-22 amide, and PKG substrate BPDEtide were purchased from Calbiochem (La Jolla, Calif.). Peptides A, C, and D, and MAPK p42 protein were obtained from Santa Cruz Biotechnology (Santa Cruz, Calif.). The following antibodies were obtained and used according to the manufacturer's instructions: anti-phospho-VASP (Ser239) from UpstateCell Signaling Solutions (Lake Placid, N.Y.), polyclonal antibodies to phosphorylated MAPK ($Ab^{pTpYmapk}$) and phospho-Elk1 ($Ser^{383}$; $Ab^{pElk1}$) from Cell Signaling Technology (Beverly, Mass.), and anti-pY MAPK ($Ab^{pYmapk}$), anti-pT MAPK ($Ab^{pTmapk}$), and α-actin from Sigma (St. Louis, Mo.).

6.2 Results

*Aplysia* SNs Contain a Neuronal Type-I PKG.

Figure 1B:
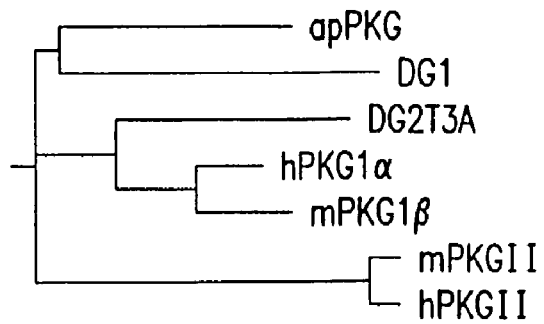

To investigate the role of the PKG pathway in the induction of LTH, an *Aplysia* PKG was cloned (GenBank accession number AY362340). ApPKG cDNA contains an open reading frame encoding a putative 733 aa protein. In concordance with all of the known PKGs, the *Aplysia* kinase contains two tandem cyclic nucleotide-binding domains and a C-terminal catalytic domain (FIG. 1A, top). The predicted protein encoded by the apPKG sequence is highly similar to known cGMP-dependent protein kinases with greater than 50% amino acid identity to *Drosophila* PKGs and to the mammalian type-I and -II PKG isoforms (FIG. 1A, bottom). However, it appears to be most closely related to *Drosophila* DG1 (FIG. 1B).

Figure 1C:
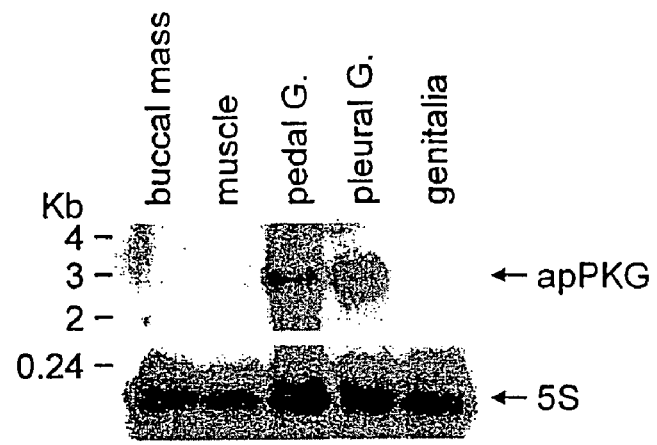

To determine the pattern of apPKG expression, a Northern blot of total RNA from various tissues from the adult animals was probed with a $^{32}$P-labeled 283 bp fragment corresponding to bases 209-492 of the cDNA. The probe detected a single 3.0 kb transcript that was expressed in ganglia, but not in muscle or the genital organs (FIG. 1C). A $^{32}$P-labeled probe to 5S ribosomal RNA detected a 0.19 kb transcript in all of the tissues (FIG. 1C).

Figure 1D:
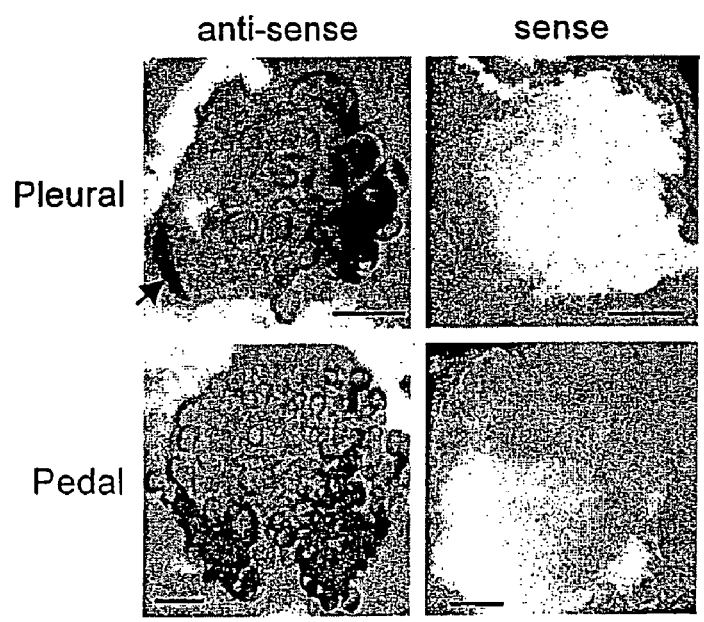

To localize the source of the message, the apPKG probe was used to generate sense and antisense riboprobes for in situ hybridization. The antisense probe detected high levels of apPKG mRNA expression in the SN cluster and in most of the neurons in the pedal and pleural ganglia (FIG. 1D, left panel). Negligible labeling resulted from the sense probe (FIG. 1D, right panel).

The catalytic properties of apPKG were then investigated by first expressing apPKG cDNA in a baculovirus/Sf9 system. An inactive His-tagged recombinant apPKG was produced when the cells were grown in the presence of serum, and a constitutively active apPKG was made when the cells were deprived of serum. Both recombinant apPKG forms were purified via affinity chromatography.

Inactive apPKG was activated by 100 nM 8-Br-cGMP and readily phosphorylated BPDEtide, a peptide substrate for all of the type-I PKGs (Glass and Krebs, 1982) (FIG. 2A). Comparison of active apPKG with recombinant bovine type-Iα soluble PKG showed that both kinases readily phosphorylated several PKG peptide substrates (FIG. 2B). Significantly, neither kinase phosphorylated peptide C, which is the preferred substrate for membrane-bound type-II PKG (Hall et al., 1999) (FIG. 2B). The protein VASP, whose serine at position 239 is recognized specifically by type-I soluble PKGs (Smolenski et al., 1998), was also examined, and it was found that both the bovine and *Aplysia* kinases phosphorylated this site (FIG. 2C). These studies establish apPKG as a member of the soluble type-I family of PKGs.

ApPKG is Located in Axons where it is Activated by Nerve Injury and Retrogradely Transported to the Cell Body of the SNs.

*Aplysia* peripheral nerves p5-p9 innervate the mid-body wall and tail region and contain axons of the SNs (Walters et al., 1983a,b; Billy and Walters, 1989). To determine whether apPKG is in axons, a rabbit polyclonal antibody, $Ab^{apPKG}$, was raised against a peptide located at the N terminus (amino acids 18-128) of the protein. $Ab^{apPKG}$ was affinity purified and used to probe Western blots. $Ab^{apPKG}$ recognized 80 and 100 kDa polypeptides in pedal and pleural ganglion extracts, but not in muscle or genital tissue as well as the affinity-purified 80 kDa recombinant protein (FIG. 3A). It is believed that the 100 kDa band is the dominant form of apPKG, because it is most abundant and has a greater affinity for cGMP than the 80 kDa constituent. Both bands were also recognized by a commercial antibody that was generated against human type-IαPKG (amino acid residues 657-671: 50% identity to apPKG). apPKG contains consensus sequences for several kinases and other enzymes and the 100 kDa constituent might contain one or more posttranslational modifications.

To determine whether apPKG is present in axons, axoplasm was extruded from nerves p5-p9. FIG. 3A shows that both polypeptides were present. The SNs have axons in nerves p5-p9, and immunocytochemistry with AbapPKG stained essentially all of the SNs in the cluster (FIG. 3B). To determine the effects of nerve injury on axonal apPKG, nerves p5-p9 on one side were crushed, thereby axotomizing the axons in each nerve. At various times afterward, apPKG activity was assayed in the ipsilateral and contralateral pedal and pleural ganglia, which included the cluster of SN cell bodies. As shown in FIG. 4A, there was a delay of about 16 hr after nerve crush before significant apPKG activity appeared in the ipsilateral pleural ganglion. The activity then increased for at least 24 hr, but was not significantly different from baseline at 48 hr. Little or no apPKG activity was detected in the contralateral control pleural ganglion (FIG. 4A). Significantly, apPKG activity in the cell bodies of the ipsilateral pedal ganglion neurons remained at basal level during the 48 hr after axotomy (FIG. 4A), indicating that the activation of apPKG is selective for neurons in the pleural ganglion.

The long delay before apPKG activity appeared in the cell bodies is consistent with the idea that the kinase is a positive injury signal. Moreover, apPKG contains a nuclear localization sequence (NLS) that can provide access to the retrograde transport system (Ambron and Walters, 1996; Schmied and Ambron, 1997; Hanz et al., 2003). A standard crush-ligation protocol was used to investigate this possibility (Ambron et al., 1995; Johanson et al., 1995) (FIG. 4B). Nerves p5-p9 were crushed unilaterally, and a ligation was placed on each nerve proximal to the crush site. Proteins that are transported away from the crush site (toward the cell bodies) accumulate in the axoplasm behind the ligation where they can be collected. 24 hr later 0.5 cm nerve segments were removed as follows: (1) proximal to the crush (Cr) site, (2) distal to the ligation on the crushed nerves (the Cr/Lig site), and (3) distal to the ligation on the control side (the Lig site) (FIG. 4B, top). Axoplasm was then extruded from each segment, as well as from segments of nerves p5-p9 from an animal that did not receive a nerve injury. When equal amounts of each axoplasm were screened for apPKG activity, there was a 10-fold increase in apPKG activity in axoplasm from the Cr/Lig segment relative to basal activity in axoplasm from noninjured animals (FIG. 4B, bottom). In contrast, apPKG activity at the Cr segment was only threefold greater than the basal activity, and that at the Lig segment was at the basal level.

The accumulation of apPKG activity at the Cr/Lig site was supported by immunocytochemical studies in which $Ab^{apPKG}$ was used to examine the distribution of ap-PKG protein in noninjured and injured nerves. apPKG staining was uniformly distributed along axons in naive nerves (FIG. 4C, panel 1). After nerve crush, however, there was a decrease in the staining at the Cr site (FIG. 4C, panel 3) and a significant increase at the terminations of axons at the Cr/Lig site (panel 4). There was no increase in staining at the Lig site (FIG. 4C, panel 2). The accumulation of both apPKG protein and activity at the Cr/Lig site relative to the Cr and Lig sites is strong evidence that apPKG is a positive injury signal (Ambron et al., 1995).

The Nitric Oxide-cGMP-PKG Pathway Regulates the Induction of LTH in SNs In Vitro.

When *Aplysia* SNs are axotomized by removal from the ganglion and individually placed in culture, they regenerate their axons and exhibit a decrease in spike threshold and an increase in repetitive firing, which are two characteristics of LTH (Ambron et al., 1996; Bedi et al., 1998; Sung and Ambron, 2004). To examine the appearance of this LTH in greater detail, the electrical properties from the SNs in vitro were recorded on the second to the seventh day and compared to the electrical recordings from SNs within the cluster in situ. Approximately 10% of the cells tested in vitro did not have a sufficient resting potential or were refractory to firing and were not included in the study. The same decrease was detected in threshold and increase in repetitive firing as reported previously, and it was also found that the axotomized SNs exhibited significant spike broadening and an increase in spike amplitude relative to the controls (FIG. 5). The changes were significant on the second day and persisted until at least the seventh day. The fact that these same four changes in electrical properties occur in hyperexcitable rat DRG SNs after axotomy (Abdulla and Smith, 2001), affirms the use of dissociated *Aplysia* SNs as a model system for studies of sensory alterations that may contribute to neuropathic pain.

To investigate whether the appearance of the LTH requires apPKG activity, the SNs were removed from the ganglion in the presence of either the soluble guanylyl cyclase (sGC) inhibitor ODQ, the PKG inhibitor Rp-8-pCPT-cGMPS, or the PKA inhibitor Rp-cAMPS. The latter was used because PKA has properties in common with PKG (Scott, 1991; Francis and Corbin, 1994) and has been implicated in various forms of synaptic plasticity in *Aplysia* SNs (Ghirardi et al., 1992; Byrne and Kandel, 1996; Bedi et al., 1998; Muller and Carew, 1998; Chain et al., 1999; Liao et al., 1999; Sutton and Carew, 2000; Antonov et al., 2003). The cells were subsequently allowed to regenerate in the presence of the inhibitors in vitro, and on the third day, their electrophysiological properties were compared with those of SNs that were removed from the same ganglia at the same time, but that had not been exposed to a drug. It was found that both Rp-8-pCPT-cGMPS and ODQ prevented the increase in repetitive firing (FIG. 6A) and the decrease in spike threshold (B). In contrast, the PKA inhibitor had no significant effect on either parameter. Neither Rp-8-pCPT-cGMPS nor ODQ inhibited the appearance of excitability when added to 2-d-cultured SN, confirming the data in FIG. 4A showing that apPKG activation is transient. Neither spike broadening nor amplitude were evaluated in these experiments.

None of these treatments, which used similar or even lower concentrations of the drugs than that reported for mammalian (Monfort et al., 2002) and *Aplysia* neurons (Lewin and Walters, 1999), affected the resting membrane potential. Significantly, they also did not alter the extent or pattern of neurite growth. In contrast, exposing SNs to U0126, a selective MEK inhibitor, produced severe growth defects.

Figure 6A:
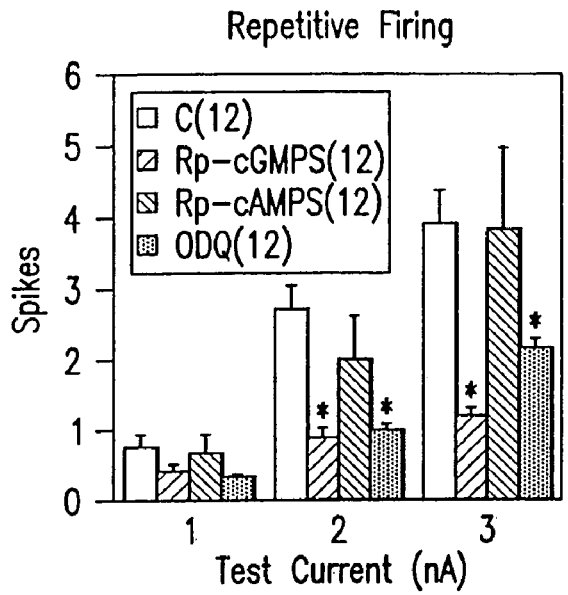
Figure 6B:
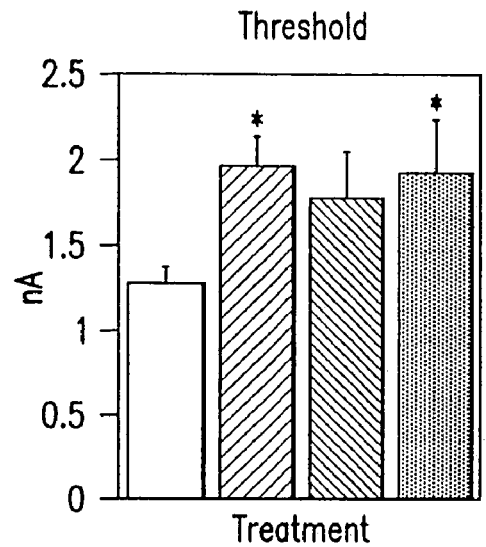
Figure 6C:
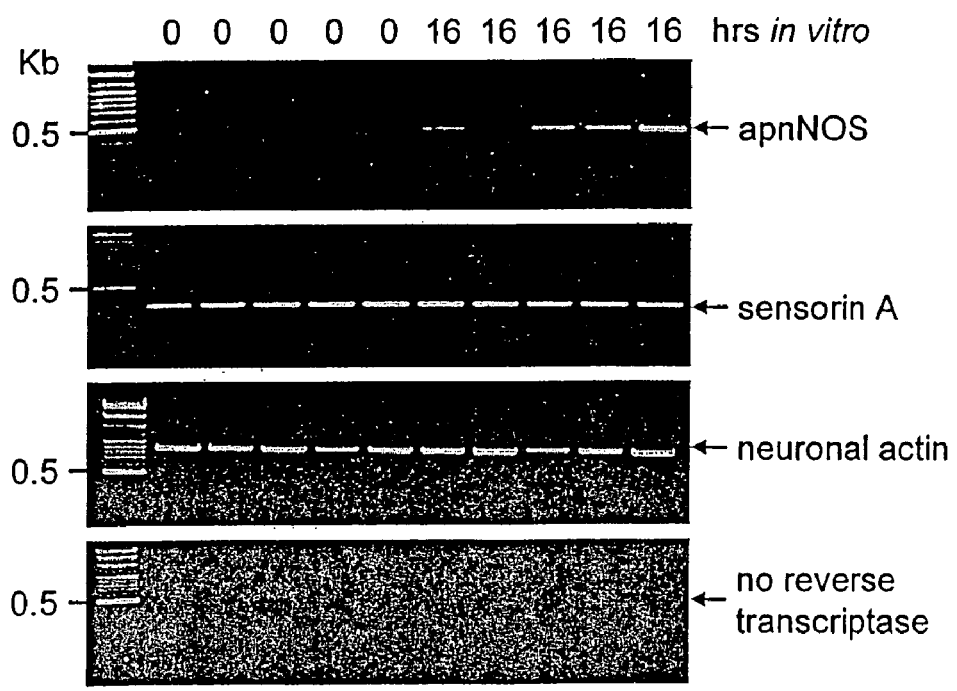

The inhibition of LTH by the sGC and PKG inhibitors indicated that cGMP synthesis and PKG activation occur within the sensory neurons. NO is known to elevate cGMP production via sGC (Schlossmann et al., 2003), and NO is produced by the enzyme NOS (Bredt and Snyder, 1990; Moroz et al., 1996). To investigate the likelihood that NOS activation is required for LTH, RT-PCR was used to detect the cellular levels of apn-NOS mRNA in single SNs immediately after their removal from the ganglion (0 hr) or after 16 hr in vitro. As shown in FIG. 6C (top panel), four of five cells expressed significant amounts of apnNOS mRNA after 16 hr in vitro, whereas none was detected in the 0 hr cells. In contrast, the mRNA for the SN-specific neuropeptide sensorin A (Brunet et al., 1991) and the neuronspecific isoform of actin (DesGroseillers et al., 1994) was abundant in every cell (FIG. 6C, second and third panels, respectively).

Figure 6D:
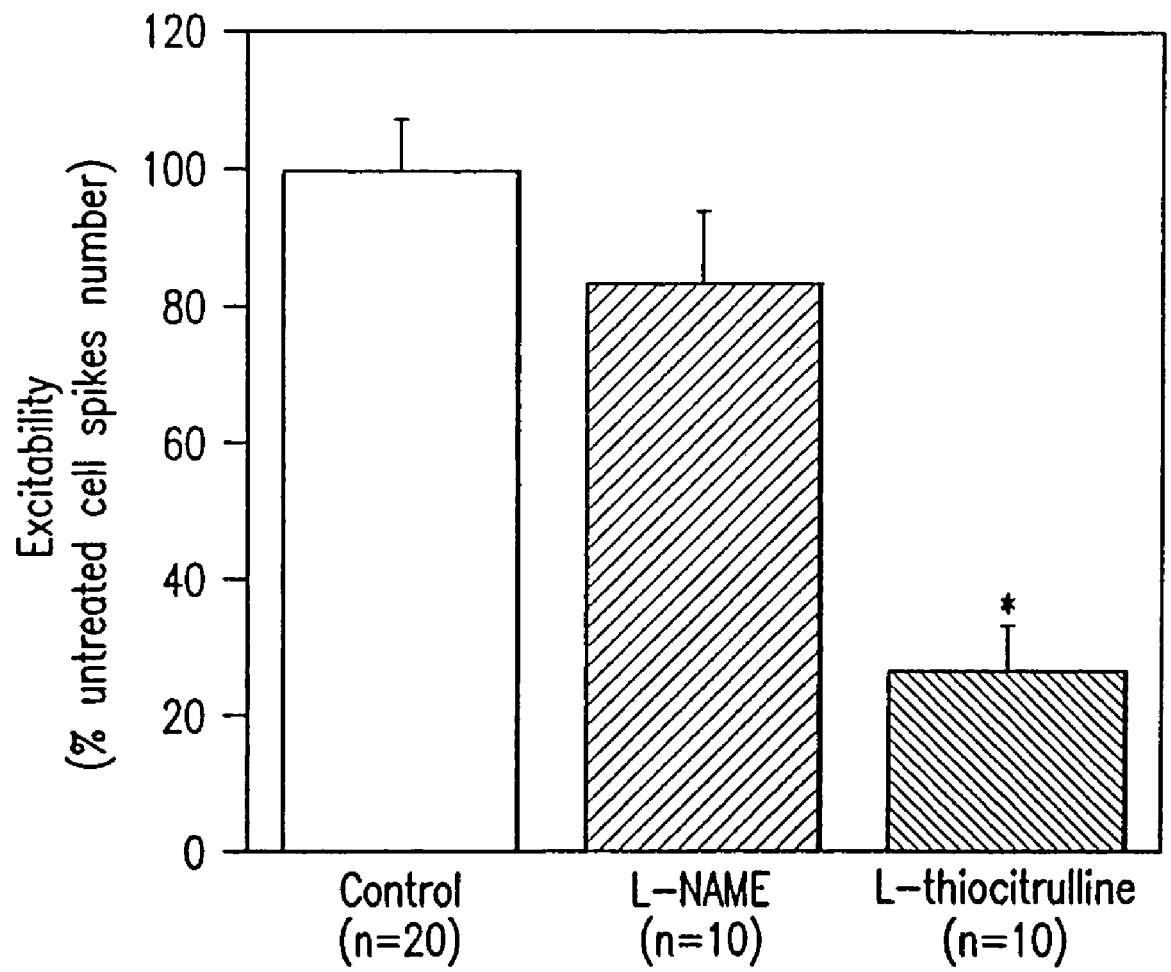

L-Thiocitrulline is an effective inhibitor of apNOS, and it was found that exposing the SNs to this drug in vitro as above markedly reduced the maximum firing relative to untreated controls (FIG. 6D). Another NOS inhibitor, L-NAME also reduced LTH under the same conditions, but was not as effective as L-thiocitrulline (FIG. 6D). These data indicate that the NO-cGMP-PKG pathway is required for inducing LTH in the SNs.

Somatic apMAPK is Phosphorylated at its Activation Site by apPKG.

Figure 7A:
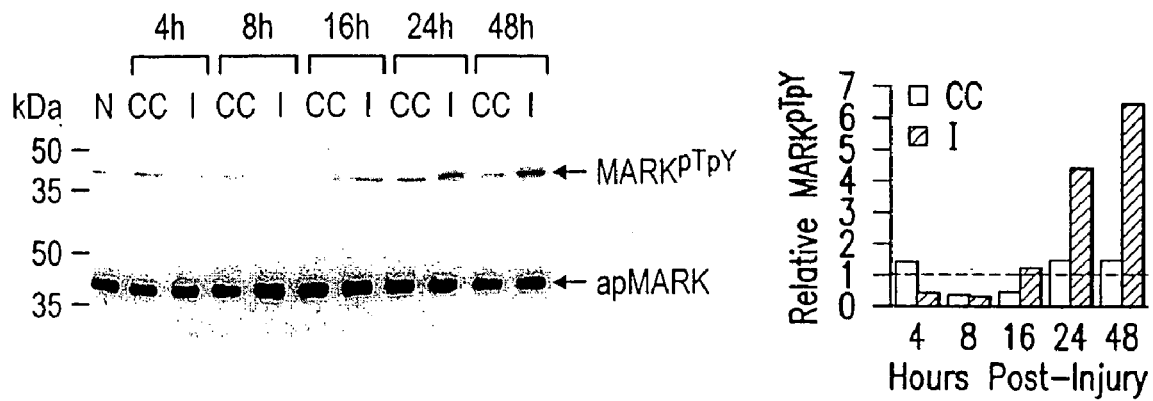

The induction of LTH in *Aplysia* SNs after peripheral injury requires gene transcription (Lewin and Walters, 1999) and could be effected directly by apPKG if the kinase translocated to the nucleus after entering the cell body. Immunostaining revealed a low constitutive level of apPKG in some SN nuclei, but there was no increase after axotomy (FIG. 3B). This suggested that apPKG contributes to the induction of LTH by activating a factor that is imported into the nucleus. An ERK member of the MAPK family is a good candidate for this factor, because LTH can be induced by injecting recombinant ERK1 into SN somata (Sung et al., 2001). To assess whether an ERK was activated after injury, p5-p9 were crushed in vivo and used to produce Western blots of injured and control pleural neurons, which were probed with an antibody ($Ab^{pTpYmapk}$) that recognizes ERKs that have been activated by dual phosphorylation at the T-E-Y site. The antibody recognized a single 43 kDa polypeptide that had little activity in pleural neurons 4 or 8 hr after the injury (FIG. 7A, top panel). By 16 hr, however, there was more active kinase on the crush side relative to the contralateral control, and the level continued to increase for at least 48 hr (FIG. 7A, top panel).

Figure 7B:
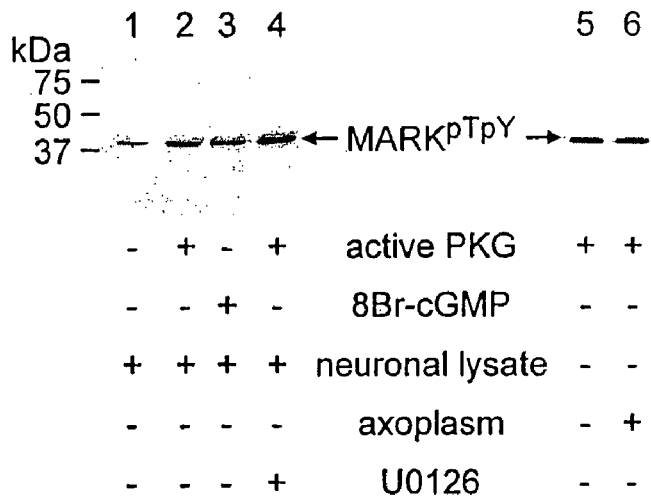
Figure 7C:
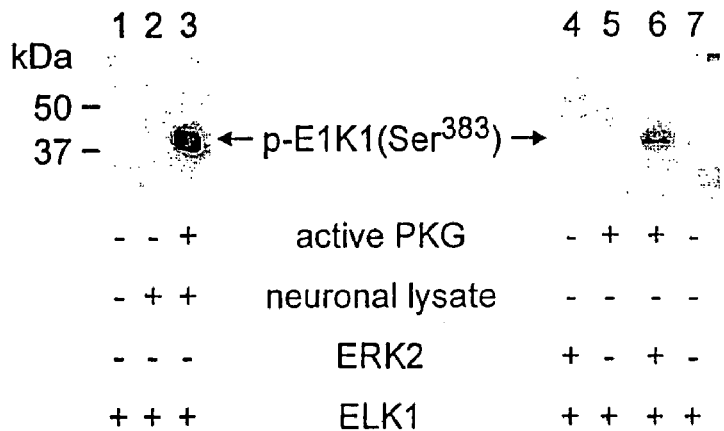

*Aplysia* neurons contain an ERK2 homolog, apMAPK (Michael et al., 1998), that enters the nucleus after injury in vitro (Martin et al., 1997). apMAPK has the same catalytic domain and T-E-Y activation site as ERKs 1 and 2. To determine whether apMAPK was the kinase activated after injury, we probed the same blot with an antibody, D8, which specifically recognizes apMAPK (Martin et al., 1997), and found that the antibody recognized the 43 kDa injury-activated kinase (FIG. 7A, bottom panel). The antibody detects both active and inactive apMAPK, and there was little difference in the amount of total apMAPK protein among the samples. The finding that apMAPK activity began to increase just after the arrival of active apPKG in the cell body (compare FIGS. 4A, 7A) suggested a link between apPKG and apMAPK. This idea was tested by preparing a lysate of pleural ganglion neurons and using $Ab^{pTpYmapk}$ to monitor samples for active apMAPK. Little endogenous phospho-apMAPK was detected in the lysate (FIG. 7B, lane 1), but adding active apPKG or 8-Br-cGMP markedly enhanced the level of active ap-MAPK (lanes 2, 3) that was recognized by antibody D8. Surprisingly, the activation was not blocked by U0126, a potent inhibitor of the upstream kinase MEK (FIG. 7B, lane 4). Interestingly, adding active apPKG to axoplasm did not activate apMAPK (FIG. 7B, lanes 5, 6) (see Discussion). Another study with the lysate showed that the apPKG-activated ap-MAPK phosphorylated its physiological substrate, Elk1, at the appropriate Ser$^{383}$ (FIG. 7C, lane 3).

Figure 7D:
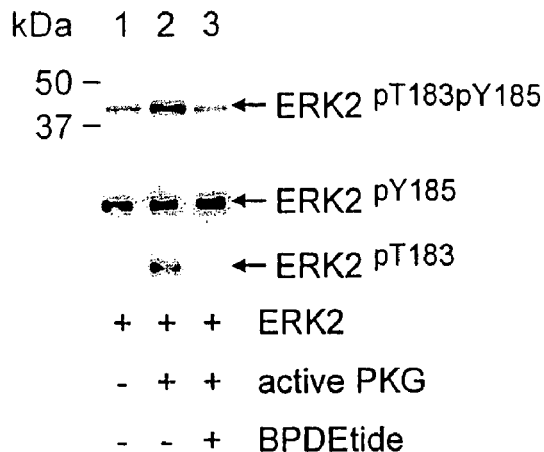

The activation of apMAPK in the presence of U0126 suggested that apPKG activates apMAPK directly, and therefore active apPKG was incubated with recombinant mammalian ERK2. ERK2 was a surrogate for apMAPK. Both kinases contain the target T-E-Y site, however. As in the lysate, apPKG activated ERK2 to phosphorylate Elk1 (FIG. 7C, lane 6). When the experiment was repeated, the activated ERK2 was recognized by $Ab^{pTpYMAPK}$, indicating that it was doubly phosphorylated (FIG. 7D, top, lane 2). The activation was specific, because it was reduced in the presence of BPDEtide (FIG. 7D, top, lane 3). ERK2 is maximally activated when both the -T- and -Y- amino acids are phosphorylated, yet PKGs are serine/threonine kinases. It is relevant, therefore, that bacterial recombinant ERK2 has a low level of activity that is attributable to the presence of a phosphate on the -Y- moiety (Cha and Shapiro, 2001). Indeed, the antibody to ERKpY185 recognized the recombinant ERK2 substrate on a Western blot (FIG. 7D, middle). There was no increase in phosphorylation of the -Y- when ERK2 was incubated with apPKG (FIG. 7D, middle, lane 2). However, when a duplicate blot was probed with an antibody to ERKpT183, there was an increase in the phosphorylation of the -T- in the presence of apPKG (FIG. 7D, bottom, lane 2). This antibody reacts specifically with the monophosphorylated threonine and doubly phosphorylated ERKs. This result indicates that ap-PKG can fully activate ERK2 by phosphorylating ERK2 that already contains a phosphate on the Y-185.

Figure 7E:
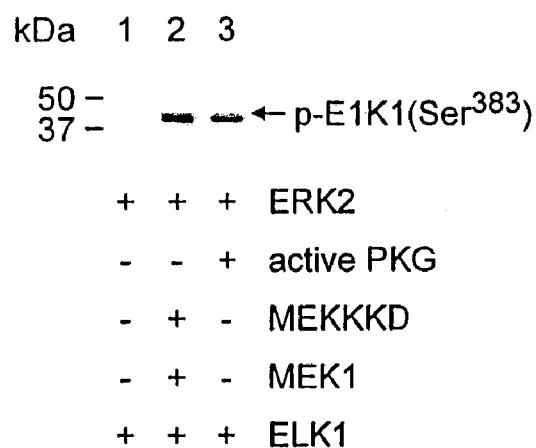

It was next examined whether incubating apPKG and recombinant ERK2 produces an active ERK2 with enzymatic activity comparable with that produced by MEK1, which produces the maximally activated kinase. ERK2 activity was measured by the phosphorylation of Elk1 at Ser$^{383}$, and MEK1 was activated by the catalytic subunit of MEKK1 (Xu et al., 1995). As anticipated, apPKG produced an ERK2 with similar activity as that produced by MEK1 (FIG. 7E). This result indicates that, in addition to MEK1, PKG is an activator of ERK2.

Figure 7F:
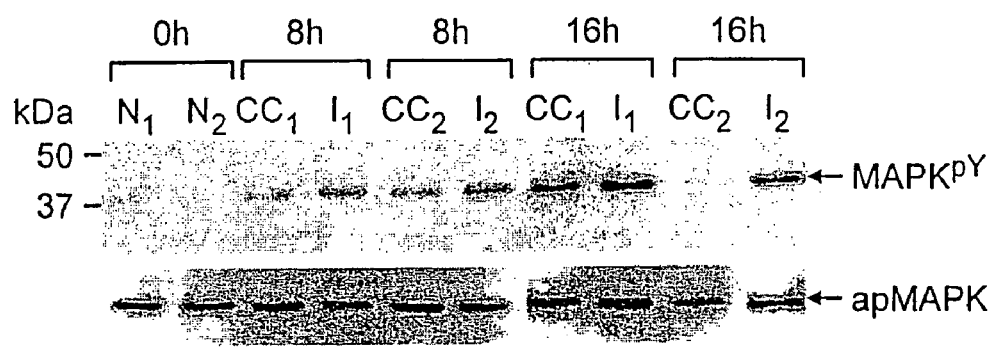

Because PKG phosphorylates T183 on ERK2 that already has a phosphate on Y185 (FIG. 7D), an essential question is whether monophosphorylated apMAPK at -Y- is available for phosphorylation by apPKG after axotomy. This question was answered by first crushing p5-p9 in vivo. Samples were then blotted and probed with an antibody to ERKpY185. Indeed, apMAPKpY was present in pleural neurons 8 hr after the injury, and its expression was increased on the crush side relative to the contralateral control at 16 hr (FIG. 7F, top panel). ApMAPKpY was not detected in two naive animals that were analyzed (FIG. 7F, top panel). Probing the blot with an antibody that detects both active and inactive apMAPK showed that there was little difference in the amount of total apMAPK protein among the samples (FIG. 7F, bottom panel). Thus, the presence of apMAPKpY in the soma 16 hr after the injury, in conjunction with the arrival of apPKG from the crush site (FIG. 4A), should result in full activation of apMAPK.

The Level of apMAPK in the Nucleus of SNs In Vitro is Reduced when apPKG Activity is Inhibited.

The evidence above indicates that apPKG does not enter the nucleus of the SNs in response to nerve crush in vivo (FIG. 3B). Nevertheless, type-I PKGs have a putative NLS (Gudi et al., 1997), and apPKG has a short stretch of positively charged amino acids (453KCLKKKHI) in the ATP-binding domain that could function as an NLS. The import of proteins into the nucleus of Aplysia neurons is readily assessed by injecting their fluorescently labeled cognates directly into the cell body (Ambron et al., 1992; Schmied et al., 1993; Gunstream et al., 1995). Therefore Alexa labeled recombinant apPKG was injected into the soma of SNs after 2 d in vitro, the neurites were severed to initiate an injury response, and, 30 min later, the cells were examined by fluorescence microscopy. All of the labeled protein remained in the cytoplasm (FIG. 8A). Alexa labeled BSA also remained in the cytoplasm after injection, as expected (Ambron et al., 1992; Schmied et al., 1993; Gunstream et al., 1995). In contrast, injected Alexa-labeled active recombinant vertebrate ERK1, which is imported into the nucleus in a variety of cell types (Karin, 1994) rapidly entered the nucleus where it was distributed in discrete patches (FIG. 8A). Similar patches have been seen after the import of other proteins into Aplysia nuclei (Ambron et al., 1992; Schmied et al., 1993; Gunstream et al., 1995).

The inability of apPKG to enter the nucleus of Aplysia SNs is consistent with the idea that it contributes to the induction of LTH by promoting the nuclear import of apMAPK. If so, then inhibiting the apPKG pathway should block the axotomy-induced entry of apMAPK into the nucleus. Therefore, SNs were exposed in vitro either to the PKG blocker, Rp-8-pCPTcGMPS, or the PKA blocker, Rp-cAMPS, under the conditions that induce LTH (FIG. 6A). On the third day, the cells were fixed, permeabilized, and exposed to antibody D8 to visualize ap-MAPK. Confocal microscopy showed that untreated cells and those exposed to Rp-cAMPS had the same levels of nuclear staining (FIG. 8B). In contrast, there was a dramatic reduction in nuclear staining in the cells treated with Rp-8-pCPT-cGMPS (FIG. 8B). Thus, both the induction of LTH and the presence of ap-MAPK in the nucleus depend on apPKG activity.

6.3 Discussion

Persistent neuropathic pain in humans after nerve injury is physically and psychologically debilitating. Because an important component of this pain is often the LTH that appears in primary afferent neurons, it is important to understand how axotomy induces LTH. An LTH with similar properties appears in nociceptive SNs of Aplysia after axotomy, and the experimental advantages of these neurons were exploited to define a signaling pathway responsible for the induction of LTH. One major surprise was that this pathway involves the phosphorylation of apMAPK by PKG. This is an alternative to the traditional MAP kinase cascade and suggests that PKG and MAPK have unique roles after nerve injury.

ApPKG is a Positive Injury Signal in SNs.

An Aplysia type-I PKG was cloned whose mRNA is in the SNs and other neurons in the pleural ganglion (FIG. 1D). When the peripheral nerves were crushed in vivo, apPKG activity appeared in the somata of pleural neurons, but only after a delay of about 16 hr (FIG. 4A). A similar delay in response to nerve injury has been attributed to positive injury signals (Schmied et al., 1993; Sung et al., 2001; Lin et al., 2003). Western blots probed with $Ab^{apPKG}$ showed that apPKG is present in axoplasm extruded from the peripheral nerves (FIG. 3A). In addition, because proteins are retrogradely transported along *Aplysia* axons at a rate of 1.5 mm/hr (Ambron et al., 1992; Schmied et al., 1993; Gunstream et al., 1995), the delay is consistent with the transport of apPKG from the crush site, which was located 2 cm from the ganglion. When a ligation was placed proximal to the crush site it was found that activated apPKG and total apPKG protein accumulated on the distal side of the ligation, relative to the crush site (FIG. 4B,C). These findings establish apPKG as a positive injury signal.

The mechanism responsible for the injury-induced transport is not known. Although apPKG contains several potential myristoylation sites that could bind it to vesicles after injury, apPKG was found to be soluble after subcellular fractionation. Hanz et al. (2003) have shown that proteins containing an NLS are retrogradely transported via dynein and importins in the rat sciatic nerve, and apPKG may be transported using a similar mechanism.

The Appearance of the LTH in Axotomized *Aplysia* SNs In Vitro Depends on NOS, sGC, apPKG, and apMAPK.

The LTH that appears in both the SNs (FIG. 5) and mammalian nociceptive SNs after nerve injury (Abdulla and Smith, 2001) have similar electrophysiological properties. If this congruence reflects conserved mechanisms, then LTH might be induced by common pathways in both types of cells. SNs were examined in vitro and it was found that the axotomy-induced reduction in spike threshold and the increase in hyperexcitability were blocked by Rp-8-pCPT-cGMPS, ODQ, and L-thiocitrulline, inhibitors of apPKG, sGC, and NOS, respectively (FIG. 6A,B,D). Moreover, Rp-8-pCPT-cGMPS also caused a nearly threefold reduction in the level of apMAPK in the nucleus of the SNs (FIG. 8B). These findings pointed to a direct relationship between the activation of NOS and apPKG, the entry of apMAPK into the nucleus, and the induction of LTH. The finding that NOS mRNA expression in the SNs was increased after injury (FIG. 6C) implies that the level of NOS protein might be the rate-limiting step in the pathway. Neuronal NOS (nNOS) mRNA and protein expression also increase in DRG neurons after severing their peripheral axons (Verge et al., 1992; Fiallos-Estrada et al., 1993; Zhang et al., 1993).

cAMP and PKA have also been implicated in the induction and maintenance of LTH (Scholz and Byrne, 1988; Goldsmith and Abrams, 1992; Bedi et al., 1998), and this was a concern here because PKA and PKG have properties in common. However, it was found that exposing the SNs to Rp-cAMPS, a membrane-permeable inhibitor of PKA, neither prevented the induction of LTH nor blocked apMAPK entry into the nucleus. This confirms previous findings that PKA inhibitors failed to block LTH induced by noxious stimulation (Lewin and Walters, 1999).

The activation of both apPKG and ap-MAPK by injury was intriguing, because it suggested a possible link between these two kinases (Zaragoza et al., 2002). Indeed, when active apPKG was added to a neuronal lysate, it not only activated ap-MAPK (FIG. 7B), but did so via a pathway that did not require MEK, the ubiquitous upstream activator of the ERKs. This response was physiologically relevant, because activated apMAPK phosphorylated its nuclear substrate Elk1 at the Ser383 (FIG. 7C), which is essential for transcriptional activity (Marais et al., 1993; Whitmarsh et al., 1995). A direct interaction was established between the kinases when active apPKG was incubated with recombinant vertebrate ERK2, which has the same T-E-Y activation site as apMAPK. It was found that the ERK2 was both activated (FIG. 7C) and doubly phosphorylated (D, top). The latter finding indicated that the ERK2 was fully active, and this was supported by another study in which equal amounts of ap-PKG or MEK1 activated ERK2 to comparable levels (FIG. 7E).

The indications that apPKG produces a maximally activated ERK2 creates a paradox, because PKGs are serine-threonine kinases that cannot phosphorylate the tyrosine. However, because the recombinant ERK2 already contains phospho-tyrosine-185 (FIG. 7D, middle), the phosphorylation of threonine-183 by apPKG (FIG. 7D, bottom) should produce a fully activated ERK2. The phosphorylation of apMAPKpY by apPKG is attractive, because ERK2pY185 has been detected in vertebrate cells (Yao et al., 2000; Cha and Shapiro, 2001; Zhou and Zhang, 2002), and the evidence indicates that apMAPKpY expression increases in *Aplysia* neurons after nerve injury (FIG. 7F). apMAPKpY could be produced by a phosphatase that removes the phosphate from doubly phosphorylated apMAPK, or by an injury-activated tyrosine kinase that phosphorylates the tyrosine at the T-E-Y site. The possibility that the induction of LTH requires the convergence of apPKG and a tyrosine kinase on apMAPK would confer more control over this pathway. This is reasonable given that LTH radically alters the function of the injured neurons and leads to significant changes in the behavior of the animal.

apMAPK is also present in axoplasm, but is not activated by nerve injury (Sung et al., 2001; Lin et al., 2003), which is paradoxical, given that injury activates the axoplasmic apPKG. One explanation would be that the two kinases are located in different axons. However, when active apPKG was added to axoplasm extruded from the peripheral nerves, apMAPK was not activated under the same conditions that caused its activation in the cell soma (FIG. 7B). Evidently, there is a mechanism in the axon that shields apMAPK from apPKG. Nevertheless, these observations mean that, after its activation in the axon by injury, apPKG must be transported back to the soma to influence nuclear events via apMAPK.

With regard to the molecular pathway described herein, the possibility remains that nerve injury may cause translocation of apMAPK or activation of somatic PKG by other pathways as well. An NO-cGMP-PKG-MAPK signaling pathway might also be important for LTH induced by the inflammation that develops around a nerve injury site, both in mammals (Millan, 1999; Zimmermann, 2001) and in *Aplysia* (Clatworthy et al., 1995; Clatworthy and Grose, 1999; Farr et al., 1999, 2001). How might nuclear apMAPK regulate LTH? apMAPK can phosphorylate CREB2 (cAMP response element-binding protein 2), a cAMP response element (CRE) site repressor (Bartsch et al., 1995; Michael et al., 1998), C/EBP (CCAAT/enhancer-binding protein), a transcription factor that binds to the estrogen response element (ERE) site (Alberini et al., 1994), and Elk1, a transcription factor that regulates the serum response element (SRE) site (Lin et al., 2003). Binding to all three sites increases after nerve injury, but with different time courses. Thus, binding of C/EBP and CREB to the ERE and CRE, respectively, is rapid, but relatively short lived (Dash et al., 1998; Sung et al., 2001), whereas the binding of Elk1 to the SRE is biphasic, with an early phase that lasts for a few hours and a second phase that persists for weeks (Lin et al., 2003). CREB is phosphorylated in DRG neurons in response to intense activity (Ji and Woolf, 2001), and the CRE site is required for the LTH response to noxious stimuli in *Aplysia* SNs (Lewin and Walters, 1999). These considerations point to CREB2 and C/EBP as targets of apMAPK during the initial induction of the LTH in the SNs. The persistence of LTH for weeks may be mediated by the phosphorylation of Elk1 by apMAPK. This pathway is selective, because inhibiting NOS, sGC, or PKG prevented the appearance of LTH in dissociated SNs, but did not block growth. If the link between this pathway and LTH represents a fundamental, widely conserved relationship, then therapeutic interventions that target this pathway may be used to mitigate persistent pain after nerve injury without blocking axon regeneration.

7. EXAMPLE

Blocking of PKG Activity in Rat

FIG. 9 shows that the activation of PKG can be blocked at the site of injury using an inhibitor of PKG, Rp-8-pCPT-cGMPS ("RP-G"). The experiment was carried out as follows. A rat was anesthetized using a standard protocol and the sciatic nerve was exposed and injured in either the absence or the presence of RP-G, or an inhibitor of PKA, Rp-8-pCPT-cAMPS, ("RP-A"). Four hours later, the nerve was sectioned as shown in the schematic above the graph in FIG. 9, and each segment was assayed for PKG activity. In the absence of inhibitor (black bars), active PKG had been transported toward the cell bodies and was enriched in P3. RP-A (gray bars) did not change this pattern. In contrast, RP-G (white bars) abolished the activity.

8. REFERENCES

Abdulla F A, Smith P A (2001) Axotomy- and autotomy-induced changes in the excitability of rat dorsal root ganglion neurons. J Neurophysiol 85:630-643.

Alberini C M, Ghirardi M, Metz R, Kandel E R (1994) C/EBP is an immediate-early gene required for the consolidation of long-term facilitation in *Aplysia*. Cell 76:1099-1114.

Ambron R T, Walters E T (1996) Priming events and retrograde injury signals. A new perspective on the cellular and molecular biology of nerve regeneration. Mol Neurobiol 13:61-79.

Ambron R T, Schmied R, Huang C C, Smedman M (1992) A signal sequence mediates the retrograde transport of proteins from the axon periphery to the cell body and then into the nucleus. J Neurosci 12:2813-2818.

Ambron R T, Dulin M F, Zhang X P, Schmied R, Walters E T (1995) Axoplasm enriched in a protein mobilized by nerve injury induces memorylike alterations in *Aplysia* neurons. J Neurosci 15:3440-3446.

Ambron R T, Zhang X P, Gunstream J D, Povelones M, Walters E T (1996) Intrinsic injury signals enhance growth, survival, and excitability of *Aplysia* neurons. J Neurosci 16:7469-7477.

Antonov I, Antonova I, Kandel E R, Hawkins R D (2003) Activity-dependent presynaptic facilitation and hebbian LTP are both required and interact during classical conditioning in *Aplysia*. Neuron 37:135-147.

Bartsch D, Ghirardi M, Skehel P A, Karl K A, Herder S P, Chen M, Bailey C H, Kandel E R (1995) *Aplysia* CREB2 represses long-term facilitation: relief of repression converts transient facilitation into long-term functional and structural change. Cell 83:979-992.

Bedi S S, Salim A, Chen S, Glanzman D L (1998) Long-term effects of axotomy on excitability and growth of isolated *Aplysia* sensory neurons in cell culture: potential role of cAMP. J Neurophysiol 79:1371-1383.

Billy A J, Walters E T (1989) Long-term expansion and sensitization of mechanosensory receptive fields in *Aplysia* support an activity-dependent model of whole-cell sensory plasticity. J Neurosci 9:1254-1262.

Bredt D S, Snyder S H (1990) Isolation of nitric oxide synthetase, a calmodulin-requiring enzyme. Proc Natl Acad Sci USA 87:682-685.

Brunet J F, Shapiro E, Foster S A, Kandel E R, Iino Y (1991) Identification of a peptide specific for *Aplysia* sensory neurons by PCR-based differential screening. Science 252:856-859.

Bryan J (2004) Transdermal drug delivery may be a common technique in the future. Pharmaceutical J. 273:292-293.

Byrne J H, Kandel E R (1996) Presynaptic facilitation revisited: state and time dependence. J Neurosci 16:425-435.

Cha H, Shapiro P (2001) Tyrosine-phosphorylated extracellular signal regulated kinase associates with the Golgi complex during G2/M phase of the cell cycle: evidence for regulation of Golgi structure. J Cell Biol 153:1355-1367.

Chain D G, Casadio A, Schacher S, Hegde A N, Valbrun M, Yamamoto N, Goldberg A L, Bartsch D, Kandel E R, Schwartz J H (1999) Mechanisms for generating the autonomous cAMP-dependent protein kinase required for long-term facilitation in *Aplysia*. Neuron 22:147-156.

Chen Y, Devor M (1998) Ectopic mechanosensitivity in injured sensory axons arises from the site of spontaneous electrogenesis. Eur J Pain 2:165-178.

Clatworthy A L, Grose E (1999) Immune-mediated alterations in nociceptive sensory function in *Aplysia californica*. J Exp Biol 202:623-630.

Clatworthy A L, Illich P A, Castro G A, Walters E T (1995) Role of peri-axonal inflammation in the development of thermal hyperalgesia and guarding behavior in a rat model of neuropathic pain. Neurosci Lett 184:5-8.

Crown E D, Ye Z, Johnson K M, Xu G Y, AcAdoo D J, Westlund K N, Hulsebosch C E (2005) Upregulation of the phosphorylated form of CREB in spinothalamic tract cells following spinal cord injury: relation to central neuropathic pain. Neurosci Lett 384:139-144.

Dagan D, Levitan I B (1981) Isolated identified *Aplysia* neurons in cell culture. J Neurosci 1:736-740.

Dale N, Schacher S, Kandel E R (1988) Long-term facilitation in *Aplysia* involves increase in transmitter release. Science 239:282-285.

Dash P K, Tian L M, Moore A N (1998) Sequestration of cAMP response element-binding proteins by transcription factor decoys causes collateral elaboration of regenerating *Aplysia* motor neuron axons. Proc Natl Acad Sci USA 95:8339-8344.

DesGroseillers L, Auclair D, Wickham L, Maalouf M (1994) A novel actin cDNA is expressed in the neurons of *Aplysia californica*. Biochim Biophys Acta 1217:322-324.

Farr M, Mathews J, Zhu D F, Ambron R T (1999) Inflammation causes a long-term hyperexcitability in the nociceptive sensory neurons of *Aplysia*. Learn Mem 6:331-340.

Farr M, Zhu D F, Povelones M, Valcich D, Ambron R T (2001) Direct interactions between immunocytes and neurons after axotomy in *Aplysia*. J Neurobiol 46:89-96.

Fiallos-Estrada C E, Kummer W, Mayer B, Bravo R, Zimmermann M, Herdegen T (1993) Long-lasting increase of nitric oxide synthetase immunoreactivity, NADPH-diaphorase reaction and c-JUN co-expression in rat dorsal root ganglion neurons following sciatic nerve transection. Neurosci Lett 150:169-173.

Francis S H, Corbin J D (1994) Structure and function of cyclic nucleotide dependent protein kinases. Annu Rev Physiol 56:237-272.

Ghirardi M, Braha O, Hochner B, Montarolo P G, Kandel E R, Dale N (1992) Roles of PKA and PKC in facilitation of evoked and spontaneous transmitter release at depressed and nondepressed synapses in *Aplysia* sensory neurons. Neuron 9:479-489.

Glanzman D L, Kandel E R, Schacher S (1989) Identified target motor neuron regulates neurite outgrowth and synapse formation of *Aplysia* sensory neurons in vitro. Neuron 3:441-450.

Glass D B, Krebs E G (1982) Phosphorylation by guanosine 3':5'-monophosphate-dependent protein kinase of synthetic peptide analogs of a site phosphorylated in histone H2B. J Biol Chem 257:1196-1200.

Goldsmith B A, Abrams T W (1992) cAMP modulates multiple $K^+$ currents, increasing spike duration and excitability in *Aplysia* sensory neurons. Proc Natl Acad Sci USA 89:11481-11485.

Gracely R H, Lynch S A, Bennett G J (1992) Painful neuropathy: altered central processing maintained dynamically by peripheral input. Pain 51:175-194.

Griffiths C, Wykes V, Bellamy T C, Garthwaite J. (2003) A new and simple method for delivering clamped nitric oxide concentrations in the physiological range: application to activation of guanylyl cyclase-coupled nitric oxide receptors. Mol Pharmacol. 64(6):1349-56.

Gudi T, Lohmann S M, Pilz R B (1997) Regulation of gene expression by cyclic GMP-dependent protein kinase requires nuclear translocation of the kinase: identification of a nuclear localization signal. Mol Cell Biol 17:5244-5254.

Gunstream J D, Castro G A, Walters E T (1995) Retrograde transport of plasticity signals in *Aplysia* sensory neurons following axonal injury. J Neurosci 15:439-448.

Hall K U, Collins S P, Gamm D M, Massa E, DePaoli-Roach A A, Uhler M D (1999) Phosphorylation-dependent inhibition of protein phosphatase-1 by G-substrate. A Purkinje cell substrate of the cyclic GMP-dependent protein kinase. J Biol Chem 274:3485-3495.

Hanz S, Perlson E, Willis D, Zheng J Q, Massarwa R, Huerta J J, Koltzenburg M, Kohler M, van-Minnen J, Twiss J L, Fainzilber M (2003) Axoplasmic importins enable retrograde injury signaling in lesioned nerve. Neuron 40:1095-1104.

Internation Patent Application No. PCT/US92/07124, Publication No. WO93/03730.

Ji R R, Woolf C J (2001) Neuronal plasticity and signal transduction in nociceptive neurons: implications for the initiation and maintenance of pathological pain. Neurobiol Dis 8:1-10.

Johanson S O, Crouch M F, Hendry I A (1995) Retrograde axonal transport of signal transduction proteins in rat sciatic nerve. Brain Res 690:55-63.

Karin M (1994) Signal transduction from the cell surface to the nucleus through the phosphorylation of transcription factors. Curr Opin Cell Biol 6:415-424.

Kim Y I, Na H S, Kim S H, Han H C, Yoon Y W, Sung B, Nam H J, Shin S L, Hong S K (1998) Cell type-specific changes of the membrane properties of peripherally-axotomized dorsal root ganglion neurons in a rat model of neuropathic pain. Neuroscience 86:301-309.

LaMotte R H, Shain C N, Simone D A, Tsai E F P (1991) Neurogenic hyperalgesia: psychophysical studies of underlying mechanisms. J Neurophysiol 66:190-211.

Lee J H, Orice R H, Williams F G, Mayer B, Beitz A J (1993) Nitric oxide synthase is found in some spinothalamic neurons and in neuronal processes that appose spinal neurons that express Fos induced by noxious stimulation. Brain Res 608:324-333.

Lewin M R, Walters E T (1999) Cyclic GMP pathway is critical for inducing long-term sensitization of nociceptive sensory neurons. Nat Neurosci 2:18-23.

Liao X, Gunstream J D, Lewin M R, Ambron R T, Walters E T (1999) Activation of protein kinase A contributes to the expression but not the induction of long-term hyperexcitability caused by axotomy of *Aplysia* sensory neurons. J Neurosci 19:1247-1256.

Lin H, Bao J, Sung Y J, Walters E T, Ambron R T (2003) Rapid electrical and delayed molecular signals regulate the serum response element after nerve injury: convergence of injury and learning signals. J Neurobiol 57:204-220.

Mai et al. (2002) Efficiency of protein transduction is cell type-dependent and is enhanced by dextran sulfate. J Biol Chem 277:30208-30218.

Marais R, Wynne J, Treisman R (1993) The SRF accessory protein Elk-1 contains a growth factor-regulated transcriptional activation domain. Cell 73:381-393.

Martin K C, Michael D, Rose J C, Barad M, Casadio A, Zhu H, Kandel E R (1997) MAP kinase translocates into the nucleus of the presynaptic cell and is required for long-term facilitation in *Aplysia*. Neuron 18:899-912.

Michael D, Martin K C, Seger R, Ning M M, Baston R, Kandel E R (1998) Repeated pulses of serotonin required for long-term facilitation activate mitogen-activated protein kinase in sensory neurons of *Aplysia*. Proc Natl Acad Sci USA 95:1864-1869.

Mo E, Amin H, Bianco I H, Garthwaite J. (2004) Kinetics of a cellular nitric oxide/cGMP/phosphodiesterase-5 pathway. J Biol. Chem. 279(25):26149-58.

Millan M J (1999) The induction of pain: an integrative review. Prog Neurobiol 57:1-164.

Monfort P, Munoz M D, Kosenko E, Felipo V (2002) Long-term potentiation in hippocampus involves sequential activation of soluble guanylate cyclase, cGMP-dependent protein kinase, and cGMP-degrading phosphodiesterase. J Neurosci 22:10116-10122.

Moroz L L, Chen D, Gillette M U, Gillette R (1996) Nitric oxide synthase activity in the molluscan CNS. J Neurochem 66:873-876.

Muller U, Carew T J (1998) Serotonin induces temporally and mechanistically distinct phases of persistent PKA activity in *Aplysia* sensory neurons. Neuron 21:1423-1434.

Palecek J, Paleckova V, Willis W D (2003) Fos expression in spinothalamic and postsynaptic dorsal column neurons following noxious visceral and cutaneous stimuli. Pain 104:249-257.

Park S Y, Choi J Y, Kim R U, Lee Y S, Cho H J, Kim D S (2003) Downregulation of voltage-gated potassium channel a gene expression by axotomy and neurotrophins in rat dorsal root ganglia. Mol Cells 16:256-259.

Sarjeant J M, Lawrie A, Kinnear C, Yablonsky S, Leung W, Massaeli H, Prichett W, Veinrot J P, Rossart E, Rabinovitch M (2003) Apolipoprotein D inhibits platelet derived growth factor BB-induced vascular proliferated [sic] by preventing translocation of phosphorylated signal regulated kinase ½ to the nucleus. Arterioscler. Throm. Vasc. Biol. 23:2172-2177.

Pohler D, Butt E, Meissner J, Muller S, Lohse M, Walter U, Lohmann S M, Jarchau T (1995) Expression, purification, and characterization of the cGMP-dependent protein kinases I and II using the baculovirus system. FEBS Lett 374:419-425.

Schlossmann J, Feil R, Hofmann F (2003) Signaling through NO and cGMP-dependent protein kinases. Ann Med 35:21-27.

Schmied R, Ambron R T (1997) A nuclear localization signal targets proteins to the retrograde transport system, thereby evading uptake into organelles in *Aplysia* axons. J Neurobiol 33:151-160.

Schmied R, Huang C C, Zhang X P, Ambron D A, Ambron R T (1993) Endogenous axoplasmic proteins and proteins containing nuclear localization signal sequences use the retrograde axonal transport/nuclear import pathway in *Aplysia* neurons. J Neurosci 13:4064-4071.

Scholz K P, Byrne J H (1988) Intracellular injection of cAMP induces a longterm reduction of neuronal $K^+$ currents. Science 240:1664-1666.

Scott J D (1991) Cyclic nucleotide-dependent protein kinases. Pharmacol Ther 50:123-145.

Setyawan J, Koide K, Diller T C, Bunnage M E, Taylor S S, Nicolaou K C, Brunton L L (1999) Inhibition of protein kinases by balanol: specificity within the serine/threonine protein kinase subfamily. Mol Pharmacol. 56(2):370-6.

Smith A R, Visioli F, Hagen T M (2002) Vitamin C matters: increased oxidative stress in cultured human aortic endothelial cells without supplemental ascorbic acid. FASEB J 10.1096/fj.01-0825fje.

Smolenski A, Bachmann C, Reinhard K, Honig-Liedl P, Jarchau T, Hoschuetzky H, Walter U (1998) Analysis and regulation of vasodilator stimulated phosphoprotein serine 239 phosphorylation in vitro and in intact cells using a phosphospecific monoclonal antibody. J Biol Chem 273: 20029-20035.

Study R E, Kral M G (1996) Spontaneous action potential activity in isolated dorsal root ganglion neurons from rats with a painful neuropathy. Pain 65:235-242.

Sung Y J, Ambron R T (2004) Pathways that elicit long-term changes in gene expression in nociceptive neurons following nerve injury: contributions to neuropathic pain. Neurol Res 26:195-203.

Sung Y J, Hwang M C, Hwang Y W (1996) The dominant negative effects of H-Ras harboring a Gly to Ala mutation at position 60. J Biol Chem 271:30537-30543.

Sung Y J, Conti J, Currie J R, Brown W T, Denman R B (2000) RNAs that interact with the fragile X syndrome RNA binding protein FMRP. Biochem Biophys Res Commun 275: 973-980.

Sung Y J, Povelones M, Ambron R T (2001) RISK-1: a novel MAPK homologue in axoplasm that is activated and retrogradely transported after nerve injury. J Neurobiol 47:67-79.

Sung Y J, Dolzhanskaya N, Nolin S L, Brown T, Currie J R, Denman R B (2003) The fragile X mental retardation protein FMRP binds elongation factor 1A mRNA and negatively regulates its translation in vivo. J Biol Chem 278: 15669-15678.

Sung Y J and Ambron, R T (Mar. 22, 2004) Pathways that elicit long-term changes in gene expression in nociceptive neurons following nerve injury: contributions to neuropathic pain. Neurological Research 26:195-203.

Sung, Y J, Walters, E T and Ambron, R T (Aug. 25, 2004) A neuronal isoform of protein kinase G couples mitogen-activated protein kinase nuclear import to axotomy-induced long-term hyperexcitability in *Aplysia* sensory neurons. J. Neurosci. 24(34):7583-7595.

Sutton M A, Carew T J (2000) Parallel molecular pathways mediate expression of distinct forms of intermediate-term facilitation at tail sensory motor synapses in *Aplysia*. Neuron 26:219-231.

Ungless M A, Gasull X, Walters E T (2002) Long-term alteration of S-type potassium current and passive membrane properties in *Aplysia* sensory neurons following axotomy. J Neurophysiol 87:2408-2420.

U.S. Pat. No. 4,708,716 by Sibalis, D. Transdermal drug applicator. Filed Sep. 16, 1985 and issued Nov. 24, 1987.

U.S. Pat. No. 5,405,614, by D'Angelo; J P and Schur, H. Electronic transdermal drug delivery system. Filed Jan. 11, 1993 and issued Apr. 11, 1995.

U.S. Pat. No. 6,476,007 by Tao, Y and Johns, R A. Isoform-specific inhibition for treatment of pain and reduction of anesthetic threshold. Filed Dec. 8, 2000 and issued Nov. 5, 2002.

Urban M O and Gebhart G F (1999) Supraspinal contributions to hyperalgesia. Proc Natl Acad Sci USA 96:7687-7692.

Urban M O and Gebhart G F (1998) The glutamate synapse: a target in the pharmacological management of hyperalgesic pain states. Prog Brain Res 116:407-420.

Verge V M, Xu Z, Xu X J, Wiesenfeld-Hallin Z, Hokfelt T (1992) Marked increase in nitric oxide synthase mRNA in rat dorsal root ganglia after peripheral axotomy: in situ hybridization and functional studies. Proc Natl Acad Sci USA 89:11617-11621.

Wall P D, Devor M (1983) Sensory afferent impulses originate from dorsal root ganglia as well as from the periphery in normal and nerve injured rats. Pain 17:321-339.

Walters E T (1994) Injury-related behavior and neuronal plasticity: an evolutionary perspective on sensitization, hyperalgesia, and analgesia. Int Rev Neurobiol 36:325-427.

Walters E T, Byrne J H, Carew T J, Kandel E R (1983a) Mechanoafferent neurons innervating tail of *Aplysia*. I. Response properties and synaptic connections. J Neurophysiol 50:1522-1542.

Walters E T, Byrne J H, Carew T J, Kandel E R (1983b) Mechanoafferent neurons innervating tail of *Aplysia*. II. Modulation by sensitizing stimulation. J Neurophysiol 50:1543-1559.

Walters E T, Alizadeh H, Castro G A (1991) Similar neuronal alterations induced by axonal injury and learning in *Aplysia*. Science 253:797-799.

Walters E T, Bodnarova M, Billy A J, Dulin M F, Diaz-Rios M, Miller M W, Moroz L L (2004) Somatotopic organization and functional properties of mechanosensory neurons expressing sensorin-A mRNA in *Aplysia californica*. J Comp Neurol 471:219-240.

Wang H, Sun H, Della Penna K, Benz R J, Xu J, Gerhold D L, Holder D J, Koblan K S (2002) Chronic neuropathic pain is accompanied by global changes in gene expression and shares pathobiology with neurodegenerative diseases. Neuroscience 114:529-546.

Waxman S G, Kocsis J D, Black J A (1994) Type III sodium channel mRNA is expressed in embryonic but not adult spinal sensory neurons, and is reexpressed following axotomy. J Neurophysiol 72:466-470.

Wender et al. (2000) The design, synthesis, and evaluation of molecules that enable or enhance cellular uptake: peptoid molecular transporters. Proc Natl Acad Sci USA 97: 13003-13008.

Whitmarsh A J, Shore P, Sharrocks A D, Davis R J (1995) Integration of MAP kinase signal transduction pathways at the serum response element. Science 269:403-407.

Woolf C J (1983) Evidence for a central component of post-injury pain hypersensitivity. Nature 306:686-688.

Xu S, Robbins D, Frost J, Dang A, Lange-Carter C, Cobb MH (1995) MEKK1 phosphorylates MEK1 and MEK2 but does not cause activation of mitogenactivated protein kinase. Proc Natl Acad Sci USA 92:6808-6812.

Yang Z, Madinova A, Kozai T, Joch H, Aebi U, Luscher T F (2002) Felodipine inhibits nuclear translocation of p42/44 mitogen-activated protein kinase and human smooth muscle growth. Cardiovasc. Res. 53(1):227-231.

Yao Z, Dolginov Y, Hanoch T, Yung Y, Ridner G, Lando Z, Zharhary D, Seger R (2000) Detection of partially phosphorylated forms of ERK by monoclonal antibodies reveals spatial regulation of ERK activity by phosphatases. FEBS Lett 468:37-42.

Zaragoza C, Soria E, Lopez E, Browning D, Balbin M, Lopez-Otin C, Lamas S (2002) Activation of the mitogen activated protein kinase extracellular signal-regulated kinase 1 and 2 by the nitric oxide-cGMP-cGMP dependent protein kinase axis regulates the expression of matrix metalloproteinase 13 in vascular endothelial cells. Mol Pharmacol 62:927-935.

Zhang H, Xie W, Xie Y (2005) Spinal cord injury triggers sensitization of wide dynamic range dorsal horn neurons in segments rostral to injury. Aug. 2, 2005 Brain Res, epub ahead of print. PMID 16083864.

Zhang J M, Donnelly D F, Song X J, Lamotte R H (1997) Axotomy increases the excitability of dorsal root ganglion cells with unmyelinated axons. J Neurophysiol 78:2790-2794.

Zhang X, Verge V, Wiesenfeld-Hallin Z, Ju G, Bredt D, Synder S H, Hokfelt T (1993) Nitric oxide synthase-like immunoreactivity in lumbar dorsal root ganglia and spinal cord of rat and monkey and effect of peripheral axotomy. J Comp Neurol 335:563-575.

Zhou B, Zhang Z Y (2002) The activity of the extracellular signal-regulated kinase 2 is regulated by the differential phosphorylation in the activation loop. J. Biol Chem 277: 13889-13899.

Zimmermann M (2001) Pathobiology of neuropathic pain. Eur J Pharmacol 429:23-37.

Various publications are cited herein, the contents of which are hereby incorporated by reference in their entireties.

What is claimed is:

1. A method of treating chronic pain in a human subject suffering from peripheral nervous system hyperalgesia, comprising administering, to the subject, an effective amount of an RNAi that decreases the level of human protein kinase G-1 alpha (type-I alpha PKG) protein in the cell body of a sensory neuron in the peripheral nervous system of the subject, wherein the RNAi is administered to the location from which the pain arises, and wherein the human protein kinase G-1 alpha (type-I alpha PKG) amino acid sequence is as set forth in SEQ ID NO:54.

2. A method of treating chronic pain in a human subject suffering from peripheral nervous system hyperalgesia, comprising administering, to the subject, an effective amount of an agent that decreases the level of human protein kinase G protein in the cell body of a sensory neuron in the peripheral nervous system of the subject, wherein the agent is administered to the location from which the pain arises, wherein the agent is an antisense nucleic acid molecule or RNAi that inhibits expression of human protein kinase G, and wherein the human protein kinase G amino acid sequence is as set forth in SEQ ID NO:54.

3. A method of inhibiting long-term hyperexcitability in the cell body of a sensory neuron in the peripheral nervous system of a human subject, comprising administering, to the subject, an effective amount of an agent that decreases the level of human protein kinase G protein in the cell body of the sensory neuron in the peripheral nervous system of the subject, wherein the agent is an RNAi that inhibits expression of human protein kinase G, and wherein the human protein kinase G amino acid sequence is as set forth in SEQ ID NO:54.

4. A method of inhibiting long-term hyperexcitability in the cell body of a sensory neuron in the peripheral nervous system of a human subject, comprising administering, to the subject, an effective amount of an agent that decreases the level of human protein kinase G protein in the cell body of the sensory neuron in the peripheral nervous system of the subject, wherein the agent is an antisense nucleic acid molecule that inhibits expression of human protein kinase G, and wherein the human protein kinase G amino acid sequence is as set forth in SEQ ID NO:54.

5. The method of any one of claims 1, 2, 3, or 4, wherein the sensory neuron is a human sensory neuron.

6. The method of claim 1, wherein the RNAi is administered topically.

7. The method of claim 1, wherein the RNAi is administered by local injection.

8. The method of claim 2, 3, or 4, wherein the agent is administered topically.

9. The method of claim 2, 3, or 4, wherein the agent is administered by local injection.

* * * * *

UNITED STATES PATENT AND TRADEMARK OFFICE
CERTIFICATE OF CORRECTION

PATENT NO. : 8,252,754 B2
APPLICATION NO. : 11/385455
DATED : August 28, 2012
INVENTOR(S) : Richard Ambron et al.

Page 1 of 1

It is certified that error appears in the above-identified patent and that said Letters Patent is hereby corrected as shown below:

In the Specifications:

Column 1, lines 9-14:
GRANT INFORMATION
The subject matter of this application was developed at least in part under National Institutes of Health Grants NS12250 and NS35979, so that the United States Government has certain rights herein.

should read

--STATEMENT REGARDING FEDERALLY SPONSORED RESEARCH OR DEVELOPMENT
This invention was made with government support under grant numbers NS022150 and NS35979 awarded by the National Institutes of Health. The government has certain rights in the invention.--

Signed and Sealed this
Seventh Day of May, 2013

Teresa Stanek Rea
*Acting Director of the United States Patent and Trademark Office*